US007700118B2

(12) United States Patent
Behr et al.

(10) Patent No.: US 7,700,118 B2
(45) Date of Patent: Apr. 20, 2010

(54) MOLECULAR DIFFERENCES BETWEEN SPECIES OF THE *M. TUBERCULOSIS* COMPLEX

(75) Inventors: Marcel Behr, Montreal (CA); Peter Small, Seattle, WA (US); Gary Schoolnik, Stanford, CA (US); Michael A. Wilson, Austin, TX (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 12/049,063

(22) Filed: Mar. 14, 2008

(65) Prior Publication Data

US 2008/0254052 A1 Oct. 16, 2008

Related U.S. Application Data

(63) Continuation of application No. 11/143,401, filed on Jun. 1, 2005, now Pat. No. 7,364,740, which is a continuation of application No. 10/647,089, filed on Aug. 21, 2003, now abandoned, which is a continuation of application No. 09/894,844, filed on Jun. 27, 2001, now Pat. No. 6,686,166, which is a continuation of application No. 09/318,191, filed on May 25, 1999, now Pat. No. 6,291,190.

(60) Provisional application No. 60/097,936, filed on Aug. 25, 1998.

(51) Int. Cl.
*A61K 39/04* (2006.01)
*A61K 39/205* (2006.01)
*A61K 39/00* (2006.01)

(52) U.S. Cl. ...................... 424/248.1; 424/9.1; 424/9.2; 424/93.2; 424/185.1; 424/234.1

(58) Field of Classification Search .................. 424/9.1, 424/9.2, 93.2, 185.1, 234.1, 248.1
See application file for complete search history.

(56) References Cited

U.S. PATENT DOCUMENTS

| | | | |
|---|---|---|---|
| 5,134,142 | A | 7/1992 | Matsuo et al. |
| 5,686,597 | A | 11/1997 | Coleman et al. |
| 5,700,683 | A | 12/1997 | Stover |
| 5,776,465 | A | 7/1998 | O'Donnell et al. |
| 5,955,356 | A | 9/1999 | Content et al. |
| 6,291,190 | B1 | 9/2001 | Behr et al. |

FOREIGN PATENT DOCUMENTS

| | | |
|---|---|---|
| EP | 0681026 | 11/1995 |
| WO | 96/27129 | 2/1996 |
| WO | 96/25519 | 8/1996 |
| WO | 98/29132 | 7/1998 |
| WO | 01/04151 | 1/2001 |

OTHER PUBLICATIONS

Agger et al., Vaccine, 2002, 21:7-14.
Aldovini, et al., 1993 Journal of Bacteriology, 175:7282-7289.
Behr, et al., 1999 Science, 284:1520-1523.
Brosch, et al., 1998 Infection & Immunity, 66(5):2221-2229.
Cole, et al., 1998 Nature, 393:537-544.
Cole, et al., Nature, Nov. 1998, Errata, 396:190-198.
Converse, et al., 1996 Infection & Immunity, 64(11):4776-4787.
Delahunty, et al., 1996 American Journal of Human Genetics, 58:1239-1246.
DeRisi, et al., 1996 Nature Genetics 14:457-460.
Doherty et al., Clin. Microbiol. Rev., 2005, 18(4):687-702.
Ganjam, et al., 1991 PNAS 88:5433-5437.
Gordon, et al., 1999 Molecular Microbiology, 32(3):643-655.
Hacia, et al., 1996 Nature Genetics, 14:441-447.
Jost, et al., 1994 Journal of Biochemistry, 269:26267-26273.
Lockhart, et al., 1996 Nature Biotechnology, 14:1675-1680.
Mahairas, G.G., et al., 1996 Journal of Bacteriology, 178(5):1274-1282.
Medina et al., J. Exp. Med., 1996, 183:1045-1051.
Norman, et al., 1995 Molecular Microbiology, 16:755-760.
Orme, Vaccine, 2006, 24:2-19.
Paul, et al., 1996 Journal of Infectious Diseases, 174(1):105-112.
Philipp, W.J., et al., 1996 Microbiology, 142(part II):2985-3135-3145.
Ramsay, et al., 1998 Nature Biotechnology, 16:40-44.
Riley, et al., 1990 Nucleic Acids Research, 18:2887-2890.
Rook et al., Vaccine, 2005, 23:2115-2120.
Sable et al., Clinical Immunology, 2007, 122:239-251.
Saiki, et al., 1985 Science, 239:487-491.
Sambrook, et al., 1989 Molecular Cloning: A Laboratory Manual, CSH Press, 14.2-14.33.
Shalon, et al., 1996 Genome Research 6:639-645.
Silver, et al., 1998 Infectino & Immunology 66(3):1190-1199.
Talbot, et al., 1997 Journal of Clinical Microbiology, 35:566-569.
Bruyn; et al., "The 32 KDA Protein Antigen of M. Bovis B.C.G. and *M. tuberculosis* H37RV", Tropical Medicine and Parasitology, Sep. 1, 1990, 41(3):331-2.

*Primary Examiner*—Rodney P. Swartz
(74) *Attorney, Agent, or Firm*—Bozicevic, Field & Francis LLP; Pamela J. Sherwood

(57) ABSTRACT

Specific genetic deletion are identified in mycobacteria isolates, including variations in the *M. tuberculosis* genome sequence between isolates, and numerous deletion present in BCG as compared to *M. tb*. These deletions are used as markers to distinguish between pathogenic and avirulent strains, and as a marker for particular *M. tb* isolates. Deletions specific to vaccine strains of BCG are useful in determining whether a positive tuberculin skin test is indicative of actual tuberculosis infection. The deleted sequences may be re-introduced into BCG to improve the efficacy of vaccination. Alternatively, the genetic sequence that corresponds to the deletion(s) are deleted from *M. bovis* or *M. tubercuosis* to attenuate the pathogenic bacteria.

9 Claims, No Drawings

MOLECULAR DIFFERENCES BETWEEN SPECIES OF THE *M. TUBERCULOSIS* COMPLEX

This invention was made with Government support under contract AI01137 and AI35969 awarded by the National Institutes of Health. The Government has certain rights in this invention.

Tuberculosis is an ancient human scourge that continues to be an important public health problem worldwide. It is an ongoing epidemic of staggering proportions. Approximately one in every three people in the world is infected with *Mycobacterium Tuberculosis*, and has a 10% lifetime risk of progressing from infection to clinical disease. Although tuberculosis can be treated, an estimated 2.9 million people died from the disease last year.

There are significant problems with a reliance on drug treatment to control active *M. tubercuosis* infections. Most of the regions having high infection rates are less developed countries, which suffer from a lack of easily accessible health services, diagnostic facilities and suitable antibiotics against *M. tubercuosis*. Even where these are available, patient compliance is often poor because of the lengthy regimen required for complete treatment, and multidrug-resistant strains are increasingly common.

Prevention of infection would circumvent the problems of treatment, and so vaccination against tuberculosis is widely performed in endemic regions. Around 100 million people a year are vaccinated with live bacillus Calmette-Guerin (BCG) vaccine. BCG has the great advantage of being inexpensive and easily administered under less than optimal circumstances, with few adverse reactions. Unfortunately, the vaccine is widely variable in its efficacy, providing anywhere from 0 to 80% protection against infection with *M. tuberculosis*.

BCG has an interesting history. It is an attenuated strain of *M. bovis*, a very close relative of *M. tubercuosis*. The *M. bovis* strain that became BCG was isolated from a cow in the late 1800's by a bacteriologist named Nocard, hence it was called Nocard's bacillus. The attenuation of Nocard's bacillus took place from 1908 to 1921, over the course of 230 in vitro passages. Thereafter, it was widely grown throughout the world, resulting in additional hundreds and sometime thousands of in vitro passages. Throughout its many years in the laboratory, there has been selection for cross-reaction with the tuberculin skin test, and for decreased side effects. The net results have been a substantially weakened pathogen, which may be ineffective in raising an adequate immune response.

New antituberculosis vaccines are urgently needed for the general population in endemic regions, for HIV-infected individuals, as well as health care professionals likely to be exposed to tubercle bacilli. Recombinant DNA vaccines bearing protective genes from virulent *M. tubercuosis* are being developed using shuttle plasmids to transfer genetic material from one mycobacterial species to another, for example see U.S. Pat. No. 5,776,465. Tuberculosis vaccine development should be given a high priority in current medical research goals.

Relevant Literature

Mahairas et al. (1996) *J Bacteriol* 178(5):1274-1282 provides a molecular analysis of genetic differences between *Mycobacterium bovis* BCG and virulent *M. bovis*. Subtractive genomic hybridization was used to identify genetic differences between virulent *M. bovis* and *M. tubercuosis* and avirulent BCG. U.S. Pat. No. 5,700,683 is directed to these genetic differences.

Cole et al. (1998) *Nature* 393:537-544 have described the complete genome of M. tuberculosis. To obtain the contiguous genome sequence, a combined approach was used that involved the systematic sequence analysis of selected large-insert clones as well as random small-insert clones from a whole-genome shotgun library. This culminated in a composite sequence of 4,411,529 base pairs, with a G+C content of 65.6%. 3,924 open reading frames were identified in the genome, accounting for ~91% of the potential coding capacity.

*Mycobacterium tuberculosis* (*M. tb.*) genomic sequence is available at several internet sites.

SUMMARY OF THE INVENTION

Genetic markers are provided that distinguish between strains of the *Mycobacterium tuberculosis* complex, particularly between avirulent and virulent strains. Strains of interest include *M. bovis, M. bovis* BCG strains, *M. tubercuosis* (*M. tb.*) isolates, and bacteriophages that infect mycobacteria. The genetic markers are used for assays, e.g. immunoassays, that distinguish between strains, such as to differentiate between BCG immunization and *M. tb.* infection. The protein products may be produced and used as an immunogen, in drug screening, etc. The markers are useful in constructing genetically modified *M. tb* or *M. bovis* cells having improved vaccine characteristics.

DETAILED DESCRIPTION OF THE EMBODIMENTS

Specific genetic deletions are identified that serve as markers to distinguish between avirulent and virulent mycobacteria strains, including *M. bovis, M. bovis* BCG strains, *M. tubercuosis* (*M. tb.*) isolates, and bacteriophages that infect mycobacteria. These deletions are used as genetic markers to distinguish between the different mycobacteria. The deletions may be introduced into *M. tb.* or *M. bovis* by recombinant methods in order to render a pathogenic strain avirulent. Alternatively, the deleted genes are identified in the *M. tb.* genome sequence, and are then reintroduced by recombinant methods into BCG or other vaccine strains, in order to improve the efficacy of vaccination.

The deletions of the invention are identified by comparative DNA hybridizations from genomic sequence of mycobacterium to a DNA microarray comprising representative sequences of the *M. tb.* coding sequences. The deletions are then mapped to the known *M. tb.* genome sequence in order to specifically identify the deleted gene(s), and to characterize nucleotide sequence of the deleted region.

Nucleic acids comprising the provided deletions and junctions are used in a variety of applications. Hybridization probes may be obtained from the known *M. tb.* sequence which correspond to the deleted sequences. Such probes are useful in distinguishing between mycobacteria. For example, there is a 10% probability that an *M. tb.* infected person will progress to clinical disease, but that probability may vary depending of the particular infecting strain. Analysis for the presence or absence of the deletions provided below as "*M. tb* variable" is used to distinguish between different *M. tb.* strains. The deletions are also useful in identifying whether a patient that is positive for a tuberculin skin test has been infected with *M. tb.* or with BCG.

In another embodiment of the invention, mycobacteria are genetically altered to delete sequences identified herein as absent in attenuated strains, but present in pathogenic strains, e.g. deletions found in BCG but present in *M. tb.* H37Rv. Such genetically engineered strains may provide superior vaccines to the present BCG isolates in use. Alternatively, BCG strains may be "reconstructed" to more closely resemble wild-type *M. tb.* by inserting certain of the deleted sequences back into the genome. Since the protein products of the deleted sequences are expressed in virulent mycobacterial species, the encoded proteins are useful as immunogens for vaccination.

The attenuation (loss of virulence) in BCG is attributed to the loss of genetic material at a number of places throughout the genome. The selection over time for fewer side-effects resulting from BCG immunization, while retaining cross-reactivity with the tuberculin skin test, has provided an excellent screen for those sequences that engender side effects. The identification of deletions that vary between BCG isolates identifies such sequences, which may be used in drug screening and biological analysis for the role of the deleted genes in causing untoward side effects and pathogenicity.

Identification of *M. Tuberculosis* Complex Deletion Markers

The present invention provides nucleic acid sequences that are markers for specific mycobacteria, including *M. tb., M. bovis*, BCG and bacteriophage. The deletions are listed in Table 1. The absence or presence of these marker sequences is characteristic of the indicated isolate, or strain. As such, they provide a unique characteristic for the identification of the indicated mycobacteria. The deletions are identified by their *M. tb.* open reading frame ("Rv" nomenclature), which corresponds to a known genetic sequence, and may be accessed as previously cited. The junctions of the deletions are provided by the designation of position in the publicly available *M. tb.* sequence.

TABLE 1

| SEQ ID | rd | rv_num | orf_id | breakpoint |
|---|---|---|---|---|
| SEQ ID NO: 1 | RD01 | Rv3871 | MTV027.06 | "H37Rv, segment 160: 7534, 16989" |
| SEQ ID NO: 2 | RD01 | Rv3872 | MTV027.07 | "H37Rv, segment 160: 7534, 16989" |
| SEQ ID NO: 3 | RD01 | Rv3873 | MTV027.08 | "H37Rv, segment 160: 7534, 16989" |
| SEQ ID NO: 4 | RD01 | Rv3874 | MTV027.09 | "H37Rv, segment 160: 7534, 16989" |
| SEQ ID NO: 5 | RD01 | Rv3875 | MTV027.10 | "H37Rv, segment 160: 7534, 16989" |
| SEQ ID NO: 6 | RD01 | Rv3876 | MTV027.11 | "H37Rv, segment 160: 7534, 16989" |
| SEQ ID NO: 7 | RD01 | Rv3877 | MTV027.12 | "H37Rv, segment 160: 7534, 16989" |
| SEQ ID NO: 8 | RD01 | Rv3878 | MTV027.13 | "H37Rv, segment 160: 7534, 16989" |
| SEQ ID NO: 9 | RD01 | Rv3879c | MTV027.14c | "H37Rv, segment 160: 7534, 16989" |
| SEQ ID NO: 10 | RD02 | Rv1988 | MTCY39.31c | "H37Rv segment 88: 14211, segment 89: 8598" |
| SEQ ID NO: 11 | RD02 | Rv1987 | MTCY39.32c | "H37Rv segment 88: 14211, segment 89: 8598" |
| SEQ ID NO: 12 | RD02 | Rv1986 | MTCY39.33c | "H37Rv segment 88: 14211, segment 89: 8598" |
| SEQ ID NO: 13 | RD02 | Rv1985c | MTCY39.34 | "H37Rv segment 88: 14211, segment 89: 8598" |
| SEQ ID NO: 14 | RD02 | Rv1984c | MTCY39.35 | "H37Rv segment 88: 14211, segment 89: 8598" |
| SEQ ID NO: 15 | RD02 | Rv1983 | MTCY39.36c | "H37Rv segment 88: 14211, segment 89: 8598" |
| SEQ ID NO: 16 | RD02 | Rv1982c | MTCY39.37 | "H37Rv segment 88: 14211, segment 89: 8598" |
| SEQ ID NO: 17 | RD02 | Rv1981c | MTCY39.38 | "H37Rv segment 88: 14211, segment 89: 8598" |
| SEQ ID NO: 18 | RD02 | Rv1980c | MTCY39.39 | "H37Rv segment 88: 14211, segment 89: 8598" |
| SEQ ID NO: 19 | RD02 | Rv1979c | MTCY39.40 | "H37Rv segment 88: 14211, segment 89: 8598" |
| SEQ ID NO: 20 | RD02 | Rv1978 | MTV051.16 | "H37Rv segment 88: 14211, segment 89: 8598" |
| SEQ ID NO: 21 | RD03 | Rv1586c | MTCY336.18 | "H37Rv, segment 70: 7677, 16923" |
| SEQ ID NO: 22 | RD03 | Rv1585c | MTCY336.19 | "H37Rv, segment 70: 7677, 16923" |
| SEQ ID NO: 23 | RD03 | Rv1584c | MTCY336.20 | "H37Rv, segment 70: 7677, 16923" |
| SEQ ID NO: 24 | RD03 | Rv1583c | MTCY336.21 | "H37Rv, segment 70: 7677, 16923" |
| SEQ ID NO: 25 | RD03 | Rv1582c | MTCY336.22 | "H37Rv, segment 70: 7677, 16923" |
| SEQ ID NO: 26 | RD03 | Rv1581c | MTCY336.23 | "H37Rv, segment 70: 7677, 16923" |
| SEQ ID NO: 27 | RD03 | Rv1580c | MTCY336.24 | "H37Rv, segment 70: 7677, 16923" |
| SEQ ID NO: 28 | RD03 | Rv1579c | MTCY336.25 | "H37Rv, segment 70: 7677, 16923" |
| SEQ ID NO: 29 | RD03 | Rv1578c | MTCY336.26 | "H37Rv, segment 70: 7677, 16923" |
| SEQ ID NO: 30 | RD03 | Rv1577c | MTCY336.27 | "H37Rv, segment 70: 7677, 16923" |
| SEQ ID NO: 31 | RD03 | Rv1576c | MTCY336.28 | "H37Rv, segment 70: 7677, 16923" |
| SEQ ID NO: 32 | RD03 | Rv1575 | MTCY336.29c | "H37Rv, segment 70: 7677, 16923" |
| SEQ ID NO: 33 | RD03 | Rv1574 | MTCY336.30c | "H37Rv, segment 70: 7677, 16923" |
| SEQ ID NO: 34 | RD03 | Rv1573 | MTCY336.31c | "H37Rv, segment 70: 7677, 16923" |
| SEQ ID NO: 35 | RD04 | Rv0221 | MTCY08D5.16 | "H37Rv, segment 12: 17432, 19335" |
| SEQ ID NO: 36 | RD04 | Rv0222 | MTCY08D5.17 | "H37Rv, segment 12: 17432, 19335" |
| SEQ ID NO: 37 | RD04 | Rv0223c | MTCY08D5.18 | "H37Rv, segment 12: 17432, 19335" |
| SEQ ID NO: 38 | RD05 | Rv3117 | MTCY164.27 | "H37Rv, segment 135: 27437, 30212" |
| SEQ ID NO: 39 | RD05 | Rv3118 | MTCY164.28 | "H37Rv, segment 135: 27437, 30212" |
| SEQ ID NO: 40 | RD05 | Rv3119 | MTCY164.29 | "H37Rv, segment 135: 27437, 30212" |
| SEQ ID NO: 41 | RD05 | Rv3120 | MTCY164.30 | "H37Rv, segment 135: 27437, 30212" |
| SEQ ID NO: 42 | RD05 | Rv3121 | MTCY164.31 | "H37Rv, segment 135: 27437, 30212" |
| SEQ ID NO: 43 | RD06 | Rv1506c | MTCY277.28c | "H37Rv, segment 65: 23614, 36347" |
| SEQ ID NO: 44 | RD06 | Rv1507c | MTCY277.29c | "H37Rv, segment 65: 23614, 36347" |
| SEQ ID NO: 45 | RD06 | Rv1508c | MTCY277.30c | "H37Rv, segment 65: 23614, 36347" |
| SEQ ID NO: 46 | RD06 | Rv1509 | MTCY277.31 | "H37Rv, segment 65: 23614, 36347" |
| SEQ ID NO: 47 | RD06 | Rv1510 | MTCY277.32 | "H37Rv, segment 65: 23614, 36347" |
| SEQ ID NO: 48 | RD06 | Rv1511 | MTCY277.33 | "H37Rv, segment 65: 23614, 36347" |
| SEQ ID NO: 49 | RD06 | Rv1512 | MTCY277.34 | "H37Rv, segment 65: 23614, 36347" |
| SEQ ID NO: 50 | RD06 | Rv1513 | MTCY277.35 | "H37Rv, segment 65: 23614, 36347" |
| SEQ ID NO: 51 | RD06 | Rv1514c | MTCY277.36c | "H37Rv, segment 65: 23614, 36347" |
| SEQ ID NO: 52 | RD06 | Rv1515c | MTCY277.37c | "H37Rv, segment 65: 23614, 36347" |
| SEQ ID NO: 53 | RD06 | Rv1516c | MTCY277.38c | "H37Rv, segment 65: 23614, 36347" |

TABLE 1-continued

| SEQ ID | rd | rv__num | orf__id | breakpoint |
|---|---|---|---|---|
| SEQ ID NO: 54 | RD07 | Rv2346c | MTCY98.15c | "H37Rv, segment 103: 17622, 26584" |
| SEQ ID NO: 55 | RD07 | Rv2347c | MTCY98.16c | "H37Rv, segment 103: 17622, 26584" |
| SEQ ID NO: 56 | RD07 | Rv2348c | MTCY98.17c | "H37Rv, segment 103: 17622, 26584" |
| SEQ ID NO: 57 | RD07 | Rv2349c | MTCY98.18c | "H37Rv, segment 103: 17622, 26584" |
| SEQ ID NO: 58 | RD07 | Rv2350c | MTCY98.19c | "H37Rv, segment 103: 17622, 26584" |
| SEQ ID NO: 59 | RD07 | Rv2351c | MTCY98.20c | "H37Rv, segment 103: 17622, 26584" |
| SEQ ID NO: 60 | RD07 | Rv2352c | MTCY98.21c | "H37Rv, segment 103: 17622, 26584" |
| SEQ ID NO: 61 | RD07 | Rv2353c | MTCY98.22c | "H37Rv, segment 103: 17622, 26584" |
| SEQ ID NO: 62 | RD08 | Rv0309 | MTCY63.14 | "H37Rv, segment 16: 17018, 20446" |
| SEQ ID NO: 63 | RD08 | Rv0310c | MTCY63.15c | "H37Rv, segment 16: 17018, 20446" |
| SEQ ID NO: 64 | RD08 | Rv0311 | MTCY63.16 | "H37Rv, segment 16: 17018, 20446" |
| SEQ ID NO: 65 | RD08 | Rv0312 | MTCY63.17 | "H37Rv, segment 16: 17018, 20446" |
| SEQ ID NO: 66 | RD09 | Rv3623 | MTCY15C10.29c | "H37Rv, segment 153: 21131, segment 154: 2832" |
| SEQ ID NO: 67 | RD09 | Rv3622c | MTCY15C10.30 | "H37Rv, segment 153: 21131, segment 154: 2832" |
| SEQ ID NO: 68 | RD09 | Rv3621c | MTCY15C10.31 | "H37Rv, segment 153: 21131, segment 154: 2832" |
| SEQ ID NO: 69 | RD09 | Rv3620c | MTCY15C10.32 | "H37Rv, segment 153: 21131, segment 154: 2832" |
| SEQ ID NO: 70 | RD09 | Rv3619c | MTCY15C10.33 | "H37Rv, segment 153: 21131, segment 154: 2832" |
| SEQ ID NO: 71 | RD09 | Rv3618 | MTCY15C10.34c | "H37Rv, segment 153: 21131, segment 154: 2832" |
| SEQ ID NO: 72 | RD09 | Rv3617 | MTCY15C10.35c | "H37Rv, segment 153: 21131, segment 154: 2832" |
| SEQ ID NO: 73 | RD10 | Rv1257c | MTCY50.25 | "H37Rv segment 55: 3689, 6696" |
| SEQ ID NO: 74 | RD10 | Rv1256c | MTCY50.26 | "H37Rv segment 55: 3689, 6696" |
| SEQ ID NO: 75 | RD10 | Rv1255c | MTCY50.27 | "H37Rv segment 55: 3689, 6696" |
| SEQ ID NO: 76 | RD11 | Rv3429 | MTCY77.01 | "H37Rv, segment 145: 30303 to segment 146: 1475" |
| SEQ ID NO: 77 | RD11 | Rv3428c | MTCY78.01 | "H37Rv, segment 145: 30303 to segment 146: 1475" |
| SEQ ID NO: 78 | RD11 | Rv3427c | MTCY78.02 | "H37Rv, segment 145: 30303 to segment 146: 1475" |
| SEQ ID NO: 79 | RD11 | Rv3426 | MTCY78.03c | "H37Rv, segment 145: 30303 to segment 146: 1475" |
| SEQ ID NO: 80 | RD11 | Rv3425 | MTCY78.04c | "H37Rv, segment 145: 30303 to segment 146: 1475" |
| SEQ ID NO: 81 | RD12 | Rv2072c | MTCY49.11c | "H37Rv segment 93: 9301, 11331" |
| SEQ ID NO: 82 | RD12 | Rv2073c | MTCY49.12c | "H37Rv segment 93: 9301, 11331" |
| SEQ ID NO: 83 | RD12 | Rv2074 | MTCY49.13 | "H37Rv segment 93: 9301, 11331" |
| SEQ ID NO: 84 | RD12 | Rv2075c | MTCY49.14c | "H37Rv segment 93: 9301, 11331" |
| SEQ ID NO: 85 | RD13bis | Rv2645 | MTCY441.15 | "H37Rv, segment 118: 12475, 23455" |
| SEQ ID NO: 86 | RD13bis | Rv2646 | MTCY441.16 | "H37Rv, segment 118: 12475, 23455" |
| SEQ ID NO: 87 | RD13bis | Rv2647 | MTCY441.17 | "H37Rv, segment 118: 12475, 23455" |
| SEQ ID NO: 88 | RD13bis | Rv2648 | MTCY441.17A | "H37Rv, segment 118: 12475, 23455" |
| SEQ ID NO: 89 | RD13bis | Rv2649 | MTCY441.18 | "H37Rv, segment 118: 12475, 23455" |
| SEQ ID NO: 90 | RD13bis | Rv2650c | MTCY441.19 | "H37Rv, segment 118: 12475, 23455" |
| SEQ ID NO: 91 | RD13bis | Rv2651c | MTCY441.20c | "H37Rv, segment 118: 12475, 23455" |
| SEQ ID NO: 92 | RD13bis | Rv2652c | MTCY441.21c | "H37Rv, segment 118: 12475, 23455" |
| SEQ ID NO: 93 | RD13bis | Rv2653c | MTCY441.22c | "H37Rv, segment 118: 12475, 23455" |
| SEQ ID NO: 94 | RD13bis | Rv2654c | MTCY441.23c | "H37Rv, segment 118: 12475, 23455" |
| SEQ ID NO: 95 | RD13bis | Rv2655c | MTCY441.24c | "H37Rv, segment 118: 12475, 23455" |
| SEQ ID NO: 96 | RD13bis | Rv2656c | MTCY441.25c | "H37Rv, segment 118: 12475, 23455" |
| SEQ ID NO: 97 | RD13bis | Rv2657c | MTCY441.26c | "H37Rv, segment 118: 12475, 23455" |
| SEQ ID NO: 98 | RD13bis | Rv2658c | MTCY441.27c | "H37Rv, segment 118: 12475, 23455" |
| SEQ ID NO: 99 | RD13bis | Rv2659c | MTCY441.28c | "H37Rv, segment 118: 12475, 23455" |
| SEQ ID NO: 100 | RD13bis | Rv2660c | MTCY441.29c | "H37Rv, segment 118: 12475, 23455" |
| SEQ ID NO: 101 | RD14 | Rv1766 | MTCY28.32 | "H37Rv segment 79: 30573, 39642" |
| SEQ ID NO: 102 | RD14 | Rv1767 | MTCY28.33 | "H37Rv segment 79: 30573, 39642" |
| SEQ ID NO: 103 | RD14 | Rv1768 | MTCY28.34 | "H37Rv segment 79: 30573, 39642" |
| SEQ ID NO: 104 | RD14 | Rv1769 | MTCY28.35 | "H37Rv segment 79: 30573, 39642" |
| SEQ ID NO: 105 | RD14 | Rv1770 | MTCY28.36 | "H37Rv segment 79: 30573, 39642" |
| SEQ ID NO: 106 | RD14 | Rv1771 | MTCY28.37 | "H37Rv segment 79: 30573, 39642" |
| SEQ ID NO: 107 | RD14 | Rv1772 | MTCY28.38 | "H37Rv segment 79: 30573, 39642" |
| SEQ ID NO: 108 | RD14 | Rv1773c | MTCY28.39 | "H37Rv segment 79: 30573, 39642" |
| SEQ ID NO: 109 | RD15 | Rv1963c | MTV051.01c | "H37Rv segment 88: 1153, 13873" |
| SEQ ID NO: 110 | RD15 | Rv1964 | MTV051.02 | "H37Rv segment 88: 1153, 13873" |
| SEQ ID NO: 111 | RD15 | Rv1965 | MTV051.03 | "H37Rv segment 88: 1153, 13873" |
| SEQ ID NO: 112 | RD15 | Rv1966 | MTV051.04 | "H37Rv segment 88: 1153, 13873" |
| SEQ ID NO: 113 | RD15 | Rv1967 | MTV051.05 | "H37Rv segment 88: 1153, 13873" |
| SEQ ID NO: 114 | RD15 | Rv1968 | MTV051.06 | "H37Rv segment 88: 1153, 13873" |
| SEQ ID NO: 115 | RD15 | Rv1969 | MTV051.07 | "H37Rv segment 88: 1153, 13873" |
| SEQ ID NO: 116 | RD15 | Rv1970 | MTV051.08 | "H37Rv segment 88: 1153, 13873" |
| SEQ ID NO: 117 | RD15 | Rv1971 | MTV051.09 | "H37Rv segment 88: 1153, 13873" |
| SEQ ID NO: 118 | RD15 | Rv1972 | MTV051.10 | "H37Rv segment 88: 1153, 13873" |
| SEQ ID NO: 119 | RD15 | Rv1973 | MTV051.11 | "H37Rv segment 88: 1153, 13873" |
| SEQ ID NO: 120 | RD15 | Rv1974 | MTV051.12 | "H37Rv segment 88: 1153, 13873" |
| SEQ ID NO: 121 | RD15 | Rv1975 | MTV051.13 | "H37Rv segment 88: 1153, 13873" |
| SEQ ID NO: 122 | RD15 | Rv1976c | MTV051.14 | "H37Rv segment 88: 1153, 13873" |
| SEQ ID NO: 123 | RD15 | Rv1977 | MTV051.15 | "H37Rv segment 88: 1153, 13873" |
| SEQ ID NO: 124 | RD16 | Rv3405c | MTCY78.23 | "H37Rv, segment 145: 5012, 12621" |
| SEQ ID NO: 125 | RD16 | Rv3404c | MTCY78.24 | "H37Rv, segment 145: 5012, 12621" |
| SEQ ID NO: 126 | RD16 | Rv3403c | MTCY78.25 | "H37Rv, segment 145: 5012, 12621" |
| SEQ ID NO: 127 | RD16 | Rv3402c | MTCY78.26 | "H37Rv, segment 145: 5012, 12621" |
| SEQ ID NO: 128 | RD16 | Rv3401 | MTCY78.27c | "H37Rv, segment 145: 5012, 12621" |
| SEQ ID NO: 129 | RD16 | Rv3400 | MTCY78.28c | "H37Rv, segment 145: 5012, 12621" |

The "Rv" column indicates public *M. tb.* sequence, open reading frame. The BCG strains were obtained as follows:

TABLE 2

Strains employed in study of BCG phylogeny

| Name of strain | Synonym | Source | Descriptors |
|---|---|---|---|
| BCG-Russia | Moscow | ATCC | # 35740 |
| BCG-Moreau | Brazil | ATCC | # 35736 |
| BCG-Moreau | Brazil | IAF | dated 1958 |
| BCG-Moreau | Brazil | IAF | dated 1961 |
| BCG-Japan | Tokyo | ATCC | # 35737 |
| BCG-Japan | Tokyo | IAF | dated 1961 |
| BCG-Japan | Tokyo | JATA | vaccine strain |
| BCG-Japan | Tokyo | JATA | bladder cancer strain |
| BCG-Japan | Tokyo | JATA | clinical isolate-adenitis |
| BCG-Sweden | Gothenburg | ATCC | # 35732 |
| BCG-Sweden | Gothenburg | IAF | dated 1958 |
| BCG-Sweden | Gothenburg | SSI | production lot, Copenhagen |
| BCG-Phipps | Philadelphia | ATCC | # 35744 |
| BCG-Denmark | Danish 1331 | ATCC | # 35733 |
| BCG-Copenhagen | | ATCC | #27290 |
| BCG-Copenhagen | | IAF | dated 1961 |
| BCG-Tice | Chicago | vaccine | dated 1973 |
| BCG-Tice | Chicago | ATCC | # 35743 |
| BCG-Frappier | Montreal | IAF | primary lot, 1973 |
| BCG-Frappier, INH-resistant | Montreal-R | IAF | primary lot, 1973 |
| BCG-Frappier | Montreal | IAF | passage 946 |
| BCG-Connaught | Toronto | CL | bladder cancer treatment |
| BCG-Birkhaug | | ATCC | # 35731 |
| BCG-Prague | Czech | SSI | lyophilized 1968 |
| BCG-Glaxo | | vaccine | dated 1973 |
| BCG-Glaxo | | ATCC | # 35741 |
| BCG-Pasteur | | IAF | passage 888 |
| BCG-Pasteur | | IAF | dated 1961 |
| BCG-Pasteur | | IP | 1173P2-B |
| BCG-Pasteur | | IP | 1173P2-C |
| BCG-Pasteur | | IP | clinical isolate # 1 |
| BCG-Pasteur | | IP | clinical isolate # 2 |
| BCG-Pasteur | | ATCC | # 35734 |

Abbreviations:
IP = Institut Pasteur, Paris, France;
IAF = Institut Armand Frappier, Laval, Canada;
ATCC = American Type Culture Collection, Rockville, Md, USA;
SSI = Statens Serum Institute, Copenhagen, Denmark;
CL = Connaught Laboratories, Willowdale, Canada,
JATA = Japanese Anti-Tuberculosis Association;
INH = isoniazid. Canadian BCG's refers to BCG-Montreal and BCG-Toronto, the latter being derived from the former.

In performing the initial screening method, genomic DNA is isolated from two mycobacteria microbial cell cultures. The two DNA preparations are labeled, where a different label is used for the first and second microbial cultures, typically using nucleotides conjugated to a fluorochrome that emits at a wavelength substantially different from that of the fluorochrome tagged nucleotides used to label the selected probe. The strains used were the reference strain of *Mycobacterium tuberculosis* (H37Rv), other *M. tb.*laboratory strains, such as H37Ra, the O strain, *M. tb.* clinical isolates, the reference strain of *Mycobacterium bovis*, and different strains of *Mycobacterium bovis* BCG.

The two DNA preparations are mixed, and competitive hybridization is carried out to a microarray representing all of the open reading frames in the genome of the test microbe, usually H37Rv. Hybridization of the labeled sequences is accomplished according to methods well known in the art. In a preferred embodiment, the two probes are combined to provide for a competitive hybridization to a single microarray. Hybridization can be carried out under conditions varying in stringency, preferably under conditions of high stringency (e.g., 4×SSC, 10% SDS, 65° C.) to allow for hybridization of complementary sequences having extensive homology (e.g., having at least 85% sequence identity, preferably at least 90% sequence identity, more preferably having at least 95% sequence identity). Where the target sequences are native sequences the hybridization is preferably carried out under conditions that allow hybridization of only highly homologous sequences (e.g., at least 95% to 100% sequence identity).

Two color fluorescent hybridization is utilized to assay the representation of the unselected library in relation to the selected library (i.e., to detect hybridization of the unselected probe relative to the selected probe). From the ratio of one color to the other, for any particular array element, the relative abundance of that sequence in the unselected and selected libraries can be determined. In addition, comparison of the hybridization of the selected and unselected probes provides an internal control for the assay. An absence of signal from the reference strain, as compared to H37Rv, is indicative that the open reading frame is deleted in the test strain. The deletion may be further mapped by Southern blot analysis, and by sequencing the regions flanking the deletion.

Microarrays can be scanned to detect hybridization of the selected and the unselected sequences using a custom built scanning laser microscope as described in Shalon et al., *Genome Res.* 6:639 (1996). A separate scan, using the appropriate excitation line, is performed for each of the two fluorophores used. The digital images generated from the scan are then combined for subsequent analysis. For any particular array element, the ratio of the fluorescent signal from the amplified selected cell population DNA is compared to the fluorescent signal from the unselected cell population DNA, and the relative abundance of that sequence in the selected and unselected library determined.

Nucleic Acid Compositions

As used herein, the term "deletion marker", or "marker" is used to refer to those sequences of *M. tubercuosis* complex genomes that are deleted in one or more of the strains or species, as indicated in Table 1. The bacteria of the *M. tubercuosis* complex include *M. tubercuosis, M. bovis*, and BCG, inclusive of varied isolates and strains within each species. Nucleic acids of interest include all or a portion of the deleted region, particularly complete open reading frames, hybridization primers, promoter regions, etc.

The term "junction" or "deletion junction" is used to refer to nucleic acids that comprise the regions on both the 3' and the 5' sequence immediately flanking the deletion. Such junction sequences are preferably used as short primers, e.g. from about 15 nt to about 30 nt, that specifically hybridize to the junction, but not to a nucleic acid comprising the undeleted genomic sequence. For example, the deletion found in *M. bovis*, at Rv0221, corresponds to the nucleotide sequence of the *M. tuberculosis* H37Rv genome, segment 12: 17432,19335. The junction comprises the regions upstream of position 17342, and downstream of 19335, e.g. a nucleic acid of 20 nucleotides comprising the sequence from H37Rv 17332-17342 joined to 19335-19345.

Typically, such nucleic acids comprising a junction will include at least about 7 nucleotides from each flanking region, i.e. from the 3' and from the 5' sequences adjacent to the deletion, and may be about 10 nucleotides from each flanking region, up to about 15 nucleotides, or more. Amplification primers that hybridize to the junction sequence, to the deleted sequence, and to the flanking non-deleted regions have a variety of uses, as detailed below.

The nucleic acid compositions of the subject invention encode all or a part of the deletion markers. Fragments may be obtained of the DNA sequence by chemically synthesizing oligonucleotides in accordance with conventional methods, by restriction enzyme digestion, by PCR amplification, etc. For the most part, DNA fragments will be at least about 25 nt in length, usually at least about 30 nt, more usually at least about 50 nt. For use in amplification reactions, such as PCR, a pair of primers will be used. The exact composition of the primer sequences is not critical to the invention, but for most applications the primers will hybridize to the subject sequence under stringent conditions, as known in the art. It is preferable to chose a pair of primers that will generate an amplification product of at least about 50 nt, preferably at least about 100 nt. Algorithms for the selection of primer sequences are generally known, and are available in commercial software packages. Amplification primers hybridize to complementary strands of DNA, and will prime towards each other.

Usually, the DNA will be obtained substantially free of other nucleic acid sequences that do not include a deletion marker sequence or fragment thereof, generally being at least about 50%, usually at least about 90% pure and are typically "recombinant", i.e. flanked by one or more nucleotides with which it is not normally associated on a naturally occurring chromosome.

For screening purposes, hybridization probes of one or more of the deletion sequences may be used in separate reactions or spatially separated on a solid phase matrix, or labeled such that they can be distinguished from each other. Assays may utilize nucleic acids that hybridize to one or more of the described deletions.

An array may include all or a subset of the deletion markers listed in Table 1. Usually such an array will include at least 2 different deletion marker sequences, i.e. deletions located at unique positions within the locus, and may include all of the provided deletion markers. Arrays of interest may further comprise other genetic sequences, particularly other sequences of interest for tuberculosis screening. The oligonucleotide sequence on the array will usually be at least about 12 nt in length, may be the length of the provided deletion marker sequences, or may extend into the flanking regions to generate fragments of 100 to 200 nt in length. For examples of arrays, see Ramsay (1998) *Nat. Biotech.* 16:40-44; Hacia et al. (1996) *Nature Genetics* 14:441-447; Lockhart et al. (1996) *Nature Biotechnol.* 14:1675-1680; and De Risi et al. (1996) *Nature Genetics* 14:457-460.

Nucleic acids may be naturally occurring, e.g. DNA or RNA, or may be synthetic analogs, as known in the art. Such analogs may be preferred for use as probes because of superior stability under assay conditions. Modifications in the native structure, including alterations in the backbone, sugars or heterocyclic bases, have been shown to increase intracellular stability and binding affinity. Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-$CH_2$-5'-O-phosphonate and 3'-NH-5'-O-phosphoroamidate. Peptide nucleic acids replace the entire ribose phosphodiester backbone with a peptide linkage.

Sugar modifications are also used to enhance stability and affinity. The $\alpha$-anomer of deoxyribose may be used, where the base is inverted with respect to the natural $\beta$-anomer. The 2'-OH of the ribose sugar may be altered to form 2'-O-methyl or 2'-O-allyl sugars, which provide resistance to degradation without comprising affinity.

Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

Polypeptide Compositions

The specific deletion markers in Table 1 correspond to open reading frames of the *M. tb.* genome, and therefore encode a polypeptide. The subject markers may be employed for synthesis of a complete protein, or polypeptide fragments thereof, particularly fragments corresponding to functional domains; binding sites; etc.; and including fusions of the subject polypeptides to other proteins or parts thereof. For expression, an expression cassette may be employed, providing for a transcriptional and translational initiation region, which may be inducible or constitutive, where the coding region is operably linked under the transcriptional control of the transcriptional initiation region, and a transcriptional and translational termination region. Various transcriptional initiation regions may be employed that are functional in the expression host.

In the present specification and claims, the term "polypeptide fragments", or variants thereof, denotes both short peptides with a length of at least two amino acid residues and at most 10 amino acid residues, oligopeptides with a length of at least 11 amino acid residues, 20 amino acid residues, 50 amino acid residues, and up to about 100 amino acid residues; and longer peptides of greater than 100 amino acid residues up to the complete length of the native polypeptide.

The term substantially pure polypeptide fragment means a polypeptide preparation which contains at most 5% by weight of other polypeptide material with which it is natively associated, and lower percentages are preferred, e.g. at most 4%, at most 3%, at most 2%, at most 1%, and at most 0.5%. It is preferred that the substantially pure polypeptide is at least 96% pure, i.e. that the polypeptide constitutes at least 96% by weight of total polypeptide material present in the preparation, and higher percentages are preferred, such as at least 97%, at least 98%, at least 99%, at least 99.25%, at least 99.5%, and at least 99.75%. It is especially preferred that the polypeptide fragment is essentially free of any other antigen with which it is natively associated, i.e. free of any other antigen from bacteria belonging to the tuberculosis complex. This can be accomplished by preparing the polypeptide fragment by means of recombinant methods in a non-mycobacterial host, or by synthesizing the polypeptide fragment by the well-known methods of solid or liquid phase peptide synthesis, e.g. by the method described by Merrifield or variations thereof.

The *M. tuberculosis* polypeptide antigens provided herein include variants that are encoded by DNA sequences that are substantially homologous to one or more of the DNA sequences specifically recited herein, for example variants having at least 80%, 85%, 90%, 91%, 92%, 93%, 94%, 95%, 96%, 97%, 98%, 99%, or 99.5% sequence identity.

In a preferred embodiment of the invention, polypeptide fragments provide for an epitope of the deletion marker. The binding site of antibodies typically utilizes multiple non-covalent interactions to achieve high affinity binding. While a few contact residues of the antigen may be brought into close proximity to the binding pocket, other parts of the antigen molecule can also be required for maintaining a conformation that permits binding. The portion of the antigen bound by the antibody is referred to as an epitope. As used herein, an epitope is that portion of the antigen that is sufficient for high affinity binding. In a polypeptide antigen, generally a linear epitope will be at least about 7 amino acids in length, and may be at least 8, at least 9, at least 10, at least 11, at least 12, at least 14, at least 16, at least 18, at least 20, at least 22, at least 24,or at least 30 amino acid residues in length. However, antibodies may also recognize conformational determinants formed by non-contiguous residues on an antigen, and an epitope can therefore require a larger fragment of the antigen to be present for binding, e.g. a domain, or up to substantially all of a protein sequence. For each antigen there exists a plurality of epitopes that, in sum, represent the immunologic determinants of that antigen, although there are instances in which an antigen contains a single epitope.

The level of affinity of antibody binding that is considered to be "specific" will be determined in part by the class of antibody, e.g. antigen specific antibodies of the IgM class may have a lower affinity than antibodies of, for example, the IgG classes. As used herein, in order to consider an antibody interaction to be "specific", the affinity will be at least about $10^{-7}$ M, usually about $10^{-8\ to\ -9}$ M, and may be up to $10^{-11}$ or higher for the epitope of interest. It will be understood by those of skill in the art that the term "specificity" refers to such a high affinity binding, and is not intended to mean that the antibody cannot bind to other molecules as well. One may find cross-reactivity with different epitopes, due, e.g. to a relatedness of antigen sequence or structure, or to the structure of the antibody binding pocket itself. Antibodies demonstrating such cross-reactivity are still considered specific for the purposes of the present invention.

Polypeptide sequences include analogs and variants produced by recombinant methods wherein such nucleic acids and polypeptide sequences are modified by substitution, insertion, addition, and/or deletion of one or more nucleotides in the nucleic acid sequence to cause the substitution, insertion, addition, and/or deletion of one or more amino acid residues in the recombinant polypeptide.

The polypeptides may be expressed in prokaryotes or eukaryotes in accordance with conventional ways, depending upon the purpose for expression. For large scale production of the protein, a unicellular organism, such as *E. coli, B. subtilis, S. cerevisiae*, or cells of a higher organism such as vertebrates, particularly mammals, e.g. COS 7 cells, may be used as the expression host cells. Small peptides can also be synthesized in the laboratory.

With the availability of the polypeptides in large amounts, by employing an expression host, the polypeptides may be isolated and purified in accordance with conventional ways. A lysate may be prepared of the expression host and the lysate purified using HPLC, exclusion chromatography, gel electrophoresis, affinity chromatography, or other purification technique. The purified polypeptide will generally be at least about 80% pure, preferably at least about 90% pure, and may be up to and including 100% pure. Pure is intended to mean free of other proteins, as well as cellular debris.

The polypeptide is used for the production of antibodies, where short fragments provide for antibodies specific for the particular polypeptide, and larger fragments or the entire protein allow for the production of antibodies over the surface of the polypeptide. Antibodies may be raised to isolated peptides corresponding to particular domains, or to the native protein.

Antibodies are prepared in accordance with conventional ways, where the expressed polypeptide or protein is used as an immunogen, by itself or conjugated to known immunogenic carriers, e.g. KLH, pre-S HBsAg, other viral or eukaryotic proteins, or the like. Various adjuvants may be employed, with a series of injections, as appropriate. For monoclonal antibodies, after one or more booster injections, the spleen is isolated, the lymphocytes immortalized by cell fusion, and then screened for high affinity antibody binding. The immortalized cells, i.e. hybridomas, producing the desired antibodies may then be expanded. For further description, see *Monoclonal Antibodies: A Laboratory Manual*, Harlow and Lane eds., Cold Spring Harbor Laboratories, Cold Spring Harbor, N.Y., 1988. If desired, the mRNA encoding the heavy and light chains may be isolated and mutagenized by cloning in *E. coli*, and the heavy and light chains mixed to further enhance the affinity of the antibody. Alternatives to in vivo immunization as a method of raising antibodies include binding to phage "display" libraries, usually in conjunction with in vitro affinity maturation.

The antibody may be produced as a single chain, instead of the normal multimeric structure. Single chain antibodies are described in Jost et al. (1994) *J.B.C.* 269:26267-73, and others. DNA sequences encoding the variable region of the heavy chain and the variable region of the light chain are ligated to a spacer encoding at least about 4 amino acids of small neutral amino acids, including glycine and/or serine. The protein encoded by this fusion allows assembly of a functional variable region that retains the specificity and affinity of the original antibody.

Vaccines may be formulated according to methods known in the art. Vaccines of the polypeptides as described above or modified bacteria are administered to a host which may be exposed to virulent tuberculosis. In many countries where tuberculosis is endemic, vaccination may be performed at birth, with additional vaccinations as necessary. The compounds of the present invention are administered at a dosage that provides effective immunity while minimizing any side-effects. It is contemplated that the composition will be obtained and used under the guidance of a physician.

Conventional vaccine strains of BCG may be formulated in a combination vaccine with polypeptides identified in the present invention and produced as previously described, in order to improve the efficacy of the vaccine.

In one method, a dose of the deletion marker polypeptide, formulated as a cocktail of proteins or as individual protein species, in a suitable medium is injected into the patient. The dose will usually be at least about 0.05 μg of protein, and usually not more than about 5 μg of protein.

Various methods for administration may be employed. The formulation may be injected intramuscularly, intravascularly, subcutaneously, etc. The dosage will be conventional. The bacteria can be formulated into pharmaceutical compositions by combination with appropriate, pharmaceutically acceptable carriers or diluents, and may be formulated into preparations in semi-solid or liquid forms, such as solutions, injections, etc. The following methods and excipients are merely exemplary and are in no way limiting.

The polypeptide or modified bacteria can be formulated into preparations for injections by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. Unit dosage forms for injection or intravenous administration may comprise the bacteria or polypeptide of the present invention in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of vaccine, calculated in an amount sufficient to produce the desired effect in association with a pharmaceutically acceptable diluent, carrier or vehicle. The specifications for the unit dosage forms of the present invention depend on the particular bacteria employed and the effect to be achieved, and the pharmacodynamics associated with each complex in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Mycobacterium, particularly those of the *M. tubercuosis* complex, are genetically engineered to contain specific deletions or insertions corresponding to the identified genetic markers. In particular, attenuated BCG strains are modified to introduce deleted genes encoding sequences important in the establishment of effective immunity. Alternatively, *M. bovis* or *M. tubercuosis* are modified by homologous recombination to create specific deletions in sequences that determine virulence, i.e. the bacteria are attenuated through recombinant techniques.

In order to stably introduce sequences into BCG, the *M. tb.* open reading frame corresponding to one of the deletions in Table 1 is inserted into a vector that is maintained in *M. bovis* strains. Preferably, the native 5' and 3' flanking sequences are included, in order to provide for suitable regulation of transcription and translation. However, in special circumstances, exogenous promoters and other regulatory regions may be included. Vectors and methods of transfection for BCG are known in the art. For example, U.S. Pat. No. 5,776,465, herein incorporated by reference, describes the introduction of exogenous genes into BCG.

In one embodiment of the invention, the complete deleted region is replaced in BCG. The junctions of the deletion are determined as compared to a wild type *M. tb.* or *M. bovis* sequence, for example as set forth in the experimental section. The deleted region is cloned by any convenient method, as known in the art, e.g. PCR amplification of the region, restriction endonuclease digestion, chemical synthesis, etc. Preferably the cloned region will further comprise flanking sequences of a length sufficient to induce homologous recombination, usually at least about 25 nt, more usually at least about 100 nt, or greater. Suitable vectors and methods are known in the art, for an example, see Norman et al. (1995) *Mol. Microbiol.* 16:755-760.

In an alternative embodiment, one or more of the deletions provided in Table 1 are introduced into a strain of *M. tubercuosis* or *M. bovis*. Preferably such a strain is reduced in virulence, e.g. H37Ra, etc. Methods of homologous recombination in order to effect deletions in mycobacteria are known in the art, for example, see Norman et al., supra.; Ganjam et al. (1991) *P.N.A.S.* 88:5433-5437; and Aldovini et al. (1993) *J. Bacteriol.* 175:7282-7289. Deletions may comprise an open reading frame identified in Table 1, or may extend to the full deletion, i.e. extending into flanking regions, and may include multiple open reading frames.

The ability of the genetically altered mycobacterium to cause disease may be tested in one or more experimental models. For example, *M. tb.* is known to infect a variety of animals, and cells in culture. In one assay, mammalian macrophages, preferably human macrophages, are infected. In a comparison of virulent, avirulent and attenuated strains of the *M. tubercuosis* complex, alveolar or peripheral blood monocytes are infected at a 1:1 ratio (Silver et al. (1998) *Infect Immun* 66(3):1190-1199; Paul et al. (1996) *J Infect Dis* 174 (1):105-112.) The percentages of cells infected by the strains and the initial numbers of intracellular organisms are equivalent, as were levels of monocyte viability up to 7 days following infection. However, intracellular growth reflects virulence, over a period of one or more weeks. Mycobacterial growth may be evaluated by acid-fast staining, electron microscopy, and colony-forming units (cfu) assays. Monocyte production of tumor necrosis factor alpha may also be monitored as a marker for virulence.

Other assays for virulence utilize animal models. The *M. tb.* complex bacteria are able to infect a wide variety of animal hosts. One model of particular interest is cavitary tuberculosis produced in rabbits by aerosolized virulent tubercle bacilli (Converse et al. (1996) *Infect Immun* 64(11):4776-4787). In liquefied caseum, the tubercle bacilli grow extracellularly for the first time since the onset of the disease and can reach such large numbers that mutants with antimicrobial resistance may develop. From a cavity, the bacilli enter the bronchial tree and spread to other parts of the lung and also to other people. Of the commonly used laboratory animals, the rabbit is the only one in which cavitary tuberculosis can be readily produced.

Use of Deletion Markers in Identification of Mycobacteria

The deletions provided in Table 1 are useful for the identification of a mycobacterium as (a) variants of *M. tb.* (b) isolates of BCG (c) *M. bovis* strains or (d) carrying the identified mycobacterial bacteriophage, depending on the specific marker that is chosen. Such screening is particularly useful in determining whether a particular infection or isolate is pathogenic. The term mycobacteria may refer to any member of the family *Mycobacteriacaeae*, including *M. tubercuosis, M. avium* complex, *M. kansasii, M. scrofulaceum, M. bovis* and *M. leprae.*

Means of detecting deletions are known in the art. Deletions may be identified through the absence or presence of the sequences in mRNA or genomic DNA, through analysis of junctional regions that flank the deletion, or detection of the gene product, or, particularly relating to the tuberculin skin test, by identification of antibodies that react with the encoded gene product.

While deletions can be easily determined by the absence of hybridization, in many cases it is desirable to have a positive signal, in order to minimize artifactual negative readings. In such cases the deletions may be detected by designing a primer that flanks the junction formed by the deletion. Where the deletion is present, a novel sequence is formed between the flanking regions, which can be detected by hybridization. Preferably such a primer will be sufficiently short that it will only hybridize to the junction, and will fail to form stable hybrids with either of the separate parts of the junction.

Diagnosis is performed by protein, DNA or RNA sequence and/or hybridization analysis of any convenient sample, e.g. cultured mycobacteria, biopsy material, blood sample, etc. Screening may also be based on the functional or antigenic characteristics of the protein. Immunoassays designed to detect the encoded proteins from deleted sequences may be used in screening.

A number of methods are available for analyzing nucleic acids for the presence of a specific sequence. Where large amounts of DNA are available, genomic DNA is used directly. Alternatively, the region of interest is cloned into a suitable vector and grown in sufficient quantity for analysis. The nucleic acid may be amplified by conventional techniques, such as the polymerase chain reaction (PCR), to provide sufficient amounts for analysis. The use of the polymerase chain reaction is described in Saiki, et al. (1985) *Science* 239:487, and a review of current techniques may be found in Sambrook, et al. *Molecular Cloning: A Laboratory Manual*, CSH Press 1989, pp. 14.2-14.33. Amplification may also be used to determine whether a polymorphism is present, by using a primer that is specific for the polymorphism. Alternatively, various methods are known in the art that utilize oligonucleotide ligation, for examples see Riley et al. (1990) *N.A.R.* 18:2887-2890; and Delahunty et al. (1996) *Am. J. Hum. Genet.* 58:1239-1246.

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}P$, $^{35}S$, $^{3}H$; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The sample nucleic acid, e.g. amplified or cloned fragment, is analyzed by one of a number of methods known in the art. The nucleic acid may be sequenced by dideoxy or other methods, and the sequence of bases compared to the deleted sequence. Hybridization with the variant sequence may also be used to determine its presence, by Southern blots, dot blots, etc. The hybridization pattern of a control and variant sequence to an array of oligonucleotide probes immobilized on a solid support, as described in U.S. Pat. No. 5,445,934, or in WO95/35505, may also be used as a means of detecting the presence of variable sequences. Single strand conformational polymorphism (SSCP) analysis, denaturing gradient gel electrophoresis (DGGE), mismatch cleavage detection, and heteroduplex analysis in gel matrices are used to detect conformational changes created by DNA sequence variation as alterations in electrophoretic mobility. Alternatively, where a polymorphism creates or destroys a recognition site for a restriction endonuclease (restriction fragment length polymorphism, RFLP), the sample is digested with that endonuclease, and the products size fractionated to determine whether the fragment was digested. Fractionation is performed by gel or capillary electrophoresis, particularly acrylamide or agarose gels.

The hybridization pattern of a control and variant sequence to an array of oligonucleotide probes immobilized on a solid support, as described in U.S. Pat. No. 5,445,934, or in WO95/35505, may be used as a means of detecting the presence or absence of deleted sequences. In one embodiment of the invention, an array of oligonucleotides is provided, where discrete positions on the array are complementary to at least a portion of *M. th.* genomic DNA, usually comprising at least a portion from the identified open reading frames. Such an array may comprise a series of oligonucleotides, each of which can specifically hybridize to a nucleic acid, e.g. mRNA, cDNA, genomic DNA, etc.

Deletions may also be detected by amplification. In an embodiment of the invention, sequences are amplified that include a deletion junction, i.e. where the amplification primers hybridize to a junction sequence. In a nucleic acid sample where the marker sequence is deleted, a junction will be formed, and the primer will hybridize, thereby allowing amplification of a detectable sequence. In a nucleic acid sample where the marker sequence is present, the primer will not hybridize, and no amplification will take place. Alternatively, amplification primers may be chosen such that amplification of the target sequence will only take place where the marker sequence is present. The amplification products may be separated by size using any convenient method, as known in the art, including gel electrophoresis, chromatography, capillary electrophoresis, density gradient fractionation, etc.

In addition to the detection of deletions by the detection of junctions sequences, or detection of the marker sequences themselves, one may determine the presence or absence of the encoded protein product. The specific deletions in Table 1 correspond to open reading frames of the *M. tb.* genome, and therefore encode polypeptides. Polypeptides are detected by means known in the art, including determining the presence of the specific polypeptide in a sample through biochemical, functional or immunological characterization. The detection of antibodies in patient serum that react with a polypeptide is of particular interest.

Immunization with BCG typically leads to a positive response against tuberculin antigens in a skin test. In people who have been immunized, which includes a significant proportion of the world population, it is therefore difficult to determine whether a positive test is the result of an immune reaction to the BCG vaccine, or to an ongoing *M. tb.* infection. The subject invention has provided a number of open reading frame sequences that are present in *M. tb.* isolates, but are absent in BCG. As a primary or a secondary screening method, one may test for immunoreactivity of the patient with the polypeptides encoded by such deletion markers. Diagnosis may be performed by a number of methods. The different methods all determine the presence of an immune response to the polypeptide in a patient, where a positive response is indicative of an *M. tb.* infection. The immune response may be determined by determination of antibody binding, or by the presence of a response to intradermal challenge with the polypeptide.

In one method, a dose of the deletion marker polypeptide, formulated as a cocktail of proteins or as individual protein species, in a suitable medium is injected subcutaneously into the patient. The dose will usually be at least about 0.05 μg of protein, and usually not more than about 5 μg of protein. A control comprising medium alone, or an unrelated protein will be injected nearby at the same time. The site of injection is examined after a period of time for the presence of a wheal. The wheal at the site of polypeptide injection is compared to that at the site of the control injection, usually by measuring the size of the wheal. The skin test readings may be assessed by a variety of objective grading systems. A positive result for the presence of an allergic condition will show an increased diameter at the site of polypeptide injection as compared to the control, usually at least about 50% increase in size, more usually at least 100% increase in size.

An alternative method for diagnosis depends on the in vitro detection of binding between antibodies in a patient sample and the subject polypeptides, either as a cocktail or as individual protein species, where the presence of specific binding is indicative of an infection. Measuring the concentration of polypeptide specific antibodies in a sample or fraction thereof may be accomplished by a variety of specific assays. In general, the assay will measure the reactivity between a patient sample, usually blood derived, generally in the form of plasma or serum. The patient sample may be used directly, or diluted as appropriate, usually about 1:10 and usually not more than about 1:10,000. Immunoassays may be performed in any physiological buffer, e.g. PBS, normal saline, HBSS, dPBS, etc.

In a preferred embodiment, a conventional sandwich type assay is used. A sandwich assay is performed by first attaching the polypeptide to an insoluble surface or support. The polypeptide may be bound to the surface by any convenient means, depending upon the nature of the surface, either directly or through specific antibodies. The particular manner of binding is not crucial so long as it is compatible with the reagents and overall methods of the invention. They may be bound to the plates covalently or non-covalently, preferably non-covalently. Samples, fractions or aliquots thereof are then added to separately assayable supports (for example, separate wells of a microtiter plate) containing support-bound polypeptide. Preferably, a series of standards, containing known concentrations of antibodies is assayed in parallel with the samples or aliquots thereof to serve as controls.

Immune specific receptors may be labeled to facilitate direct, or indirect quantification of binding. Examples of labels which permit direct measurement of second receptor binding include radiolabels, such as $^{3}H$ or $^{125}I$, fluorescers, dyes, beads, chemilumninescers, colloidal particles, and the like. Examples of labels which permit indirect measurement of binding include enzymes where the substrate may provide for a colored or fluorescent product. In a preferred embodiment, the second receptors are antibodies labeled with a covalently bound enzyme capable of providing a detectable product signal after addition of suitable substrate. Examples of suitable enzymes for use in conjugates include horseradish peroxidase, alkaline phosphatase, malate dehydrogenase and the like. Where not commercially available, such antibody-enzyme conjugates are readily produced by techniques known to those skilled in the art.

In some cases, a competitive assay will be used. In addition to the patient sample, a competitor to the antibody is added to the reaction mix. The competitor and the antibody compete for binding to the polypeptide. Usually, the competitor molecule will be labeled and detected as previously described, where the amount of competitor binding will be proportional to the amount of Immune present. The concentration of competitor molecule will be from about 10 times the maximum anticipated Immune concentration to about equal concentration in order to make the most sensitive and linear range of detection.

Alternatively, antibodies may be used for direct determination of the presence of the deletion marker polypeptide. Antibodies specific for the subject deletion markers as previously described may be used in screening immunoassays. Samples, as used herein, include microbial cultures, biological fluids such as tracheal lavage, blood, etc. Also included in the term are derivatives and fractions of such fluids. Diagnosis may be performed by a number of methods. The different methods all determine the absence or presence of polypeptides encoded by the subject deletion markers. For example, detection may utilize staining of mycobacterial cells or histological sections, performed in accordance with conventional methods. The antibodies of interest are added to the cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Final detection uses a substrate that undergoes a color change in the presence of the peroxidase. The absence or presence of antibody binding may be determined by various methods, including microscopy, radiography, scintillation counting, etc.

An alternative method for diagnosis depends on the in vitro detection of binding between antibodies and the subject polypeptides in solution, e.g. a cell lysate. Measuring the concentration of binding in a sample or fraction thereof may be accomplished by a variety of specific assays. A conventional sandwich type assay may be used. For example, a sandwich assay may first attach specific antibodies to an insoluble surface or support. The particular manner of binding is not crucial so long as it is compatible with the reagents and overall methods of the invention. They may be bound to the plates covalently or non-covalently, preferably non-covalently. The insoluble supports may be any compositions to which polypeptides can be bound, which is readily separated from soluble material, and which is otherwise compatible with the overall method. The surface of such supports may be solid or porous and of any convenient shape. Examples of suitable insoluble supports to which the receptor is bound include beads, e.g. magnetic beads, membranes and microtiter plates. These are typically made of glass, plastic (e.g. polystyrene), polysaccharides, nylon or nitrocellulose. Microtiter plates are especially convenient because a large number of assays can be carried out simultaneously, using small amounts of reagents and samples.

Samples are then added to separately assayable supports (for example, separate wells of a microtiter plate) containing antibodies. Preferably, a series of standards, containing known concentrations of the polypeptides is assayed in parallel with the samples or aliquots thereof to serve as controls. Preferably, each sample and standard will be added to multiple wells so that mean values can be obtained for each. The incubation time should be sufficient for binding, generally, from about 0.1 to 3 hr is sufficient. After incubation, the insoluble support is generally washed of non-bound components. Generally, a dilute non-ionic detergent medium at an appropriate pH, generally 7-8, is used as a wash medium. From one to six washes may be employed, with sufficient volume to thoroughly wash non-specifically bound proteins present in the sample.

After washing, a solution containing a second antibody is applied. The antibody will bind with sufficient specificity such that it can be distinguished from other components present. The second antibodies may be labeled to facilitate direct, or indirect quantification of binding. Examples of labels that permit direct measurement of second receptor binding include radiolabels, such as $^{3}H$ or $^{125}I$, fluorescers, dyes, beads, chemilumninescers, colloidal particles, and the like. Examples of labels which permit indirect measurement of binding include enzymes where the substrate may provide for a colored or fluorescent product. In a preferred embodiment, the antibodies are labeled with a covalently bound enzyme capable of providing a detectable product signal after addition of suitable substrate. Examples of suitable enzymes for use in conjugates include horseradish peroxidase, alkaline phosphatase, malate dehydrogenase and the like. Where not commercially available, such antibody-enzyme conjugates are readily produced by techniques known to those skilled in the art. The incubation time should be sufficient for the labeled ligand to bind available molecules. Generally, from about 0.1 to 3 hr is sufficient, usually 1 hr sufficing.

After the second binding step, the insoluble support is again washed free of non-specifically bound material. The signal produced by the bound conjugate is detected by conventional means. Where an enzyme conjugate is used, an appropriate enzyme substrate is provided so a detectable product is formed.

Other immunoassays are known in the art and may find use as diagnostics. Ouchterlony plates provide a simple determination of antibody binding. Western blots may be performed on protein gels or protein spots on filters, using a detection system specific for the polypeptide, conveniently using a labeling method as described for the sandwich assay.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXPERIMENTAL

Methods:

The technical methods used begin with extraction of whole genomic DNA from bacteria grown in culture.

Day 1

Inoculate culture medium of choice (LJ/7H9) and incubate at 35° C. until abundant growth. Dispense 500 μl 1×TE into each tube. (If DNA is in liquid medium, no TE needed.) Transfer loopful (sediment) of cells into microcentrifuge tube containing 500μl of 1×TE. If taking DNA from liquid medium, let cells collect in bottom of flask. Pipette cells (about 1 ml) into tube. Heat 20 min at 80° C. to kill cells, centrifuge, resuspend in 500 μl of 1×TE. Add 50 μl of 10 mg/ml lysozyme, vortex, incubate overnight at 37° C.

Day2

Add 70 μl of 10% SDS and 10 μl proteinase K, vortex and incubate 20 min. at 65° C. Add 100 μl of 5M NaCl. Add 100 μl of CTAB/NaCl solution, prewarmed at 65° C. Vortex until liquid content white ("milky"). Incubate 10 min at 65° C. Outside of hood, prepare new microcentrifuge tubes labeled with culture # on top, and culture #, tube #, date on side. Add 550 μl isopropanol to each and cap. Back in the hood, add 750 μl of chloroform/isoamyl alcohol, vortex for 10 sec. Centrifuge at room temp for 5 min. at 12,000 g. Transfer aqueous supernatant in 180 μl amounts to new tube using pipetter, being careful to leave behind solids and non-aqueous liquid. Place 30min at −20 C. Spin 15 min at room temp in a microcentrifuge at 12,000 g. Discard supernatant; leave about 20 μl above pellet. Add 1 ml cold 70% ethanol and turn tube a few times upside down. Spin 5 min at room temp in a microcentrifuge. Discard supernatant; leave about 20 μl above the pellet. Spin 1 min in a microcentrifuge and discard cautiously the last 20 μl supernatant just above the pellet using a pipetter (P-20). Be sure that all traces of ethanol are removed. Allow pellet to dry at room temp for 10 min or speed vac 2-3 min. (Place open tubes in speed vac, close lid, start rotor, turn on vacuum. After 3 min. push red button, turn off vacuum, turn off rotor. Check if pellets are dry by flicking tube to see if pellet comes away from side of tube.) Redissolve the pellet in 20-50 μl of ddH2O. Small pellets get 20, regular sized get 30 and very large get 50. DNA can be stored at 4° C. for further use.

DNA array: was made by spotting DNA fragments onto glass microscope slides which were pretreated with poly-L-lysine. Spotting onto the array was accomplished by a robotic arrayer. The DNA was cross-linked to the glass by ultraviolet irradiation, and the free poly-L-lysine groups were blocked by treatment with 0.05% succinic anhydride, 50% 1-methyl-2-pyrrolidinone and 50% borate buffer.

The majority of spots on the array were PCR-derived products, produced by selecting over 9000 primer pairs designed to amplify the predicted open reading frames of the sequences strain H37Rv. Some internal standards and negative control spots including plasmid vectors and non-*M.tb*. DNA were also on the array.

Therefore, with the preparation for an array that contained the whole genome of *Mycobacterium tuberculosis*, we compared BCG-Connaught to *Mycobacterium tuberculosis*, using the array for competitive hybridization. The protocol follows:

DNA labeling protocol Add 4 μg DNA in 20 μl $H_2O$, 2 ml dN10N6 and 36 μl $H_2O$. 2 ml DNA spike for each DNA sample, for total of 60 μl. Boil 3 minutes to denature DNA, then snap cool on ice water bath. Add 1 μl dNTP (5 mM ACG), 10 μl 10 buffer, 4 μl Klenow, 22 μl $H_2O$ to each tube. Add 3 μl of Cy3 or Cy5 dUTP, for total of 100 μl. Incubate 3 hours at 37 C. Add 11 μl 3M NaAc, 250 μl 100% EtOH to precipitate, store O/N at −20 C. Centrifuge genomic samples 30 minutes at 13K to pellet precipitate. Discard supernatant, add 70% EtOH, spin 15 minutes, discard sup and speed-vac to dry. This provides DNA for two experiments.

DNA hybridization to microarray. protocol Resuspend the labeled DNA in 11 μl $dH_2O$ (for 2 arrays). Run out 1 μl DNA on a 1.5% agarose gel to document sample to be hybridized. Of the remaining 10 μl of solution, half will be used for this hyb, and half will be left for later date. Take 5 μl of solution Cy3 and add to same amount of Cy5 solution, for total volume 10 μl mixed labeled DNA. Add 1 μl tRNA, 2.75 μl 20×SSC, 0.4 μl SDS, for total volume 14.1 μl. Place on slide at array site, cover with 22 mm coverslip, put slide glass over and squeeze onto rubber devices, then hybridize 4 hours at 65 C. After 4 hours, remove array slides from devices, leave coverslip on, and dip in slide tray into wash buffer consisting of 1×SSC with 0.05% SDS for about 2 minutes. Cover slip should fall off into bath. After 2 minutes in wash buffer, dip once into a bath with 0.06×SSC, then rinse again in 0.06×SSC in separate bath. Dry slides in centrifuge about 600 rpm. They are now ready for scanning.

Fluorescence scanning and data acquisition. Fluorescence scanning was set for 20 microns/pixel and two readings were taken per pixel. Data for channel 1 was set to collect fluorescence from Cy3 with excitation at 520 nm and emission at 550-600 nm. Channel 2 collected signals excited at 647 nm and emitted at 660-705 nm, appropriate for Cy5. No neutral density filters were applied to the signal from either channel, and the photomultiplier tube gain was set to 5. Fine adjustments were then made to the photomultiplier gain so that signals collected from the two spots containing genomic DNA were equivalent.

To analyze the signal from each spot on the array, a 14×14 grid of boxes was applied to the data collected from the array such that signals from within each box were integrated and a value was assigned to the corresponding spot. A background value was obtained for each spot by integrating the signals measured 2 pixels outside the perimeter of the corresponding box. The signal and background values for each spot were imported into a spreadsheet program for further analysis. The background values were subtracted from the signals and a factor of 1.025 was applied to each value in channel 2 to normalize the data with respect to the signals from the genomic DNA spots.

Because the two samples are labeled with different fluorescent dyes, it is possible to determine that a spot of DNA on the array has hybridized to *Mycobacterium tuberculosis* (green dye) and not to BCG (red dye), thus demonstrating a likely deletion from the BCG genome.

However, because the array now contains spots representing 4000 spots, one may expect up to 100 spots with hybridization two standard deviations above or below the mean. Consequently, we have devised a screening protocol, where we look for mismatched hybridization in two consecutive genes on the genome. Therefore, we are essentially looking only for deletions of multiple genes at this point.

To confirm that a gene or group of genes is deleted, we perform Southern hybridization, employing a separate probe from the DNA on the array. Digestions of different mycobacterium DNAs are run on an agarose gel, and transferred to membranes. The membranes can be repeatedly used for probing for different DNA sequences. For the purposes of this project, we include DNA from the reference strain of *Mycobacterium tuberculosis* (H37Rv), from other laboratory strains, such as H37Ra, the O strain, from clinical isolates, from the reference strain of *Mycobacterium bovis*, and from different strains of *Mycobacterium bovis* BCG.

Once a deletion is confirmed by Southern hybridization, we then set out to characterize the exact genomic location. This is done by using polymerase chain reaction, with primers designed to be close to the edges of the deletion, see Talbot (1997) *J Clin Micro*. 35: 566-9

Primers have been chosen to amplify across the deleted region. Only in the absence of this region does one obtain an amplicon. PCR products were examined by electrophoresis (1.5% agarose) and ethidium bromide staining.

Once a short amplicon is obtained, this amplicon is then sequenced. A search of the genome database is performed to determine whether the sequence is exactly identical to one pad of the *Mycobacterium tuberculosis* genome, and that the next part of the amplicon is exactly identical to another part of the *Mycobacterium tuberculosis* genome. This permits precise identification of the site of deletion.

Below follows an example of the kind of report obtained:

```
rd6 bridging PCR, blast search of sequence
emb|Z79701|MTCY277 Mycobacterium tuberculosis cosmid Y277
Length = 38, 908
Plus Strand HSPs:
Score = 643 (177.7 bits), Expect = 1.6e-54, Sum P(2) = 1.6e-54
Identities = 129/131 (98%), Positives = 129/131 (98%), Strand = Plus/Plus

Query:   12 ANTAGTAATGTGCGAGCTGAGCGATGTCGCCGCTCCCAAAAATTACCAATGGTTNGGTCA 71  (SEQ ID NO:130)
            | |||||||||||||||||||||||||||||||||||||||||||||||||||| |||||
Sbjct:24784 AGTAGTAATGTGCGAGCTGAGCGATGTCGCCGCTCCCAAAAATTACCAATGGTTTGGTCA     (SEQ ID NO:131)

Query:   72 TGACGCCTTCCTAACCAGAATTGTGAATTCATACAAGCCGTAGTCGTGCAGAAGCGCAAC
            ||||||||||||||||||||||||||||||||||||||||||||||||||||||||||||
Sbjct:24844 TGACGCCTTCCTAACCAGAATTGTGAATTCATACAAGCCGTAGTCGTGCAGAAGCGCAAC

Query:  132 ACTCTTGGAGT 142
            |||||||||||
Sbjct:24904 ACTCTTGGAGT 24914

Score = 224 (61.9 bits), Expect = 1.6e-54, Sum P(2) = 1.6e-54
Identities = 46/49 (93%), Positives = 46/49 (93%), Strand = Plus/Plus

Query:  141 GTGGCCTACAACGGNGCTCTCCGNGGCGCGGGCGTACCGGATATCTTAG 189           (SEQ ID NO:132)
            | |||||||||||| |||||||| |||||||||||||||||||||||||
Sbjct:37645 GCGGCCTACAACGGCGCTCTCCGCGGCGCGGGCGTACCGGATATCTTAG 37693         (SEQ ID NO:133)
```

This process is repeated with each suggested deletion, beginning with the three previously described deletions to serve as controls. Sixteen deletions have been identified by these methods, and are listed in Table 1.

It is to be understood that this invention is not limited to the particular methodology, protocols, formulations and reagents described, as such may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "and", and "the" include plural referents unless the context clearly dictates otherwise. Thus, for example, reference to "a complex" includes a plurality of such complexes and reference to "the formulation" includes reference to one or more formulations and equivalents thereof known to those skilled in the art, and so forth.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing, for example, the cell lines, constructs, and methodologies that are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

What is claimed is:

1. An immunogenic composition, comprising:

a substantially pure polypeptide encoded by open reading frame Rv2659c, SEQ ID NO:99 or a polypeptide encoded by a nucleotide fragment of at least 25 contiguous nucleotides of SEQ ID NO:99 or where said polypeptide is fused to another peptide or protein; and a pharmaceutically acceptable excipient.

2. The immunogenic composition according to claim 1, further comprising an adjuvant.

3. The immunogenic composition according to claim 1, wherein said polypeptide is fused to another peptide or protein.

4. A method of immunizing an individual to *M. tuberculosis*, the method comprising:

injecting said individual with a mycobacterium of the *M. tuberculosis* complex that has been modified to introduce a nucleotide sequence comprising the open reading frame Rv2659c, SEQ ID NO:99 or a polypeptide encoded by a nucleotide fragment of at least 25 contiguous nucleotides of SEQ ID NO:99, wherein said mycobacterium of the *M. tuberculosis* complex is bacillus Calmette-Guerin.

5. A method of immunizing an individual to *M. tuberculosis*, the method comprising:

injecting said individual with a polypeptide encoded by open reading frame Rv2659c, SEQ ID NO:99 or a polypeptide encoded by a nucleotide fragment of at least 25 contiguous nucleotides of SEQ ID NO:99 or where said polypeptide is fused to another peptide or protein.

6. A genetically altered mycobacterium of the *M. tuberculosis* complex, comprising an exogenous nucleic acid sequence comprising the open reading frame Rv2659c, SEQ ID NO:99 or a polypeptide encoded by a nucleotide fragment of at least 25 contiguous nucleotides of SEQ ID NO:99.

7. The genetically altered mycobacterium of claim 6, wherein said exogenous nucleic acid encodes a polypeptide that is fused to another peptide or protein.

8. The genetically altered mycobacterium of claim 6, wherein said mycobacterium is BCG.

9. The mycobacterium of claim 6, and a physiologically acceptable carrier for injection.

* * * * *

SEQUENCE LISTING

<160> NUMBER OF SEQ ID NOS: 137

<210> SEQ ID NO 1
<211> LENGTH: 1773
<212> TYPE: DNA
<213> ORGANISM: Mycobacteria tuberculosis

<400> SEQUENCE: 1

```
atgactgctg aaccggaagt acggacgctg cgcgaggttg tgctggacca gctcggcact     60
gctgaatcgc gtgcgtacaa gatgtggctg ccgccgttga ccaatccggt cccgctcaac    120
gagctcatcg cccgtgatcg gcgacaaccc ctgcgatttg ccctggggat catggatgaa    180
ccgcgccgcc atctacagga tgtgtggggc gtagacgttt ccggggccgg cggcaacatc    240
ggtattgggg gcgcacctca aaccgggaag tcgacgctac tgcagacgat ggtgatgtcg    300
gccgccgcca cacactcacc gcgcaacgtt cagttctatt gcatcgacct aggtggcggc    360
gggctgatct atctcgaaaa ccttccacac gtcggtgggg tagccaatcg gtccgagccc    420
gacaaggtca accgggtggt cgcagagatg caagccgtca tgcggcaacg ggaaaccacc    480
ttcaaggaac accgagtggg ctcgatcggg atgtaccggc agctgcgtga cgatccaagt    540
caacccgttg cgtccgatcc atacggcgac gtctttctga tcatcgacgg atggcccggt    600
tttgtcggcg agttccccga ccttgagggg caggttcaag atctggccgc ccaggggctg    660
gcgttcggcg tccacgtcat catctccacg ccacgctgga cagagctgaa gtcgcgtgtt    720
cgcgactacc tcggcaccaa gatcgagttc cggcttggtg acgtcaatga aacccagatc    780
gaccggatta cccgcgagat cccggcgaat cgtccgggtc gggcagtgtc gatggaaaag    840
caccatctga tgatcggcgt gcccaggttc gacggcgtgc acagcgccga taacctggtg    900
gaggcgatca ccgcgggggt gacgcagatc gcttcccagc acaccgaaca ggcacctccg    960
gtgcgggtcc tgccggagcg tatccacctg cacgaactcg acccgaaccc gccgggacca   1020
gagtccgact accgcactcg ctgggagatt ccgatcggct tgcgcgagac ggacctgacg   1080
ccggctcact gccacatgca cacgaacccg cacctactga tcttcggtgc ggccaaatcg   1140
ggcaagacga ccattgccca cgcgatcgcg cgcgccattt gtgcccgaaa cagtccccag   1200
caggtgcggt tcatgctcgc ggactaccgc tcgggcctgc tggacgcggt gccggacacc   1260
catctgctgg gcgccggcgc gatcaaccgc aacagcgcgt cgctagacga ggccgttcaa   1320
gcactggcgg tcaacctgaa gaagcggttg ccgccgaccg acctgacgac ggcgcagcta   1380
cgctcgcgtt cgtggtggag cggatttgac gtcgtgcttc tggtcgacga ttggcacatg   1440
atcgtgggtg ccgccggggg gatgccgccg atggcaccgc tggccccgtt attgccggcg   1500
gcggcagata tcgggttgca catcattgtc acctgtcaga tgagccaggc ttacaaggca   1560
accatggaca agttcgtcgg cgccgcattc gggtcgggcg ctccgacaat gttcctttcg   1620
ggcgagaagc aggaattccc atccagtgag ttcaaggtca agcggcgccc ccctggccag   1680
gcatttctcg tctcgccaga cggcaaagag gtcatccagg ccccctacat cgagcctcca   1740
gaagaagtgt tcgcagcacc cccaagcgcc ggt                                1773
```

<210> SEQ ID NO 2
<211> LENGTH: 297
<212> TYPE: DNA
<213> ORGANISM: Mycobacteria tuberculosis

<400> SEQUENCE: 2

-continued

```
atggaaaaaa tgtcacatga tccgatcgct gccgacattg gcacgcaagt gagcgacaac      60

gctctgcacg gcgtgacggc cggctcgacg gcgctgacgt cggtgaccgg gctggttccc     120

gcgggggccg atgaggtctc cgcccaagcg gcgacggcgt tcacatcgga gggcatccaa     180

ttgctggctt ccaatgcatc ggcccaagac cagctccacc gtgcgggcga agcggtccag     240

gacgtcgccc gcacctattc gcaaatcgac gacggcgccg ccggcgtctt cgccgaa        297


<210> SEQ ID NO 3
<211> LENGTH: 1104
<212> TYPE: DNA
<213> ORGANISM: Mycobacteria tuberculosis

<400> SEQUENCE: 3

atgctgtggc acgcaatgcc accggagcta aataccgcac ggctgatggc cggcgcgggt      60

ccggctccaa tgcttgcggc ggccgcggga tggcagacgc tttcggcggc tctggacgct     120

caggccgtcg agttgaccgc gcgcctgaac tctctgggag aagcctggac tggaggtggc     180

agcgacaagg cgcttgcggc tgcaacgccg atggtggtct ggctacaaac cgcgtcaaca     240

caggccaaga cccgtgcgat gcaggcgacg gcgcaagccg cggcatacac ccaggccatg     300

gccacgacgc cgtcgctgcc ggagatcgcc gccaaccaca tcacccaggc cgtccttacg     360

gccaccaact tcttcggtat caacacgatc ccgatcgcgt tgaccgagat ggattatttc     420

atccgtatgt ggaaccaggc agccctggca atggaggtct accaggccga gaccgcggtt     480

aacacgcttt tcgagaagct cgagccgatg gcgtcgatcc ttgatcccgg cgcgagccag     540

agcacgacga acccgatctt cggaatgccc tcccctggca gctcaacacc ggttggccag     600

ttgccgccgg cggctaccca gaccctcggc caactgggtg agatgagcgg cccgatgcag     660

cagctgaccc agccgctgca gcaggtgacg tcgttgttca gccaggtggg cggcaccggc     720

ggcggcaacc cagccgacga ggaagccgcg cagatgggcc tgctcggcac cagtccgctg     780

tcgaaccatc cgctggctgg tggatcaggc cccagcgcgg gcgcgggcct gctgcgcgcg     840

gagtcgctac ctggcgcagg tgggtcgttg acccgcacgc cgctgatgtc tcagctgatc     900

gaaaagccgg ttgccccctc ggtgatgccg gcggctgctg ccggatcgtc ggcgacgggt     960

ggcgccgctc cggtgggtgc gggagcgatg ggccagggtg cgcaatccgg cggctccacc    1020

aggccgggtc tggtcgcgcc ggcaccgctc gcgcaggagc gtgaagaaga cgacgaggac    1080

gactgggacg aagaggacga ctgg                                           1104


<210> SEQ ID NO 4
<211> LENGTH: 300
<212> TYPE: DNA
<213> ORGANISM: Mycobacteria tuberculosis

<400> SEQUENCE: 4

atggcagaga tgaagaccga tgccgctacc ctcgcgcagg aggcaggtaa tttcgagcgg      60

atctccggcg acctgaaaac ccagatcgac caggtggagt cgacggcagg ttcgttgcag     120

ggccagtggc gcggcgcggc ggggacggcc gcccaggccg cggtggtgcg cttccaagaa     180

gcagccaata agcagaagca ggaactcgac gagatctcga cgaatattcg tcaggccggc     240

gtccaatact cgagggccga cgaggagcag cagcaggcgc tgtcctcgca aatgggcttc     300


<210> SEQ ID NO 5
<211> LENGTH: 285
<212> TYPE: DNA
```

-continued

<213> ORGANISM: M. tuberculosis

<400> SEQUENCE: 5

```
atgacagagc agcagtggaa tttcgcgggt atcgaggccg cggcaagcgc aatccaggga     60
aatgtcacgt ccattcattc cctccttgac gaggggaagc agtccctgac caagctcgca    120
gcggcctggg gcggtagcgg ttcggaggcg taccagggtg tccagcaaaa atgggacgcc    180
acggctaccg agctgaacaa cgcgctgcag aacctggcgc ggacgatcag cgaagccggt    240
caggcaatgg cttcgaccga aggcaacgtc actgggatgt tcgca                    285
```

<210> SEQ ID NO 6
<211> LENGTH: 1998
<212> TYPE: DNA
<213> ORGANISM: Mycobacteria tuberculosis

<400> SEQUENCE: 6

```
atggcggccg actacgacaa gctcttccgg ccgcacgaag gtatggaagc tccggacgat     60
atggcagcgc agccgttctt cgaccccagt gcttcgtttc cgccggcgcc cgcatcggca    120
aacctaccga agcccaacgg ccagactccg cccccgacgt ccgacgacct gtcggagcgg    180
ttcgtgtcgg ccccgccgcc gccacccccca cccccacctc cgcctccgcc aactccgatg    240
ccgatcgccg caggagagcc gccctcgccg gaaccggccg catctaaacc acccacaccc    300
cccatgccca tcgccggacc cgaaccggcc ccacccaaac cacccacacc ccccatgccc    360
atcgccggac ccgaaccggc cccacccaaa ccacccacac ctccgatgcc catcgccgga    420
cctgcaccca ccccaaccga atcccagttg gcgcccccca gaccaccgac accacaaacg    480
ccaaccggag cgccgcagca accggaatca ccggcgcccc acgtaccctc gcacgggcca    540
catcaacccc ggcgcaccgc accagcaccg ccctgggcaa agatgccaat cggcgaaccc    600
ccgcccgctc cgtccagacc gtctgcgtcc ccggccgaac caccgacccg gcctgccccc    660
caacactccc gacgtgcgcg ccggggtcac cgctatcgca cagacaccga acgaaacgtc    720
gggaaggtag caactggtcc atccatccag gcgcggctgc gggcagagga agcatccggc    780
gcgcagctcg cccccggaac ggagccctcg ccagcgccgt tgggccaacc gagatcgtat    840
ctggctccgc ccacccgccc cgcgccgaca gaacctcccc ccagcccctc gccgcagcgc    900
aactccggtc ggcgtgccga gcgacgcgtc caccccgatt tagccgccca acatgccgcg    960
gcgcaacctg attcaattac ggccgcaacc actggcggtc gtcgccgcaa gcgtgcagcg   1020
ccggatctcg acgcgacaca gaaatcctta aggccggcgg ccaaggggcc gaaggtgaag   1080
aaggtgaagc cccagaaacc gaaggccacg aagccgccca aagtggtgtc gcagcgcggc   1140
tggcgacatt gggtgcatgc gttgacgcga atcaacctgg gcctgtcacc cgacgagaag   1200
tacgagctgg acctgcacgc tcgagtccgc cgcaatcccc gcgggtcgta tcagatcgcc   1260
gtcgtcggtc tcaaaggtgg ggctggcaaa accacgctga cagcagcgtt ggggtcgacg   1320
ttggctcagg tgcgggccga ccggatcctg gctctagacg cggatccagg cgccggaaac   1380
ctcgccgatc gggtagggcg acaatcgggc gcgaccatcg ctgatgtgct tgcagaaaaa   1440
gagctgtcgc actacaacga catccgcgca cacactagcg tcaatgcggt caatctggaa   1500
gtgctgccgg caccggaata cagctcggcg cagcgcgcgc tcagcgacgc cgactggcat   1560
ttcatcgccg atcctgcgtc gaggttttac aacctcgtct tggctgattg tggggccggc   1620
ttcttcgacc cgctgacccg cggcgtgctg tccacggtgt ccggtgtcgt ggtcgtggca   1680
agtgtctcaa tcgacggcgc acaacaggcg tcggtcgcgt tggactggtt gcgcaacaac   1740
```

-continued

```
ggttaccaag atttggcgag ccgcgcatgc gtggtcatca atcacatcat gccgggagaa   1800
cccaatgtcg cagttaaaga cctggtgcgg catttcgaac agcaagttca acccggccgg   1860
gtcgtggtca tgccgtggga caggcacatt gcggccggaa ccgagatttc actcgacttg   1920
ctcgacccta tctacaagcg caaggtcctc gaattggccg cagcgctatc cgacgatttc   1980
gagagggctg gacgtcgt                                                 1998
```

<210> SEQ ID NO 7
<211> LENGTH: 1533
<212> TYPE: DNA
<213> ORGANISM: Mycobacteria tuberculosis

<400> SEQUENCE: 7

```
ttgagcgcac ctgctgttgc tgctggtcct accgccgcgg gggcaaccgc tgcgcggcct     60
gccaccaccc gggtgacgat cctgaccggc agacggatga ccgatttggt actgccagcg    120
gcggtgccga tggaaactta tattgacgac accgtcgcgg tgctttccga ggtgttggaa    180
gacacgccgg ctgatgtact cggcggcttc gactttaccg cgcaaggcgt gtgggcgttc    240
gctcgtcccg gatcgccgcc gctgaagctc gaccagtcac tcgatgacgc cggggtggtc    300
gacgggtcac tgctgactct ggtgtcagtc agtcgcaccg agcgctaccg accgttggtc    360
gaggatgtca tcgacgcgat cgccgtgctt gacgagtcac ctgagttcga ccgcacggca    420
ttgaatcgct ttgtgggggc ggcgatcccg cttttgaccg cgcccgtcat cgggatggcg    480
atgcgggcgt ggtgggaaac tgggcgtagc ttgtggtggc cgttggcgat tggcatcctg    540
gggatcgctg tgctggtagg cagcttcgtc gcgaacaggt tctaccagag cggccacctg    600
gccgagtgcc tactggtcac gacgtatctg ctgatcgcaa ccgccgcagc gctggccgtg    660
ccgttgccgc gcggggtcaa ctcgttgggg gcgccacaag ttgccggcgc cgctacggcc    720
gtgctgtttt tgaccttgat gacgcggggc ggccctcgga agcgtcatga gttggcgtcg    780
tttgccgtga tcaccgctat cgcggtcatc gcggccgccg ctgccttcgg ctatggatac    840
caggactggg tccccgcggg ggggatcgca ttcgggctgt tcattgtgac gaatgcggcc    900
aagctgaccg tcgcggtcgc gcggatcgcg ctgccgccga ttccggtacc cggcgaaacc    960
gtggacaacg aggagttgct cgatcccgtc gcgacccccg aggctaccag cgaagaaacc   1020
ccgacctggc aggccatcat cgcgtcggtg cccgcgtccg cggtccggct caccgagcgc   1080
agcaaactgg ccaagcaact tctgatcgga tacgtcacgt cgggcaccct gattctggct   1140
gccggtgcca tcgcggtcgt ggtgcgcggg cacttctttg tacacagcct ggtggtcgcg   1200
ggtttgatca cgaccgtctg cggatttcgc tcgcggcttt acgccgagcg ctggtgtgcg   1260
tgggcgttgc tggcggcgac ggtcgcgatt ccgacgggtc tgacggccaa actcatcatc   1320
tggtacccgc actatgcctg gctgttgttg agcgtctacc tcacggtagc cctggttgcg   1380
ctcgtggtgg tcgggtcgat ggctcacgtc cggcgcgttt caccggtcgt aaaacgaact   1440
ctggaattga tcgacggcgc catgatcgct gccatcattc ccatgctgct gtggatcacc   1500
ggggtgtacg acacggtccg caatatccgg ttc                                1533
```

<210> SEQ ID NO 8
<211> LENGTH: 840
<212> TYPE: DNA
<213> ORGANISM: Mycobacteria tuberculosis

<400> SEQUENCE: 8

-continued

```
atggctgaac cgttggccgt cgatcccacc ggcttgagcg cagcggccgc gaaattggcc     60
ggcctcgttt ttccgcagcc tccggcgccg atcgcggtca gcggaacgga ttcggtggta    120
gcagcaatca acgagaccat gccaagcatc gaatcgctgg tcagtgacgg gctgcccggc    180
gtgaaagccg ccctgactcg aacagcatcc aacatgaacg cggcggcgga cgtctatgcg    240
aagaccgatc agtcactggg aaccagtttg agccagtatg cattcggctc gtcgggcgaa    300
ggcctggctg gcgtcgcctc ggtcggtggt cagccaagtc aggctaccca gctgctgagc    360
acacccgtgt cacaggtcac gacccagctc ggcgagacgg ccgctgagct ggcaccccgt    420
gttgttgcga cggtgccgca actcgttcag ctggctccgc acgccgttca gatgtcgcaa    480
aacgcatccc ccatcgctca gacgatcagt caaaccgccc aacaggccgc ccagagcgcg    540
cagggcggca gcggcccaat gcccgcacag cttgccagcg ctgaaaaacc ggccaccgag    600
caagcggagc cggtccacga agtgacaaac gacgatcagg gcgaccaggg cgacgtgcag    660
ccggccgagg tcgttgccgc ggcacgtgac gaaggcgccg gcgcatcacc gggccagcag    720
cccggcgggg gcgttcccgc gcaagccatg gataccggag ccggtgcccg cccagcggcg    780
agtccgctgg cggccccccgt cgatccgtcg actccggcac cctcaacaac cacaacgttg    840
```

<210> SEQ ID NO 9
<211> LENGTH: 2187
<212> TYPE: DNA
<213> ORGANISM: Mycobacteria tuberculosis

<400> SEQUENCE: 9

```
atgagtatta ccaggccgac gggcagctat gccagacaga tgctggatcc gggcggctgg     60
gtggaagccg atgaagacac tttctatgac cgggcccagg aatatagcca ggttttgcaa    120
agggtcaccg atgtattgga cacctgccgc cagcagaaag gccacgtctt cgaaggcggc    180
ctatggtccg gcggcgccgc caatgctgcc aacggcgccc tgggtgcaaa catcaatcaa    240
ttgatgacgc tgcaggatta tctcgccacg gtgattacct ggcacaggca tattgccggg    300
ttgattgagc aagctaaatc cgatatcggc aataatgtgg atggcgctca acgggagatc    360
gatatcctgg agaatgaccc tagcctggat gctgatgagc gccataccgc catcaattca    420
ttggtcacgg cgacgcatgg ggccaatgtc agtctggtcg ccgagaccgc tgagcgggtg    480
ctggaatcca agaattggaa acctccgaag aacgcactcg aggatttgct tcagcagaag    540
tcgccgccac ccccagacgt gcctaccctg gtcgtgccat ccccgggcac accgggcaca    600
ccgggaaccc cgatcacccc gggaaccccg atcaccccgg gaaccccaat cacacccatc    660
ccgggagcgc cggtaactcc gatcacacca acgcccggca ctcccgtcac gccggtgacc    720
ccgggcaagc cggtcacccc ggtgaccccg gtcaaaccgg gcacaccagg cgagccaacc    780
ccgatcacgc cggtcacccc cccggtcgcc ccggccacac cggcaacccc ggccacgccc    840
gttaccccag ctcccgctcc acacccgcag ccggctccgg caccggcgcc atcgcctggg    900
ccccagccgg ttacaccggc cactcccggt ccgtctggtc cagcaacacc gggcacccca    960
gggggcgagc cggcgccgca cgtcaaaccc gcggcgttgg cggagcaacc tggtgtgccg   1020
ggccagcatg cgggcggggg gacgcagtcg gggcctgccc atgcggacga atccgccgcg   1080
tcggtgacgc cggctgcggc gtccggtgtc ccgggcgcac gggcggcggc cgccgcgccg   1140
agcggtaccg ccgtgggagc gggcgcgcgt tcgagcgtgg gtacggccgc ggcctcgggc   1200
gcggggtcgc atgctgccac tgggcgggcg ccggtggcta cctcggacaa ggcggcggca   1260
ccgagcacgc gggcggcctc ggcgcggacg gcacctcctg cccgcccgcc gtcgaccgat   1320
```

-continued

```
cacatcgaca aacccgatcg cagcgagtct gcagatgacg gtacgccggt gtcgatgatc   1380

ccggtgtcgg cggctcgggc ggcacgcgac gccgccactg cagctgccag cgcccgccag   1440

cgtggccgcg gtgatgcgct gcggttggcg cgacgcatcg cggcggcgct caacgcgtcc   1500

gacaacaacg cgggcgacta cgggttcttc tggatcaccg cggtgaccac cgacggttcc   1560

atcgtcgtgg ccaacagcta tgggctggcc tacatacccg acgggatgga attgccgaat   1620

aaggtgtact tggccagcgc ggatcacgca atcccggttg acgaaattgc acgctgtgcc   1680

acctacccgg ttttggccgt gcaagcctgg gcggctttcc acgacatgac gctgcgggcg   1740

gtgatcggta ccgcggagca gttggccagt tcggatcccg gtgtggccaa gattgtgctg   1800

gagccagatg acattccgga gagcggcaaa atgacgggcc ggtcgcggct ggaggtcgtc   1860

gacccctcgg cggcggctca gctggccgac actaccgatc agcgtttgct cgacttgttg   1920

ccgccggcgc cggtggatgt caatccaccg ggcgatgagc ggcacatgct gtggttcgag   1980

ctgatgaagc ccatgaccag caccgctacc ggccgcgagg ccgctcatct gcgggcgttc   2040

cgggcctacg ctgcccactc acaggagatt gccctgcacc aagcgcacac tgcgactgac   2100

gcggccgtcc agcgtgtggc cgtcgcggac tggctgtact ggcaatacgt caccgggttg   2160

ctcgaccggg ccctggccgc cgcatgc                                        2187
```

<210> SEQ ID NO 10
<211> LENGTH: 426
<212> TYPE: DNA
<213> ORGANISM: Mycobacteria tuberculosis

<400> SEQUENCE: 10

```
atggccggac tgaacattta cgtgaggcgc tggcggacag cgcttcacgc aaccgtgtcg     60

gcattgatag ttgccatcct cggactcgcc atcaccccgg tcgctagtgc ggcgacggcc    120

agggcgacgt tgtcggtgac atcgacgtgg cagaccggtt tcatcgcccg cttcaccatc    180

acaaactcga gcacggcgcc gctaaccgat tggaagcttg aattcgactt gccggcagga    240

gaatccgtct tgcacacatg gaatagcacc gttgcacgat ctggcacgca ctacgttctc    300

agcccagcga attggaatcg catcattgcc cccggtggtt cagccacggg cggcctaaga    360

ggcgggctga ccggttctta ctcgccgccg tcgagttgtc tgctcaacgg gcaatatcct    420

tgcacc                                                               426
```

<210> SEQ ID NO 11
<211> LENGTH: 597
<212> TYPE: DNA
<213> ORGANISM: Mycobacteria tuberculosis

<400> SEQUENCE: 11

```
gtgaactcac cactggtcgt cggcttcctg gcctgcttca cgctgatcgc cgcgattggc     60

gcgcagaacg cattcgtgct gcggcaggga atccagcgtg agcacgtgct gccggtggtg    120

gcgctgtgca cggtgtccga catcgtgctg atcgccgccg gtatcgcggg gttcggcgca    180

ttgatcggcg cacatccgcg tgcgctcaat gtcgtcaagt ttggcggcgc cgccttccta    240

atcggctacg ggctacttgc ggcccggcgg gcgtggcgac ctgttgcgct gatcccatct    300

ggcgccacgc cggttcgctt agccgaggtc ctggtgacct gtgcggcatt cacgttcctc    360

aacccacacg tctacctcga caccgtcgtg ttgctaggcg cgctggccaa cgagcacagc    420

gaccagcgct ggctgttcgg cctcggcgcg gtcacagcca gtgcggtatg gttcgccacc    480
```

-continued ctcgggttcg gagccggccg gttgcgcggg ctgttcacca accccggctc gtggagaatc 540
ctcgacggcc tgatcgcggt catgatggtt gcgctgggaa tctcgctgac cgtgacc 597

<210> SEQ ID NO 12
<211> LENGTH: 909
<212> TYPE: DNA
<213> ORGANISM: Mycobacteria tuberculosis

<400> SEQUENCE: 12
atggtggatc cgcagcttga cggtccacag ctggccgcat tggctgccgt ggtcgaactg 60
ggcagcttcg atgcggccgc ggagcgccta catgtcaccc cgtcggctgt cagtcagcgc 120
atcaagtcgt tggagcagca ggtcggccag gtgctggtgg tcagggaaaa gccatgtcgg 180
gcgacgaccg caggtatccc gctgttgcgg ttggccgcgc aaacagcgtt gctcgagtcc 240
gaggcgctcg ctgaaatggg tggcaacgcg tcgctgaaac gcacgcggat caccattgcg 300
gtaaacgccg attccatggc gacatggttt tcggccgtgt tcgacggtct cggcgacgtc 360
ctgctcgacg ttcggatcga ggaccaggac cattccgcgc ggctgctacg ggagggtgtg 420
gcgatgggcg cggtgaccac cgagcggaac ccggtgccgg gctgccgggt gcacccgctg 480
ggtgaaatgc gctacctacc agtggccagc aggccattcg tccagcgcca tctatccgac 540
gggttcactg ccgccgcggc ggctaaagct ccgtcactgg cgtggaatcg tgacgatggg 600
ctgcaggaca tgttggtgcg taaggccttt cgtcgcgcca tcaccagacc gacgcacttt 660
gtcccgacca cagagggctt caccgccgca gcgcgcgccg ggctgggatg gggcatgttc 720
cccgagaagc tggcagcatc tccgcttgcc gatggatcgt tcgtacgggt ctgcgacata 780
cacctcgacg tccctctcta ttggcaatgc tggaaactgg acagtccgat catcgcgcga 840
attaccgaca cggtgagggc ggcggcaagc ggtctgtacc ggggccagca acgccgccgc 900
cgaccgggt 909

<210> SEQ ID NO 13
<211> LENGTH: 651
<212> TYPE: DNA
<213> ORGANISM: Mycobacteria tuberculosis

<400> SEQUENCE: 13
atgactccac gcagccttgt tcgcatcgtt ggtgtcgtgg ttgcgacgac cttggcgctg 60
gtgagcgcac ccgccggcgg tcgtgccgcg catgcggatc cgtgttcgga catcgcggtc 120
gttttcgctc gcggcacgca tcaggcttct ggtcttggcg acgtcggtga ggcgttcgtc 180
gactcgctta cctcgcaagt tggcgggcgg tcgattgggg tctacgcggt gaactaccca 240
gcaagcgacg actaccgcgc gagcgcgtca aacggttccg atgatgcgag cgcccacatc 300
cagcgcaccg tcgccagctg cccgaacacc aggattgtgc ttggtggcta ttcgcagggt 360
gcgacggtca tcgatttgtc cacctcggcg atgccgcccg cggtggcaga tcatgtcgcc 420
gctgtcgccc ttttcggcga gccatccagt ggtttctcca gcatgttgtg gggcggcggg 480
tcgttgccga caatcggtcc gctgtatagc tctaagacca taaacttgtg tgctcccgac 540
gatccaatat gcaccggagg cggcaatatt atggcgcatg tttcgtatgt tcagtcgggg 600
atgacaagcc aggcggcgac attcgcggcg aacaggctcg atcacgccgg a 651

<210> SEQ ID NO 14
<211> LENGTH: 1674
<212> TYPE: DNA
<213> ORGANISM: Mycobacteria tuberculosis -continued

<400> SEQUENCE: 14
gtgtcatttc tggtcgtggt tcccgagttc ttgacgtccg cggcagcgga tgtggagaac 60
ataggttcca cactgcgcgc ggcgaatgcc gcggctgccg cctcgaccac cgcgcttgcg 120
gccgctggcg ctgatgaggt atcggcggcg gtggcagcgc tgtttgccag gttcggtcag 180
gaatatcaag cggtcagcgc gcaggcgagc gctttccatc aacagttcgt gcagacgctg 240
aactcggcgt caggatcgta tgcggccgcg gaggccacca tcgcgtcaca gttgcagacc 300
gcgcagcacg atctgctggg cgcggtcaat gcaccaaccg aaacgttgtt ggggcgtccg 360
ctaatcggcg acggagcacc cgggacggca acgagtccga atggcggggc gggtgggctg 420
ctgtacggca acggcggcaa cggttattcc gcgacggcgt cgggggtcgg cggcggggcc 480
ggcggttccg cggggttgat cggcaatggc ggcgccgggg gagccggcgg acccaacgcc 540
cccgggggag ccggcggcaa cggtggctgg ctgctcggca acggcgggat cggcgggccc 600
gggggcgcgt cgagcatccc cggcatgagt ggtggagccg gcggaaccgg cggtgccgca 660
ggacttttgg gctggggagc gaacggcgga gccggcggcc tcggtgatgg agtcggtgtc 720
gatcgtggca cgggcggcgc cggaggccgc ggcggcctgt tgtatggcgg atacggcgtc 780
agtgggccag gcggcgacgg cagaaccgtc ccgctggaga taattcatgt cacagagccg 840
acggtacatg ccaacgtcaa cggcggaccg acgtcaacca ttctggtcga caccggatcc 900
gctggtcttg ttgtctcgcc tgaggatgtc gggggaatcc tgggagtgct tcacatgggc 960
ctcccaaccg gattgagcat cagcggttac agcgggggggc tgtactacat cttcgccacg 1020
tataccacga cggtggactt cgggaatggc atcgtcaccg cgccgaccgc cgttaatgtc 1080
gtcctcttgt ccatcccaac gtccccttc gccatttcga cctacttcag cgccttgctg 1140
gccgatccga caacaactcc gttcgaagcc tatttcggtg ccgtcggcgt ggacggcgtt 1200
ctgggagttg ggcccaatgc ggtgggacca ggccccagca ttccgacgat ggcgttaccg 1260
ggtgacctca accagggagt gctcatcgac gcacccgcag gtgagctcgt gttcggtccc 1320
aacccgctac ctgcgcccaa cgtcgaggtc gtcggatcgc cgatcaccac cctgtacgta 1380
aagatcgatg gtgggactcc catacccgtc ccctcgatca tcgattccgg tggggtaacg 1440
ggaaccatcc cgtcatatgt catcggatcc ggaaccctgc cggcgaacac aaacattgag 1500
gtctacacca gccccggcgg tgatcggctc tacgcgttca acacaaacga ttaccgcccg 1560
accgtcattt catccggcct gatgaatacc gggttcttgc ccttcagatt ccagccggtg 1620
tacatcgact acagccccag cggtataggg acaacagtct ttgatcatcc ggcg 1674

<210> SEQ ID NO 15
<211> LENGTH: 1674
<212> TYPE: DNA
<213> ORGANISM: M. tuberculosis

<400> SEQUENCE: 15
gtgtcatttc tggtcgtggt tcccgagttc ttgacgtccg cggcagcgga tgtggagaac 60
ataggttcca cactgcgcgc ggcgaatgcc gcggctgccg cctcgaccac cgcgcttgcg 120
gccgctggcg ctgatgaggt atcggcggcg gtggcagcgc tgtttgccag gttcggtcag 180
gaatatcaag cggtcagcgc gcaggcgagc gctttccatc aacagttcgt gcagacgctg 240
aactcggcgt caggatcgta tgcggccgcg gaggccacca tcgcgtcaca gttgcagacc 300
gcgcagcacg atctgctggg cgcggtcaat gcaccaaccg aaacgttgtt ggggcgtccg 360

-continued

```
ctaatcggcg acggagcacc cgggacggca acgagtccga atggcggggc gggtgggctg    420
ctgtacggca acggcggcaa cggttattcc gcgacggcgt cgggggtcgg cggcggggcc    480
ggcggttccg cggggttgat cggcaatggc ggcgccgggg gagccggcgg acccaacgcc    540
cccgggggag ccggcggcaa cggtggctgg ctgctcggca acggcgggat cggcgggccc    600
gggggcgcgt cgagcatccc cggcatgagt ggtggagccg gcggaaccgg cggtgccgca    660
ggacttttgg gctggggagc gaacggcgga gccggcggcc tcggtgatgg agtcggtgtc    720
gatcgtggca cgggcggcgc cggaggccgc ggcggcctgt tgtatggcgg atacggcgtc    780
agtgggccag gcggcgacgg cagaaccgtc ccgctggaga taattcatgt cacagagccg    840
acggtacatg ccaacgtcaa cggcggaccg acgtcaacca ttctggtcga caccggatcc    900
gctggtcttg ttgtctcgcc tgaggatgtc gggggaatcc tgggagtgct tcacatgggc    960
ctcccaaccg gattgagcat cagcggttac agcgggggc tgtactacat cttcgccacg   1020
tataccacga cggtggactt cgggaatggc atcgtcaccg cgccgaccgc cgttaatgtc   1080
gtcctcttgt ccatcccaac gtccccttc gccatttcga cctacttcag cgccttgctg   1140
gccgatccga caacaactcc gttcgaagcc tatttcggtg ccgtcggcgt ggacggcgtt   1200
ctgggagttg ggcccaatgc ggtgggacca ggccccagca ttccgacgat ggcgttaccg   1260
ggtgacctca accagggagt gctcatcgac gcacccgcag gtgagctcgt gttcggtccc   1320
aacccgctac ctgcgcccaa cgtcgaggtc gtcggatcgc cgatcaccac cctgtacgta   1380
aagatcgatg gtgggactcc catacccgtc ccctcgatca tcgattccgg tggggtaacg   1440
ggaaccatcc cgtcatatgt catcggatcc ggaaccctgc cggcgaacac aaacattgag   1500
gtctacacca gccccggcgg tgatcggctc tacgcgttca acacaaacga ttaccgcccg   1560
accgtcattt catccggcct gatgaatacc gggttcttgc ccttcagatt ccagccggtg   1620
tacatcgact acagccccag cggtataggg acaacagtct ttgatcatcc ggcg          1674
```

```
<210> SEQ ID NO 16
<211> LENGTH: 417
<212> TYPE: DNA
<213> ORGANISM: Mycobacteria tuberculosis

<400> SEQUENCE: 16
atgatcgtgg acacaagcgc cgtggtggcc ctggttcaag gcgagcggcc gcacgccacc     60
ctggtcgcgg ccgccctggc cggcgcccat agccccgtca tgtctgcacc caccgtcgcc    120
gaatgcctga ttgtcttgac cgcccgtcac ggccccgttg cgcgcacgat cttcgaacga    180
cttcgcagcg aaatcggctt gagcgtgtca tctttcaccg ccgagcatgc cgctgccacg    240
caacgagcct ttctgcgata cggcaagggg cgccaccgcg cggctctcaa cttcggagac    300
tgtatgacgt acgcgaccgc ccagctgggc caccaaccac tgctggccgt cggcaacgac    360
ttcccgcaaa ccgaccttga gttccgcggc gtcgtcggct actggccagg cgtcgcg        417
```

```
<210> SEQ ID NO 17
<211> LENGTH: 684
<212> TYPE: DNA
<213> ORGANISM: M. tuberculosis

<400> SEQUENCE: 17
gtgcgcatca agatcttcat gctggtcacg gctgtcgttt tgctctgttg ttcgggtgtg     60
gccacggccg cgcccaagac ctactgcgag gagttgaaag gcaccgatac cggccaggcg    120
tgccagattc aaatgtccga cccggcctac aacatcaaca tcagcctgcc cagttactac    180
```

-continued cccgaccaga agtcgctgga aaattacatc gcccagacgc gcgacaagtt cctcagcgcg 240
gccacatcgt ccactccacg cgaagccccc tacgaattga atatcacctc ggccacatac 300
cagtccgcga taccgccgcg tggtacgcag gccgtggtgc tcaaggtcta ccagaacgcc 360
ggcggcacgc acccaacgac cacgtacaag gccttcgatt gggaccaggc ctatcgcaag 420
ccaatcacct atgacacgct gtggcaggct gacaccgatc cgctgccagt cgtcttcccc 480
attgtgcaag gtgaactgag caagcagacc ggacaacagg tatcgatagc gccgaatgcc 540
ggcttggacc cggtgaatta tcagaacttc gcagtcacga acgacggggt gattttcttc 600
ttcaacccgg gggagttgct gcccgaagca gccggcccaa cccaggtatt ggtcccacgt 660
tccgcgatcg actcgatgct ggcc 684

<210> SEQ ID NO 18
<211> LENGTH: 684
<212> TYPE: DNA
<213> ORGANISM: M. tuberculosis

<400> SEQUENCE: 18
gtgcgcatca agatcttcat gctggtcacg gctgtcgttt tgctctgttg ttcgggtgtg 60
gccacggccg cgcccaagac ctactgcgag gagttgaaag gcaccgatac cggccaggcg 120
tgccagattc aaatgtccga cccggcctac aacatcaaca tcagcctgcc cagttactac 180
cccgaccaga agtcgctgga aaattacatc gcccagacgc gcgacaagtt cctcagcgcg 240
gccacatcgt ccactccacg cgaagccccc tacgaattga atatcacctc ggccacatac 300
cagtccgcga taccgccgcg tggtacgcag gccgtggtgc tcaaggtcta ccagaacgcc 360
ggcggcacgc acccaacgac cacgtacaag gccttcgatt gggaccaggc ctatcgcaag 420
ccaatcacct atgacacgct gtggcaggct gacaccgatc cgctgccagt cgtcttcccc 480
attgtgcaag gtgaactgag caagcagacc ggacaacagg tatcgatagc gccgaatgcc 540
ggcttggacc cggtgaatta tcagaacttc gcagtcacga acgacggggt gattttcttc 600
ttcaacccgg gggagttgct gcccgaagca gccggcccaa cccaggtatt ggtcccacgt 660
tccgcgatcg actcgatgct ggcc 684

<210> SEQ ID NO 19
<211> LENGTH: 1443
<212> TYPE: DNA
<213> ORGANISM: Mycobacteria tuberculosis

<400> SEQUENCE: 19
gtggtcggcc cgcggacgag aggatatgcg atccacaagc tgggtttctg cagcgtcgtc 60
atgctcggga tcaactcgat aatcggcgcc ggtatcttcc taactccagg tgaggtgatc 120
gggctcgcag gacccttcgc gccgatggcc tatgttttag ctggcatttt cgcgggtgtc 180
gtggcgatcg tcttcgcgac ggcggcaagg tacgtcagaa caaacggtgc ctcctacgcc 240
tacacaacgg ccgcatttgg gcgccggatc ggcatctatg tcggtgtcac ccacgccatt 300
accgcgtcca tcgcttgggg ggtgttggct tcttttttcg tctcgacgct gttgcgagtg 360
gccttccccg acaaggcctg ggccgacgcc gagcaactgt tcagtgtgaa gacgctgacg 420
tttctcggct ttatcggcgt gctgttggcc atcaacctct tcggcaaccg ggcgatcaag 480
tgggccaacg gaacgtcaac ggtaggcaag gcattcgcgc tctcggcatt cattgtcggc 540
gggctgtgga tcatcaccac ccagcacgtg aacaactacg caacggcgtg gtcggcatac 600

| | |
|---|---:|
| agcgcgaccc cgtactcgtt gcttggcgtc gccgaaattg gcaagggcac gttctcgagt | 660 |
| atggcgctgg ccacgattgt cgcgttgtac gcattcaccg gtttcgaatc gatcgcgaac | 720 |
| gccgccaag aaatggacgc gccggaccgg aacctgccga gagctatacc gatcgcgatc | 780 |
| ttctcggttg gcgcgatcta cttgctcacc ctaacggtag cgatgctgct cggatcgaac | 840 |
| aagatcgccg cgtcggacga caccgtgaaa ctggccgcgg ccatcggaaa cgctaccttc | 900 |
| cgaacgatca tcgtcgtcgg agccctgata tcgatgttcg gcatcaatgt cgcggcctcg | 960 |
| ttcggtgcac cgcggctttg gaccgcgtta gcggacagcg gggttctgcc gacacgcttg | 1020 |
| tcacgcaaga accaatacga cgtgccgatg gtctccttcg caattacggc gtcgttggcg | 1080 |
| ctcgcattcc cgttggcgct gcggttcgac aacctgcacc tgaccggcct ggcggtgatc | 1140 |
| gcccgattcg tccagttcat catcgtgccg atcgctctca tcgcattggc gaggtctcag | 1200 |
| gcagtagaac atgctgctgt gcggcgaaat gcgttcaccg acaaggtgtt accgcttgtt | 1260 |
| gcgatcgtgg tctcggttgg gctggcagtg tcctacgact accgctgcat ctttctagtg | 1320 |
| cggggtggtc cgaactactt ctcgattgct ttgatcgtga tcacgttcgt cgtggtaccg | 1380 |
| gcgatggctt atctgcacta ctaccgaatc attcgccggg ttggcgatcg gccgagcact | 1440 |
| cgc | 1443 |

<210> SEQ ID NO 20
<211> LENGTH: 846
<212> TYPE: DNA
<213> ORGANISM: Mycobacteria tuberculosis

<400> SEQUENCE: 20

| | |
|---|---:|
| atgggtgagg cgaacatccg cgagcaggcg atcgccacga tgccacgggg tggccccgac | 60 |
| gcgtcttggc tggatcgtcg attccagacc gacgcactgg agtacctcga ccgcgacgat | 120 |
| gtgcccgatg aggtcaaaca gaagatcatc ggggtgctcg accgggtggg caccctgacc | 180 |
| aacctgcacg agaagtacgc ccggatagcc ctgaaacttg tttctgacat tcccaacccg | 240 |
| cgaatcctgg aacttggtgc gggccatggc aagctctcag cgaaaatcct cgagctacac | 300 |
| ccgacagcga cggtgacgat cagcgatcta gatcccacct cggtggccaa catcgccgcg | 360 |
| ggagagctgg gaacacatcc gcgagcacgc acccaagtga tcgacgccac cgcaatcgac | 420 |
| ggccacgacc acagctatga cctggcggtc ttcgcgctgg catttcacca cctgccgcct | 480 |
| acggtcgcct gcaaagcgat cgccgaggcc acccgggtgg ggaagcgctt tctgatcatc | 540 |
| gacctcaaac ggcagaaacc gctgtcgttc acgctctctt cggtgctgct actgccgctc | 600 |
| cacctactgc tgctgccatg gtcgtcgatg cgctcgagca tgcacgacgg ctttatcagc | 660 |
| gcactacgtg cctacagtcc ctcggcgttg cagacgcttg cccgcgccgc cgatccggga | 720 |
| atgcaggttg aaatcttgcc cgcaccgacc aggctattcc cgccatcgct cgccgttgtg | 780 |
| ttctcccgtt cgagctcagc gccaacggaa tctagcgagt gctcggccga tcgccaaccc | 840 |
| ggcgaa | 846 |

<210> SEQ ID NO 21
<211> LENGTH: 1407
<212> TYPE: DNA
<213> ORGANISM: Mycobacteria tuberculosis

<400> SEQUENCE: 21

| | |
|---|---:|
| gtgagataca ctacacctgt gcgtgctgct gtctacctcc gaatctcaga agaccgctcc | 60 |
| ggcgaacagc tcggcgtggc ccgccaacgc gaggactgcc taaagctgtg cgggcagcga | 120 |

-continued aaatgggtgc ccgtcgagta cctcgacaac gacgtcagcg catcaaccgg caagcgccgc 180
cccgcctacg agcagatgtt ggccgacatc accgccggca agatcgccgc cgtggtggcc 240
tgggacctgg accggctcca tcgccgtccc atcgagctgg aagccttcat gtcattagcc 300
gacgagaagc ggctggccct ggccaccgtc gccggcgacg ttgacctggc gacaccccag 360
ggccggctag tcgcccgcct gaaggggtcg gtggccgctc acgaaaccga gcacaagaag 420
gcacgacagc gccgcgccgc ccgccagaaa gctgaacgcg gccaccccaa ctggtcgaaa 480
gccttcggct acctgcccgg ccccaacggt cccgaacccg acccccggac agcgccgctg 540
gtcaaacagg cctacgccga catcctcgcc ggggcgtccc tgggcgacgt gtgccgccag 600
tggaacgacg ccggggcgtt caccatcacc ggccgcccgt ggacgactac aacgctgtcg 660
aaattcttgc gcaaaccccg caacgccgga ctacgcgcat ataagggtgc ccgctacggc 720
ccggtggacc gcgacgcgat tgtcggcaag gcccagtggt cgccgctggt ggacgaggcg 780
acgttctggg ccgcccaggc cgtgctggac gcccccggcc gcgcccccgg ccgcaaaagc 840
gtgcgccgcc acctgctgac cgggctggca ggctgcggca aatgcggcaa ccacctggcc 900
ggcagctacc gcaccgacgg ccaggtcgtc tacgtgtgca aggcgtgcca cggggtggcc 960
atcctggccg acaacatcga accgatcctg tatcacatcg tggccgagcg gctggccatg 1020
cccgacgccg ttgacttgtt gcgccgggag attcacgacg ccgccgaagc cgaaaccatc 1080
cgcctggaac tggaaaccct ctacggggag ctggacaggc tcgccgtcga acgcgccgaa 1140
gggctactga ccgcgcgcca ggtgaagatc agcaccgaca tcgtcaacgc caagataacg 1200
aaacttcagg cccgccaaca ggatcaggaa cggctccgag tgttcgacgg gataccgttg 1260
ggaacaccgc aagtcgccgg gatgatagcc gagctgtcgc cggaccggtt ccgcgccgtc 1320
ctcgacgtcc tcgctgaagt cgttgtccag ccggtcggca agagcggcag gatattcaat 1380
cccgaacggg tgcaggtgaa ttggcga 1407

<210> SEQ ID NO 22
<211> LENGTH: 513
<212> TYPE: DNA
<213> ORGANISM: M. tuberculosis

<400> SEQUENCE: 22
atgagccggc accacaacat cgtgatcgtc tgtgaccacg gccgcaaagg cgatggccgc 60
atcgaacacg agcgctgcga tcttgtcgcg ccgatcattt gggtcgacga gacccagggc 120
tggttaccgc aggcgccagc ggtggcaaca ttactcgacg acgacaacca gccgcgagcc 180
gttattggct tgccgcccaa cgagtctcgc ctacgacctg aaatgcgccg cgacgggtgg 240
gtgcggctgc actgggaatt cgcctgcctg aggtacggcg ccgccggcgt gcgcacgtgc 300
gagcagcggc ccgtgcgggt tcgcaacggc gacctgcaaa cactgtgcga gaacgttccg 360
cggctactga ccggactggc cggcaacccc gactacgcac cgggttttgc ggtgcagtcg 420
gacgcggtgg tcgtcgccat gtggctgtgg cgcacgctct gcgaaagcga cacgccgaac 480
aaactacgcg ccaccccaac gcgtggtagc tgc 513

<210> SEQ ID NO 23
<211> LENGTH: 219
<212> TYPE: DNA
<213> ORGANISM: M. tuberculosis

<400> SEQUENCE: 23

-continued

```
gtgtcgacca tctaccatca tcgcggccgc gtagccgcac tgtctcgttc ccgcgcatcc     60

gacgatcccg agttcatcgc cgcgaaaacc gatctcgttg ccgcgaacat cgcggactac    120

ctcatccgca ccctcgccgc agcgccgccc ctgactgacg agcagcgcac ccggctggcc    180

gagctgctgc gccccgtgcg gcggtcaggc ggtgcccga                           219
```

<210> SEQ ID NO 24
<211> LENGTH: 396
<212> TYPE: DNA
<213> ORGANISM: Mycobacteria tuberculosis

<400> SEQUENCE: 24

```
atgaccgccg gcgccggcgg gtcgccgccg acgcgacgat gcccggccac ggaggaccgg     60

gcacccgcga cagtcgccac accgtctagc gccgatccta ccgcgtcacg cgccgtgtcg    120

tggtggtcgg tgcacgagca tgtcgcgccg gtcctggatg ctgccgggtc gtggccgatg    180

gccggcacac cggcctggcg tcagctcgac gacgccgatc ctcgcaaatg ggccgcgatc    240

tgcgacgcag cccggcactg ggctctgagg gtagagacgt gccaggaggc gatggcgcag    300

gcgtcacgtg acgtatctgc ggccgccgac tggcccggca tcgcccgcga gatcgtccga    360

cggcgcggcg tgtacatccc gcgggcgggg gtggcg                              396
```

<210> SEQ ID NO 25
<211> LENGTH: 1413
<212> TYPE: DNA
<213> ORGANISM: Mycobacteria tuberculosis

<400> SEQUENCE: 25

```
atggccgaca tcccctacgg caccgactat cccgacgccc cctggatcga ccgggacggg     60

cacgtgctca tcgacgacgg tggcaaaccg acgcaagttc atcgcggcca agcccgaatc    120

gcctaccggc tagccgaacg ttaccaggac aagctgctgc acgtggccgg gatcggctgg    180

cactcctggg acggcagacg ctgggcagcc gacgaccgcg gcgaagccaa acgtgcagtg    240

ctggcagagc tgcgccaagc gctctcagac agcctcaacg acaaggaatt acgcgccgac    300

gtccgaaaat gcgaatcggc gtccggcgtg gccggcgtgc tcgacctggc cgccgcactg    360

gtaccattcg ccgcgacggt agccgacctc gacagcgacc cgcacttgct caacgtcgcg    420

aatgggacgc tggacctgca cacgctcaaa ttgcggcccc acgcgcccgc tgaccgcatc    480

acaaagatat gccgcggtgc ctaccagtcc gacaccgaat cgcctctctg gcaagcgttc    540

ttgacccgcg ttctgcccga tgaaggtgtg cgcgggttcg tgcaacgcct ggccggcgtc    600

ggcctactag gcaccgtccg cgaacatgtc ctggcgattc ttatcggtgt aggtgccaac    660

ggaaaatctg tgttcgacaa ggcgattcgc tatgcccttg gcgattatgc ctgcaccgct    720

gagcctgacc ttttcatgca ccgggaaaac gctcacccaa caggcgaaat ggacctccgc    780

ggcgtgcgat gggtagcggt atccgagagc gaaaaagatc gccggctggc cgaatcaacg    840

ataaaacggc tgactggcgg cgacaccatc cgcgcccgaa agatgcggca agacttcgtg    900

gaattcacgc cgtcacatac ccccactgctc atcaccaacc acctaccgag agtgcccggc    960

gatgatacgg ccatctggcg gcgaattcga gtggtgccgt ttgaagtagt gattcctgcc   1020

gacgagcagg accgggaact ggacgcacgg ttgcagttgg aggccgacag catcctgtcc   1080

tgggcggtgg ccggatggag cgactatcag cgaatcggac tatcccagcc ggacgcggtg   1140

ctcgcggcaa cgtcgaatta ccgcgaggac tccgacacga taaagaggtt catcgacgac   1200

gaatgcgtca ccagctcgcc ggtgctgaaa gccactacta cgcatctgtt cgaggcgtgg   1260
```

-continued caaaggtggc gggtgcaaga aggcgtaccc gaaatctcgc gcaaagcgtt cggccagtcg 1320
ctcgacaccc acggataccc ggtcactgac aaggcccgtg atggtcgttg gcgggccgga 1380
atagcggtga gaggggccga tgatttcgat gat 1413

<210> SEQ ID NO 26
<211> LENGTH: 393
<212> TYPE: DNA
<213> ORGANISM: Mycobacteria tuberculosis

<400> SEQUENCE: 26
atgaccgctg tcgcgatcac cccggcatcc ggcggtcggc acagcgtccg attcgcctac 60
gactctgcga tcgtgtcgtt gatcaagtcc acgatccccg cctatgcccg ctcctggtcc 120
gcgcacaccc gctgctggtt catcgacgct gactggaccc cactgctggc cgccgagctg 180
cgctaccacg gccacaccgt caccggaccc gccgacccgg cgcaacagca gtgcaccgac 240
tgggccaaag cgttgttccg ggcggtcgga ccccagcgga cacccgccgt gtacagggct 300
ttatccaaag tgctgcaccc cgacgcccca accggatgcc cgatactgca acagcagctc 360
aatgccgcca gaaccgcact taccaaccct gct 393

<210> SEQ ID NO 27
<211> LENGTH: 270
<212> TYPE: DNA
<213> ORGANISM: Mycobacteria tuberculosis

<400> SEQUENCE: 27
atggctgaaa cccccgacca cgccgaactg cggcgacgaa tcgccgacat ggctttcaac 60
gccgatgtcg gtatggcgac ctgcaaacgc tgtggtgacg ccgtgccgta catcatcctg 120
ccgaacctgc agaccggcga acccgtcatg ggtgtcgccg acaacaaatg gaagcgcgcg 180
aactgtcccg tcgacgtcgg taagccgtgc ccgttcctaa tcgccgaggg tgtcgccgac 240
agcaccgacg acaccataga ggtcgaccag 270

<210> SEQ ID NO 28
<211> LENGTH: 312
<212> TYPE: DNA
<213> ORGANISM: Mycobacteria tuberculosis

<400> SEQUENCE: 28
gtgaccccga tcaaccggcc cctgaccaac gacgaacgac aactgatgca cgagctggca 60
gtccaggttg tctgctcgca gacgggttgc tcacccgatg cggcggtcga agcactcgaa 120
tccttcgcga aagacggaac acttatcctc cgcggcgaca ccgagaacgc ctacctcgaa 180
gccggaggca atgttcttgt ccatgccgat cgtgactggc ttgccttcca cgcgtcgtat 240
cccggcaacg acccgctgcg agacgcccga cctatcgagc aggacgacga ccagggggcg 300
gggtcgccat cg 312

<210> SEQ ID NO 29
<211> LENGTH: 468
<212> TYPE: DNA
<213> ORGANISM: Mycobacteria tuberculosis

<400> SEQUENCE: 29
atgccaagac caccgaaacc ggcccggctc aaactggttg agggccgctc ccccggccgc 60
gattccggcg gccggaaagt ccccgagtcg ccgaagttta tccgtcaggc accggatgcc 120

-continued

```
ccggactggc tcgacgccga ggcgctggcc gaatggcggc gcgtcgcacc gactttggag    180

cggcttgacc tgctcaaacc tgaggatcgg gcgctcctgt ccgcgtactg cgagacctgg    240

tccgtctacg tcgcggcggt tcagcgggtc cgcgccgaag gcctcacaat tacctcaccg    300

aaatccggtg tcgtgcaccg gaacccggcg gtgacggttg cggagacggc gcgcatgcat    360

ctgctgcgct tggcctccga gtttggcctg accccggccg ccgagcagcg actggcggtg    420

gcgccgggcg acgacggcga cgggctcaac ccgtttgccc cggaccgg                 468
```

```
<210> SEQ ID NO 30
<211> LENGTH: 510
<212> TYPE: DNA
<213> ORGANISM: Mycobacteria tuberculosis

<400> SEQUENCE: 30

atggccgagc tgcggtctgg cgaaggccga accgtgcacg gcaccatcgt gccctacaac     60

gaggcgacca ccgtccgcga cttcgacggc gagttccagg aaatgttcgc tcctggcgct    120

tttcggcgct ccatcgccga gcgcggccac aaattgaagc tgctggtctc tcacgacgct    180

cgaacccgct acccggtggg ccgggccgtt gagttgcggg aggagcctca cggcttgttc    240

ggggcgttcg agattgcgga caccccggac ggcgacgagg ctttggcgaa cgtaaaagct    300

ggtgtcgtcg actcgttttc ggtgggtttc cgaccgatcc gggaccgtcg cgaaggggat    360

gtgctggtgc gcgtcgaagc ggcgctgtta gaggtttccc taaccggcgt tccggcctat    420

tcgggggcac aaatcgccgg ggtgcgcgcg gaatcgctta cagtcgtttc ccgttcgaca    480

gccgaagcct ggctgtccct actcgattgg                                     510
```

```
<210> SEQ ID NO 31
<211> LENGTH: 1419
<212> TYPE: DNA
<213> ORGANISM: Mycobacteria tuberculosis

<400> SEQUENCE: 31

atgaccgaat tcgacgacat caaaaacctc tctttacctg aaacccgtga cgcggcgaag     60

cagctcctcg acagtgtcgc cggcgacctg accggtgagg cggcgcagcg ttttcaggcg    120

ctgacgcgcc acgccgagga actgcgggcg gagcagcgcc gccgcggccg cgaagccgag    180

gaggcgctgc gccgctaccg ggccggtgag ctgagggtgg tgcccggcgc tcccaccggc    240

ggcgacgacg gcgacgcgcc gccgggcaac tcgttgcggg acaccgcgtt tcgcacactg    300

gattcttgtg tgcgagacgg cctgatgtcg tcgcgggcgg cggagaccgc ggaaaccttg    360

tgccgcaccg ggccgccgca gtccacctcg tgggcgcagc gctggctggc ggccaccggc    420

agccgcgact atttgggcgc gttcgtcaag cgggtttcca atcctgttgc ggggcacacg    480

gtttggaccg accgggaagc ggccgcgtgg cgtgaggctg ccgcggtggc cgccgagcag    540

cgagcgatgg gcctggtgga cacccaaggc gggtttctga tcccggcggc gctggacccg    600

gcgatcctgc tgtcgggtga tgggtcgacg aacccgattc ggcaggtggc gagggtggtg    660

caaacgacct ccgagatttg gcggggcgtg acttccgaag gcgccgaagc tcgttggtac    720

tccgaagccc aggaggtgtc cgacgattcg ccagcgttgg cccagccggc ggtgccgaac    780

taccgtggaa gctgctggat tccgttctcc atcgagctgg agggtgacgc ggcgagcttc    840

gttggcgaga tcggcaagat tctcgcggac agcgttgagc aactgcaggc cgcggcgttc    900

gtcaacggct ccggcaacgg cgagcccacc gggttcgtca gcgcgctaac cggcacctcc    960

gatcaggtgg tcgtcggcgc ggggtcagaa gcgattgtgg cggcggatgt ttacgcgttg   1020
```

-continued

```
cagtcggcgc tgccgccaag gttccaggcc agcgccgcgt tcgcggcgaa cttgtccacc   1080

atcaacacgt tgcggcaggc ggaaacttcg aatggcgcgc tgaaattccc atcgctgcac   1140

gacagtccgc cgatgctagc cgggaagtct gtcctggaag tctcccacat ggacaccgtt   1200

gattcggcgg tgacagcgac gaatcatcca ctggtgcttg gcgactggaa gcaattcctc   1260

atcggcgaca gagttgggtc catggtggag ttggtgcctc acctgttcgg gccgaatcgc   1320

cggccgaccg ggcagcgcgg attcttcgcc tggttcaggg tcggatcaga tgtgctggtg   1380

cgcaacgcgt ttcgagttct gaaggtggag actaccgcg                          1419
```

```
<210> SEQ ID NO 32
<211> LENGTH: 351
<212> TYPE: DNA
<213> ORGANISM: Mycobacteria tuberculosis

<400> SEQUENCE: 32

atggcgccgc tggccgccgg atcgccgagc tggaacggcc gaaagccaag cagcggcaac     60

aggaaggcgg cgaccatggc cgccaggctc gatattctgg cttggggccc atgggcccca    120

agccagaatc ggagcgtcgt tcgacgaaaa cagacactgc tatcggcgca gccctcggca    180

tctccgccgg cacctaccgg cggctcaaac gaatcgacaa cgcaacccgc agcgagttgg    240

cgcgtgggcg gcccggcacc cctaagcaga ggccgcccac gcctggccct atcctaccta    300

cgcggtagtc tccaccttca gaactcgaaa cgcgttgcgc accagcacat c             351
```

```
<210> SEQ ID NO 33
<211> LENGTH: 309
<212> TYPE: DNA
<213> ORGANISM: Mycobacteria tuburculosis

<400> SEQUENCE: 33

atgggctaca aaccagaatc agagcgtcat tcgacgaaaa cagacactgc tatcggcgca     60

gccctcggca tctccgccgg cacctaccgg cggctcaaac gaatcgacaa cgcaacccac    120

agcgacgaca aagaaatccg ccggttcgcg gagaaacaaa tggcgccgct ggtcgccgga    180

tcgccgagct ggaacgcccg aaagccaagg agcgccaacg cgagggtggt cgcctcggtg    240

catcgatcac caatgccggc tttggtccca tggaaccaaa gccgtctcag cgccacactg    300

acaaggagg                                                            309
```

```
<210> SEQ ID NO 34
<211> LENGTH: 408
<212> TYPE: DNA
<213> ORGANISM: Mycobacteria tuburculosis

<400> SEQUENCE: 34

atgaccacca caccagcacg tttcaaccac ttggtgacgg taaccgacct ggaaacgggt     60

gaccgcgccg tctgcgaccg cgaccaggtg gccgagacga tccgggcgtg gttcccggac    120

gcgcccttgg aggtgaggga agcgctcgtt cggctgcagg ccgcgttgaa tcggcacgag    180

cacaccggcg agctcgaagc gttcctgcgg atcagcgtcg agcacgccga cgccgccggc    240

ggcgacgagt gcggcccggc gatcctggcc ggccgctccg ggccggaaca agccgccatc    300

aaccggcaac tcggactcgc cggcgacgac gagcccgacg gcgacgacac cccgccgtgg    360

agccggatga tcgggcttgg cggcggaagc ccagcggaag acgagcgc                 408
```

```
<210> SEQ ID NO 35
```

-continued

<211> LENGTH: 1407
<212> TYPE: DNA
<213> ORGANISM: Mycobacteria tuburculosis

<400> SEQUENCE: 35
gtgaaacggc tcagcggctg ggacgcggta ctgctttaca gcgagacccc gaatgtgcac 60
atgcacacac tcaaggtcgc cgtgatcgaa ttggattcgg acagacagga attcggtgtc 120
gacgcgtttc gcgaggtgat cgctggccgg ctgcataagc ttgagccatt gggctatcag 180
ctggttgatg tcccgttgaa gttccatcac ccgatgtggc gggagcactg ccaggtcgat 240
ctcaactacc acatccggcc gtggcggttg cgcgccccgg ggggtcggcg cgaactcgac 300
gaggcggtcg gagaaatcgc cagcaccccg ctgaaccgcg accacccgct gtgggagatg 360
tacttcgttg aggggcttgc caaccaccgg atcgcggtgg ttgccaaaat tcaccatgcg 420
ttggctgacg gtgttgcctc ggcaaacatg atggcacggg ggatggatct gctgccggga 480
ccggaggtcg gccgctatgt gcctgacccc gctcctacca agcggcagtt gctgtccgcg 540
gcgttcatcg accacttgcg ccacctcggc cggattcctg caaccatccg gtacaccacg 600
cagggtctag gccgggtgcg acgtagctcg cgcaagctct cacccgcact gaccatgcca 660
tttaccccgc caccgacgtt catgaatcac cggctcaccc cggagcgcag gttcgccacc 720
gccaccctgg cgctgattga cgtgaaggcg acggccaagt tgctgggggc gacgatcaac 780
gacatggtgc tggccatgtc gaccggcgct ctgcgtaccc tgctattgcg ctatgacggc 840
aaggccgaac cgctgctggc gtcggtcccg gtgagttacg acttctcacc ggagcggatc 900
tccggtaacc gcttcaccgg aatgctggtg gcgctgcctg ccgactccga cgacccgttg 960
cagcgggtgc gcgtctgtca cgaaaacgcg gtctccgcca aggagagcca ccagcttttg 1020
ggaccggagt tgatcagccg ctgggcggct tactggccac ctgccggtgc ggaagccttg 1080
ttccggtggt tgtctgagcg cgacgggcag aacaaggtac tcaacttgaa tatctcgaat 1140
gttcccggtc cgcgcgaacg cggccgcgtg gggccgcgc tggtcaccga gatctattcg 1200
gtgggcccgt tgaccgccgg tagcggattg aatatcacgg tgtggagtta tgtcgatcag 1260
ctcaatatct cggtgttaac cgatggttcc accgtgcagg acccgcatga agtaaccgcg 1320
ggaatgatcg cggacttcat cgaaatacgc cgcgccgctg gtctttccgt ggagttgaca 1380
gtcgtcgagt ccgcgatggc gcaggca 1407

<210> SEQ ID NO 36
<211> LENGTH: 786
<212> TYPE: DNA
<213> ORGANISM: Mycobacteria tuburculosis

<400> SEQUENCE: 36
atgagcagcg aaagcgacgc agccaacacc gaacctgagg ttctggtaga acagcgggat 60
cggattttga tcatcacgat caaccgcccg aaagccaaga acgcggtcaa cgccgcagtc 120
agccggggct tggccgatgc gatggatcag cttgacggcg atgccggcct gtcggtggca 180
atcctgaccg gtgggggcgg ttcgttctgc gcgggcatgg acctcaaggc gttcgcccgg 240
ggcgagaatg tcgtcgtcga aggtcgcggc cttggcttta ccgaacgtcc gccgaccaag 300
ccgctcattg ctgcggtgga aggctacgcg ttggcgggtg gcaccgagct ggcgcttgct 360
gccgacctga tcgtggcggc cagggattcg gcgttcggga ttcctgaagt caagcggggt 420
ctggttgccg gcggcggggg attgctgcgg ttgccggagc gcatcccgta tgcgatagcc 480
atggagttgg cgctgaccgg tgacaaccta ccggccgaac gcgcgcacga gctggggctc 540

-continued

```
gtcaacgttt tggccgagcc ggggaccgcc ctcgatgctg cgatcgcgtt ggcggagaag    600

atcaccgcca atgggccgct ggcggtggtg gccaccaagc ggattatcac cgagtcgcgt    660

gggtggagtc ccgacactat gttcgctgag cagatgaaga tcctggtgcc ggtgttcacc    720

tccaacgacg cgaaggaagg tgcgatcgcg ttcgccgaga ggcgccggcc ccgttggacg    780

ggcacc                                                               786
```

```
<210> SEQ ID NO 37
<211> LENGTH: 1461
<212> TYPE: DNA
<213> ORGANISM: M. tuberculosis

<400> SEQUENCE: 37

atgtctgaca gtgccacgga atacgacaag cttttcatcg gcggcaagtg gaccaaaccg     60

tcgacctccg atgttatcga ggtacgctgc ccagccactg ggaatatgt cggcaaggtg    120

ccgatggcgg ccgccgccga cgtcgacgcc gcggtcgccg cagcacgtgc ggcgttcgac    180

aacggcccct ggccctcgac cccgccgcac gagcgtgcgg cggtgatcgc tgcggcggtc    240

aagatgctgg ctgagcgcaa ggacctgttc accaagctgc tcgcagccga aaccggccag    300

ccgccgacca tcatcgagac gatgcactgg atgggttcga tgggggcgat gaactacttt    360

gccggtgcag cggacaaggt cacctggacc gaaacccgca ccggctccta tggacagagc    420

attgtcagcc gtgagccggt cggtgtggtg ggcgcgatcg tggcctggaa cgtcccgctg    480

tttctggccg tcaacaagat tgcgccggcg ctgctggccg gctgcaccat cgtgctcaag    540

cccgccgccg aaacaccgct gaccgcaaac gctttggcgg aggtgttcgc cgaggtgggc    600

ctgcccgagg gggtgttgtc ggtagtgccg ggagggattg agaccggtca ggcgctgacg    660

tctaacccgg acatcgacat gtttaccttc accggcagct cggccgtcgg ccgagaggtc    720

ggcaggcgtg ccgctgagat gctcaagccg tgcaccttag aactcggcgg caagtcggcg    780

gccatcattc tcgaggacgt cgacctggcc gcagctattc cgatgatggt gttctccggc    840

gtcatgaacg ccggacaggg ctgcgtcaac cagacccgca ttctggctcc gcgctcccgg    900

tacgacgaaa tcgtggctgc ggtaactaat ttcgtaacgg ctctcccggt gggcccgccg    960

tcggacccgg cagctcagat cgggccgctg atctcggaga agcagcggac tcgcgttgaa   1020

ggctacatcg ccaagggcat cgaggagggc gctcggttgg tgtgcggcgg cggccgtccc   1080

gagggcttgg acaacggctt ctttatccaa cccaccgtat tcgccgatgt cgacaacaag   1140

atgaccatcg cacaggagga gatcttcggg ccggtgctgg ccatcattcc ttatgacacc   1200

gaggaggacg cgatcgcgat cgccaacgat tcagtgtatg ggctggcggg cagcgtgtgg   1260

accaccgacg tgcccaaagg catcaagatc tcgcagcaga tccgcaccgg gacatacgga   1320

atcaactggt acgccttcga tcccggctca cccttcggcg gctacaagaa ctccggaatc   1380

ggccgcgaga acgggcccga gggtgtcgaa cacttcaccc agcaaaagag tgtcctgctg   1440

ccgatgggct acaccgtcgc g                                             1461
```

```
<210> SEQ ID NO 38
<211> LENGTH: 831
<212> TYPE: DNA
<213> ORGANISM: M. tuberculosis

<400> SEQUENCE: 38

atggcacgct gcgatgtcct ggtctccgcc gactgggctg agagcaatct gcacgcgccg     60
```

-continued

```
aaggtcgttt tcgtcgaagt ggacgaggac accagtgcat atgaccgtga ccatattgcc    120

ggcgcgatca agttggactg gcgcaccgac ctgcaggatc cggtcaaacg tgacttcgtc    180

gacgcccagc aattctccaa gctgctgtcc gagcgtggca tcgccaacga ggacacggtg    240

atcctgtacg gcggcaacaa caattggttc gccgcctacg cgtactggta tttcaagctc    300

tacggccatg agaaggtcaa gttgctcgac ggcggccgca agaagtggga gctcgacgga    360

cgcccgctgt ccagcgaccc ggtcagccgg ccggtgacct cctacaccgc ctccccgccg    420

gataacacga ttcgggcatt ccgcgacgag gtcctggcgg ccatcaacgt caagaacctc    480

atcgacgtgc gctctcccga cgagttctcc ggcaagatcc tggcccccgc gcacctgccg    540

caggaacaaa gccagcggcc cggacacatt cctggtgcca tcaacgtgcc gtggagcagg    600

gccgccaacg aggacggcac cttcaagtcc gatgaggagt tggccaagct ttacgccgac    660

gccggcctag acaacagcaa ggaaacgatt gcctactgcc gaatcgggga acggtcctcg    720

cacacctggt tcgtgttgcg ggaattactc ggacaccaaa acgtcaagaa ctacgacggc    780

agttggacag aatacggctc cctggtgggc gccccgatcg agttgggaag c             831
```

<210> SEQ ID NO 39
<211> LENGTH: 300
<212> TYPE: DNA
<213> ORGANISM: M. tuberculosis

<400> SEQUENCE: 39

```
atgtgctctg gacccaagca aggactgaca ttgccggcca gcgtcgacct ggaaaaagaa     60

acggtgatca ccggccgcgt agtggacggt gacggccagg ccgtgggcgg cgcgttcgtg    120

cggctgctgg actcctccga cgagttcacc gcggaggtcg tcgcgtcggc caccggcgat    180

ttccggttct tcgccgcgcc cggatcctgg acgctgcgcg cgctgtcggc ggccggcaac    240

ggcgacgcgg tggtgcagcc ctcgggcgcg ggcatccacg aggtagacgt caagatcacc    300
```

<210> SEQ ID NO 40
<211> LENGTH: 441
<212> TYPE: DNA
<213> ORGANISM: M. tuberculosis

<400> SEQUENCE: 40

```
atggccaatg tggtagctga aggtgcctac ccttactgtc ggctcactga tcagccgctg     60

agtgtggacg aagtgctagc cgccgtctcg ggccccgaac aaggcggcat tgtcatattt    120

gtgggaaacg tgcgtgacca caatgccggg catgatgtca cgcggttgtt ctacgaggcg    180

tatccgccga tggtgattcg gacattgatg tcgatcatcg gacggtgtga agacaaggcc    240

gagggtgtcc gcgttgctgt cgcgcaccgg accggtgaat tgcaaatcgg tgatgccgcg    300

gtcgttattg gcgcgtcagc tccccaccgt gcggaggcat ttgacgccgc gcgtatgtgt    360

atcgagttgc ttaagcagga agtgccgatt tggaagaagg aattcagctc gaccggtgct    420

gaatgggtcg gcgatagacc a                                               441
```

<210> SEQ ID NO 41
<211> LENGTH: 600
<212> TYPE: DNA
<213> ORGANISM: M. tuberculosis

<400> SEQUENCE: 41

```
atgagtccgt ctccatcggc cctgctcgcc gaccacccgg accgcattcg ttggaacgcg     60

aaatacgagt gcgctgaccc cacggaggcg gtatttgcgc ccatatcctg gctcggcgac    120
```

-continued

```
gtgctgcagt tcggggtgcc agaagggccg gttctggaac tggcgtgcgg tcggtccggc    180
accgcgctgg ggctagccgc ggcgggccgc tgcgtgactg cgatcgacgt ttccgatacc    240
gcgttggttc agctcgagct cgaagcgacc cgacgggaat tggccgatcg cctcacactg    300
gtgcacgccg atctctgctc ctggcagtcg ggggatggac gctttgctct ggtactttgc    360
cgactattct ggcatccgcc cacttttcgc caggcttgcg aggctgtggc gccgggcggt    420
gtagtggcgt gggaggcatg gcggcggccc atcgatgtcg ctcgggatac ccgtcgagcc    480
gaatggtgct tgaagccagg ccagcccgag tctgaacttc ccgccggctt cacggtgatt    540
cgggtggtcg acaccgatgg ttcagagccg tcgcggcgca tcatcgccca acggtcactg    600
```

<210> SEQ ID NO 42
<211> LENGTH: 1200
<212> TYPE: DNA
<213> ORGANISM: Mycobacteria tuburculosis

<400> SEQUENCE: 42

```
atgacaagca cctcgattcc gacgttcccg ttcgaccggc cggtcccgac ggagccgtcc     60
ccaatgctgt cggaactgag aaacagctgt ccggtagccc cgatagagtt gccctcgggg    120
cacacagcat ggctcgtcac tcgctttgac gatgtaaagg gagtgctgtc cgacaagcgt    180
ttcagctgca gggcggcagc gcacccgtcg tcgcccccgt tcgtgccgtt cgtgcagctt    240
tgccccagct tgttgagcat cgatgggccc caacacaccg cggcccgccg tctgctcgcg    300
cagggcctaa atcccggctt catcgcacgc atgcggcccg ttgtccaaca gatcgtcgac    360
aatgcgctcg acgatctggc agccgcggaa ccaccggtgg acttccagga aatagtaagt    420
gtccctatcg gagaacagct catggccaag ctactcgggg tcgagcccaa aaccgtgcac    480
gagctcgcgg cgcacgtgga tgcggcgatg tccgtgtgtg agatcggcga cgaggaggtg    540
agccggcggt ggtcagcact gtgcacgatg gtcatcgaca tactgcaccg caagctcgcc    600
gaaccgggtg atgacctact tagcacgatc gcccaggcga accggcaaca gtccaccatg    660
accgacgagc aggttgtcgg catgctcctc accgtcgtga tcggaggagt cgacacaccg    720
atcgccgtga tcacaaacgg gctggcgagc ctgctgcacc accgcgatca atatgaacgg    780
ctcgttgaag acccaggccg tgtcgctcgt gcggttgaag aaatagtccg gtttaatccg    840
gcaactgaaa ttgagcactt gcgagttgtc accgaggatg tcgtcattgc cggaaccgcg    900
ctatcggcgg ggagcccagc atttacctct atcacttcgg ctaaccgcga ctccgaccaa    960
ttcctggacc ccgatgagtt tgatgtcgaa cgtaatccga acgaacacat agcatttgga   1020
tatggtccac atgcttgccc ggcctcagcg tattcacgca tgtgcttgac gacgttcttc   1080
acctcgctta cccagcgatt tccgcaactt caactcgcaa gaccgtttga ggatttggaa   1140
cgacggggta agggcctaca ttcggtgggg atcaaggaac tccttgttac ctggccgacg   1200
```

<210> SEQ ID NO 43
<211> LENGTH: 498
<212> TYPE: DNA
<213> ORGANISM: Mycobacteria tuburculosis

<400> SEQUENCE: 43

```
gtgcgcattg tcaatgcggc ggacccattt tcgatcaacg atctaggctg tggctatggg     60
gctctactgg actacctaga tgcgcgtggc ttcaaaactg attacaccgg catcgacgtc    120
tcccccgaaa tggtgcgcgc ggccgcacta cgtttcgaag gtcgggcgaa cgcagacttc    180
```

-continued

```
atctgcgcgg cgcgcataga tcgggaggcg gactatagcg tcgcgagtgg aatattcaat    240

gttcgtctga aatcgttgga cacggaatgg tgcgctcaca tcgaagcgac gctcgacatg    300

ctgaatgccg cgagtcgccg tggcttctct tttaattgcc tgacatctta ttccgatgca    360

tcaaagatgc gcgacgacct gtactatgct gacccatgcg ccctatttga tctctgcaag    420

cgcaggtact ccaagagtgt tgcgcttctg cacgactacg gcttgtatga attcacaatt    480

ctggttagga aggcgtca                                                  498
```

<210> SEQ ID NO 44
<211> LENGTH: 693
<212> TYPE: DNA
<213> ORGANISM: Mycobacteria tuburculosis

<400> SEQUENCE: 44

```
ttgaagaaag tcgcgattgt tcaatcaaat tacatacctt ggcgaggata ttttgacctg     60

attgcattcg tcgatgaatt catcatctat gatgacatgc aatataccaa gcgtgattgg    120

cgaaacagaa atcggatcaa aacgagccag gggttacagt ggataactgt tcccgtccag    180

gtgaagggac gtttccatca aaagatacgt gagacgctga tcgacggcac cgattgggcg    240

aaagcgcact ggcgggcact agaattcaac tacagcgcgg ccgctcattt tgcggagatc    300

gctgactggc tcgcgccgat ttacctcgaa gaacagcaca cgaatctttc cttactcaac    360

aggcgtctat tgaatgcgat ttgcagttat ctcggtatca gcacgcgact ggcaaattcg    420

tgggactacg aattagccga cggcaagacc gagagactgg ccaacctctg ccaacaggcc    480

gcagcgaccg aatatgtctc tggcccctca gcccgttcgt atgtcgatga gcgcgtgttc    540

gacgaactta gcatccgggt aacttggttc gattatgacg gctaccgcga ttataagcaa    600

ttgtggggag ggttcgagcc cgccgtgtcg attctggatc tgctctttaa cgtcggagcc    660

gaggctccgg actatttgag gtactgtcgc cag                                 693
```

<210> SEQ ID NO 45
<211> LENGTH: 395
<212> TYPE: DNA
<213> ORGANISM: Mycobacteria tuburculosis
<220> FEATURE:
<221> NAME/KEY: misc_feature
<222> LOCATION: (1)...(395)
<223> OTHER INFORMATION: n = A,T,C or G
<220> FEATURE:
<221> NAME/KEY: misc_feature
<222> LOCATION: 27, 44, 104, 119, 180, 224, 237, 245, 254, 301, 327,
370, 385, 393
<223> OTHER INFORMATION: n = A,T,C or G

<400> SEQUENCE: 45

```
vvmsartgva rhgtsgrgcg dvgargndvs vatrkrsrgd rvgnhgarar rmkrvrgavt     60

asrrwagssr tmgtasvsaa tayaswyavd vstvvgdcwd wgmngrhcsd yamvaaagna    120

dysadytava awaaryagsh wgargcyvat mavsawaarg argrvvvtga aaawgvdrgn    180

stgvvaayva srrwgattva vvkvvgvvaa rwrwaggtgv vvsnaawrgg tashgknssg    240

grdrnvsgka dsknysgkgt grtgavvvvv avagrrvmvg vatatsadva yyvvaavard    300

nggagdaahg drrravgvcv savasvnvav gyvyggakgv vgttvttvtw awvtcvvvsy    360

arkarhdshn gtrsddtaas ttscnvssrg gcnyt                               395
```

<210> SEQ ID NO 46
<211> LENGTH: 879
<212> TYPE: DNA

-continued

<213> ORGANISM: Mycobacteria tuburculosis

<400> SEQUENCE: 46

```
gtgtttgcgt tgagtaataa tctgaaccgt gtgaacgcat gcatggatgg attccttgcc      60
cgtatccgct cacatgttga tgcgcacgcg ccagaattgc gttcactgtt cgatacgatg     120
gcggccgagg cccgatttgc acgcgactgg ctgtccgagg acctcgcgcg gttgcctgtc     180
ggtgcagcat tgctggaagt gggcgggggg gtacttctgc tcagctgtca actggcggcg     240
gagggatttg acatcaccgc catcgagccg acgggtgaag gttttggcaa gttcagacag     300
cttggcgaca tcgtgctgga attggctgca gcacgaccca ccatcgcgcc atgcaaggcg     360
gaagacttta tttccgagaa gcggttcgac ttcgccttct cgctgaatgt gatggagcac     420
atcgaccttc cggatgaggc agtcaggcgg gtatcggaag tgctgaaacc gggggccagt     480
taccacttcc tgtgcccgaa ttacgtattc ccgtacgaac cgcatttcaa tatcccaaca     540
ttcttcacca aagagctgac atgccgggtg atgcgacatc gcatcgaggg caatacgggc     600
atggatgacc cgaagggagt ctggcgttcg ctcaactgga ttacggttcc caaggtgaaa     660
cgctttgcgg cgaaggatgc gacgctgacc ttgcgcttcc accgtgcaat gttggtatgg     720
atgctggaac gcgcgctgac ggataaggaa ttcgctggtc gccgggcaca atggatggtc     780
gctgctattc gctcggcggt gaaattgcgt gtgcatcatc tggcaggcta tgttcccgct     840
acgctgcagc ccatcatgga tgtgcggcta acgaagaggg                            879
```

<210> SEQ ID NO 47
<211> LENGTH: 1296
<212> TYPE: DNA
<213> ORGANISM: Mycobacteria tuburculosis

<400> SEQUENCE: 47

```
atgtacgaga gacggcatga gcgcggaatg tgcgaccgtg ccgtcgagat gaccgacgtc      60
ggcgctacgg cagcccccac cggacctatc gcgcggggca gcgtcgctcg ggtcggcgcg     120
gcgaccgcgt tggccgttgc ctgcgtctac acggtcatct atctggcggc ccgcgaccta     180
cccccggctt gtttttcgat attcgcggtg ttttgggggg cgctcggcat tgccaccggc     240
gccacccacg gcctcctgca agaaacgacc cgcgaggtcc gctgggtgcg ctccacccaa     300
atagttgcgg gccatcgtac ccatccgctg cgggtggccg ggatgattgg caccgtcgcg     360
gccgtcgtaa ttgcgggtag ctcaccgctg tggagccgac agctattcgt cgaggggcgc     420
tggctgtccg tggggctact cagcgttggg gtggccgggt tctgcgcgca ggcgaccctg     480
ctgggcgcgc tggccggcgt cgaccggtgg acacagtacg ggtcactgat ggtgaccgac     540
gcggtcatcc ggttggcggt cgccgcggca gcggttgtga tcggatgggg tctggccggg     600
tacttgtggg ccgccaccgc gggagcggtg gcgtggctgc tcatgctgat ggcctcgccc     660
accgcgcgca gcgcggccag cctgctgacg cccgggggaa tcgccacgtt cgtgcgcggt     720
gccgctcatt cgataaccgc cgcgggtgcc agcgcgattc tggtaatggg tttcccagtg     780
ttgctcaaag tgacctccga ccagttaggg gcaaagggcg gagcggtcat cctggctgtg     840
accttgacgc gtgcgccgct tctggtccca ctgagcgcga tgcaaggcaa cctgatcgcg     900
catttcgtcg accggcgcac ccaacggctt cgggcgctga tcgcaccggc gctggtcgtc     960
ggcggcatcg gtgcggtcgg gatgttggcc gcagggctta ccggtccctg gttgctgcgt    1020
gttggattcg gccccgacta ccaaactggc ggggcgttgc tggcctggtt gacggcagcg    1080
gcggtagcta tcgccatgct gacgctgacc ggcgccgccg cggtcgcggc cgcactgcac    1140
```

-continued cgggcgtatt tgctgggctg ggtcagcgcg acggtggcgt cgacgctgtt gctgctgctg 1200
ccgatgccgc tggagacgcg caccgtgatc gcgctgttgt tcggtccaac ggtgggaatc 1260
gccatccatg tggccgcgtt ggcgcggcga cccgac 1296

<210> SEQ ID NO 48
<211> LENGTH: 1020
<212> TYPE: DNA
<213> ORGANISM: M. tuberculosis

<400> SEQUENCE: 48
gtgaagcgag cgctcatcac cggaatcacc ggccaggacg gctcgtatct cgccgaactg 60
ctgctggcca aggggtatga ggttcacggg ctcatccggc gcgcttcgac gttcaacacc 120
tcgcggatcg atcacctcta cgtcgacccg caccaaccgg gcgcgcggct gtttctgcac 180
tatggtgacc tgatcgacgg aacccggttg gtgaccctgc tgagcaccat cgaacccgac 240
gaggtgtaca acctggcggc gcagtcacac gtgcgggtga gcttcgacga acccgtgcac 300
accggtgaca ccaccggcat gggatccatg cgactgctgg aagccgttcg gctctctcgg 360
gtgcactgcc gcttctatca ggcgtcctcg tcggagatgt tcggcgcctc gccgccaccg 420
cagaacgagc tgacgccgtt ctacccgcgg tcaccgtatg gcgccgccaa ggtctattcg 480
tactgggcga cccgcaatta tcgcgaagcg tacggattgt tcgccgttaa cggcatcttg 540
ttcaatcacg aatcaccgcg gcgcggtgag acgttcgtga cccgaaagat caccagggcc 600
gtggcacgca tcaaggccgg tatccagtcc gaggtctata tgggcaatct ggatgcggtc 660
cgcgactggg ggtacgcgcc cgaatacgtc gaaggcatgt ggcggatgct gcagaccgac 720
gagcccgacg acttcgtttt ggcgaccggg cgcggtttca ccgtgcgtga gttcgcgcgg 780
gccgcgttcg agcatgccgg tttggactgg cagcagtacg tgaaattcga ccaacgctat 840
ctgcggccca ccgaggtgga ttcgctgatc ggcgacgcga ccaaggctgc cgaattgctg 900
ggctggaggg cttcggtgca cactgacgag ttggctcgga tcatggtcga cgcggacatg 960
gcggcgctgg agtgcgaagg caagccgtgg atcgacaagc cgatgatcgc cggccggaca 1020

<210> SEQ ID NO 49
<211> LENGTH: 966
<212> TYPE: DNA
<213> ORGANISM: M. tuberculosis

<400> SEQUENCE: 49
atgaacgcgc acacctcggt cggcccgctt gaccgcgcgg cccgggtcta catcgccggg 60
catcgcggcc tggtcgggtc cgcgctgcta cgcacgtttg cgggcgcggg gttcaccaac 120
ctgctggtgc ggtcacgcgc cgagcttgat ctgacggatc gggccgcgac gttcgacttc 180
gttctcgagt cgaggccgca ggtcgtcatc gacgcggcgg cccgggtcgg cggcatcctg 240
gccaacgaca cctacccggc cgatttcctg tcggaaaacc tccagatcca ggtcaacctg 300
ctggatgccg ccgtggcggc gcgggtgccg cggctgctgt tcctgggctc gtcgtgcatc 360
tacccgaaac tcgccccgca gccgatcccg gagagcgcgc tgctcaccgg tccgttggag 420
ccgaccaacg acgcgtacgc gatcgccaaa atcgccggca tccttgcggt ccaggcggtg 480
cgccgccaac atggcctgcc gtggatctcg gcgatgccca ccaacctgta cgggccaggc 540
gacaactttt cgccgtccgg ctcgcatctg ctgccggcac tcatccgccg ctatgacgag 600
gccaaagcca gtggcgcgcc caacgtgacc aactggggca ccggcacgcc ccgacgggag 660

-continued

```
ttgctgcacg tcgacgacct ggcgagcgca tgcctgtatc tgctggaaca tttcgacggg    720

ccgacccatg tcaacgtggg aaccggcatc gaccacacca tcggcgagat cgccgagatg    780

gtcgcctcgg cggtaggcta tagcggcgaa acccgctggg atccaagcaa accggacgga    840

acaccacgca aactgctgga tgtttcggtg ctacgggagg cgggatggcg gccttcgatc    900

gcgctgcgcg acggcatcga ggcgacggtg gcgtggtatc gcgagcacgc gggaacggtt    960

cggcaa                                                               966
```

<210> SEQ ID NO 50
<211> LENGTH: 729
<212> TYPE: DNA
<213> ORGANISM: Mycobacteria tuberculosis

<400> SEQUENCE: 50

```
atgaggctgg cccgtcgcgc tcggaacatc ttgcgtcgca acggcatcga ggtgtcgcgc     60

tactttgccg aactggactg ggaacgcaat ttcttgcgcc aactgcaatc gcatcgggtc    120

agtgccgtgc tcgatgtcgg ggccaattcg gggcagtacg ccaggggtct gcgcggcgcg    180

ggcttcgcgg gccgcatcgt ctcgttcgag ccgctgcccg ggccctttgc cgtcttgcag    240

cgcagcgcct ccacggaccc gttgtgggaa tgccggcgct gtgcgctggg cgatgtcgat    300

ggaaccatct cgatcaacgt cgccggcaac gagggcgcca gcagttccgt cttgccgatg    360

ttgaaacgac atcaggacgc ctttccacca gccaactacg tgggcgccca acgggtgccg    420

atacatcgac tcgattccgt ggctgcagac gttctgcggc ccaacgatat tgcgttcttg    480

aagatcgacg ttcaaggatt cgagaagcag gtgatcgcgg gtggcgattc aacggtgcac    540

gaccgatgcg tcggcatgca gctcgagctg tctttccagc cgttgtacga gggtggcatg    600

ctcatccgcg aggcgctcga tctcgtggat tcgttgggct ttacgctctc gggattgcaa    660

cccggtttca ccgacccccg caacggtcga atgctgcagg ccgatggcat cttcttccgg    720

ggcagcgat                                                            729
```

<210> SEQ ID NO 51
<211> LENGTH: 786
<212> TYPE: DNA
<213> ORGANISM: Mycobacteria tuburculosis

<400> SEQUENCE: 51

```
gtgacgtctg ctccgaccgt ctcggtgata acgatctcgt tcaacgacct cgacgggttg     60

cagcgcacgg tgaaaagtgt gcgggcgcaa cgctaccggg gacgcatcga gcacatcgta    120

atcgacggtg gcagcggcga cgacgtggtg gcatacctgt ccgggtgtga accaggcttc    180

gcgtattggc agtccgagcc cgacggcggg cggtacgacg cgatgaacca gggcatcgcg    240

cacgcatcgg gtgatctgtt gtggttcttg cactccgccg atcgtttttc cgggcccgac    300

gtggtagccc aggccgtgga ggcgctatcc ggcaagggac cggtgtccga attgtggggc    360

ttcgggatgg atcgtctcgt cgggctcgat cgggtgcgcg gcccgatacc tttcagcctg    420

cgcaaattcc tggccggcaa gcaggttgtt ccgcatcaag catcgttctt cggatcatcg    480

ctggtggcca agatcggtgg ctacgacctt gatttcggga tcgccgccga ccaggaattc    540

atattgcggg ccgcgctggt atgcgagccg gtcacgattc ggtgtgtgct gtgcgagttc    600

gacaccacgg gcgtcggctc gcaccgggaa ccaagcgcgg tcttcggtga tctgcgccgc    660

atgggcgacc ttcatcgccg ctacccgttc gggggaaggc gaatatcaca tgcctaccta    720

cgcggccggg agttctacgc ctacaacagt cgattctggg aaaacgtctt cacgcgaatg    780
```

-continued tcgaaa 786

<210> SEQ ID NO 52
<211> LENGTH: 894
<212> TYPE: DNA
<213> ORGANISM: Mycobacteria tuburculosis

<400> SEQUENCE: 52
atgtcgacaa acccaggacc agccgaaggg gctaaccaag tgatggcaca ggaacattcg 60
gccggcgcgg tacaattcac cgcccacaac gttcgcctcg acgacggaac cttgacgata 120
ccggagtcct cgcgcacgtt agacgaatcg tcctggttca tctcggcgcg cgggattctg 180
gaaaccgtct ttcccgggga caagagccac ctacgcctgg ccgatgtcgg ctgcttggaa 240
ggcgggtacg cggtcgggtt cgcgcgcatg ggatttcagg tcctcgggat cgaggttcgc 300
gagctgaaca tggcggcctg caactacatc aaatcgaaga ccaacctgcc gaatctccgg 360
ttcgtccacg acaacgccct caacatcgcc aaccacgggc tcttcgatac cgtcttctgc 420
tgcggcctct tctaccacct ggagaatccg aagcaatacc tggaaaccct ctcgtcggta 480
acgaacaagc tgctgattct ccagacgcac ttctcgatca tcaaccggag cgataaatgg 540
ctccggttgc ccacgacggc acgacaattg accgatcggt tgctgcggcg gccggcgccg 600
gtgaagttca tgctctcggc gcccaccgaa catgagggac ttcccggtag gtggtttacc 660
gagttttccg acgaccgctc gtttggccag cgcgacaccg caaaatgggc gtcctgggac 720
aatcgccggt cattctggat tcaacgcgag cacctacttc aggccatcaa agacgtcggc 780
gtcgacctgg tgatggagga gtacgacaac ttggaaccaa gcatcgccga gtcgttgctc 840
ggaggttcct atgcggcgaa tcttcgaggc accttcatcg gtatcaagac ccgg 894

<210> SEQ ID NO 53
<211> LENGTH: 1119
<212> TYPE: DNA
<213> ORGANISM: Mycobacteria tuburculosis

<400> SEQUENCE: 53
gtgccgtacg tccgccgacc accaggccac gacggccgac ggccggcggg cacaggcgat 60
tcacgttcgc catcgcaata cccttgcggc cgcgcaggaa aagggccgac ggtgagtccc 120
cagctttgcc ccaaggtgag catcgtctcg accactcaca accaggcggg ctacgcccgt 180
caggccttcg acagctttct cgaccagcaa accgacttcc cggtggagat catcgtcgcc 240
gacgacgcgt cgaccgatgc caccccggcg atcatccgtg agtacgccga gcggtacccg 300
cacgtgttcc ggccgatctt caggaccgaa aacctcggcc tcaatgggaa cctgaccggc 360
gccctgtcgg ccgctcgcgg cgagtacgtc gcgttgtgcg aggcggacga ctactggatc 420
gatccgctga agctaagcaa acaggtcgca ttcctcgacc ggcaccccaa gacgacggtg 480
tgcttccatc ccgtccgagt gatatgggag gacggccatg ccaaggactc gaagttcccc 540
ccggttcggg tgcggggcaa cttgagcctg gatgcgttga tcttgatgaa cttcatccag 600
accaactcgg ccgtgtaccg tcgcctcgag cgctacgacg acattcctgc cgacgtcatg 660
cccctggact ggtatctgca cgtccggcac gcggtgcatg gcgacatcgc catgttgccc 720
gacaccatgg ccgtgtatcg ccgccacgcc caaggcatgt ggcacaacca ggtggtggac 780
ccgccaaagt tctggttgac gcagggtccg gggcatgcgg cgacgtttga cgcgatgctc 840
gacctgttcc cgggagaccc cgcgcgcgag gagctcatcg ccgtcatggc cgactggatc 900

-continued cttcgccaga tcgccaacgt tccaggcccg gaggggcgcg ccgcgctgca ggaaaccatc 960
gcgcgccatc cccggatcgc catgctggcg ctgcagcacc gcggggcgac acccgcgcgg 1020
cggctcaaga cccagtggcg caagctcgcc gccgcgacgc cgagccgcag ggggctcgtg 1080
gatgtgtggc cctcccggct ccgacgcggc tgtcgagcc 1119

<210> SEQ ID NO 54
<211> LENGTH: 282
<212> TYPE: DNA
<213> ORGANISM: Mycobacteria tuburculosis

<400> SEQUENCE: 54
atgaccatca actatcagtt cggtgatgtc gacgctcatg gcgccatgat ccgcgctcag 60
gccgggttgc tggaggcgga gcatcaggcc atcgttcgtg atgtgttggc cgcgggtgac 120
ttttggggcg gcgccggttc ggtggcttgc caggagttca tcacccagct gggccgtaac 180
ttccaggtga tctacgagca ggccaacgcc cacgggcaga aggtgcaggc tgccggcaac 240
aacatggcac aaaccgacag cgccgtcggc tccagctggg cc 282

<210> SEQ ID NO 55
<211> LENGTH: 294
<212> TYPE: DNA
<213> ORGANISM: Mycobacteria tuburculosis

<400> SEQUENCE: 55
atggcaacac gttttatgac ggatccgcac gcgatgcggg acatggcggg ccgttttgag 60
gtgcacgccc agacggtgga ggacgaggct cgccggatgt gggcgtccgc gcaaaacatc 120
tcgggcgcgg gctggagtgg catggccgag gcgacctcgc tagacaccat ggcccagatg 180
aatcaggcgt ttcgcaacat cgtgaacatg ctgcacgggg tgcgtgacgg gctggttcgc 240
gacgccaaca actacgagca gcaagagcag gcctcccagc agatcctcag cagc 294

<210> SEQ ID NO 56
<211> LENGTH: 324
<212> TYPE: DNA
<213> ORGANISM: Mycobacteria tuburculosis

<400> SEQUENCE: 56
gtgcttttgc ctcttggtcc gcctttgccg cccgacgcgg tggtggcgaa acgggctgag 60
tcgggaatgc tcggcgggtt gtcggttccg ctcagctggg gagtggctgt gccacccgat 120
gattatgacc actgggcgcc tgcgccggag gacggcgccg atgtcgatgt ccaggcggcc 180
gaaggggcgg acgcagaggc cgcggccatg gacgagtggg atgagtggca ggcgtggaac 240
gagtgggtgg cggagaacgc tgaaccccgc tttgaggtgc cacggagtag cagcagcgtg 300
attccgcatt ctccggcggc cggc 324

<210> SEQ ID NO 57
<211> LENGTH: 1524
<212> TYPE: DNA
<213> ORGANISM: M. tuberculosis

<400> SEQUENCE: 57
atgtcacgcc gagcattcct ggctaaggcg gctggagccg gggcagcggc ggttttgacg 60
gactgggccg caccggtgat cgaaaaggcc tatggtgccg gtccctgctc gggtcatttg 120
accgatatcg agcacatcgt gctgtgccta caggagaaca ggtcgttcga tcactatttc 180
ggcacgcttt ctgccgtcga cgggttcgac actccgacgc cgctgtttca acaaaagggc 240

-continued tggaacccgg agacgcaggc gctggacccc accggcatta cgctgcccta ccgcatcaat 300
accaccgggg gtcccaacgg ggttggcgag tgcgtcaacg acccagacca ccagtggatt 360
gccgcgcact tgtcatggaa cggcggcgcc aatgacggct ggctgccggc gcaggcgcgg 420
acccggtcgg tggccaacac gcccgtggtg atgggctatt acgcacgtcc tgacataccg 480
atccactact tgttggccga taccttcacg atctgcgacc agtacttctc gtcgcttctt 540
ggcgggacga tgcctaaccg gctctattgg atcagcgcca ccgtcaatcc cgacggggat 600
caaggtgggc cgcagatcgt cgaacccgcc atccagccga agttgacctt cacctggcgc 660
atcatgccgc agaacctcag tgacgccggc atcagttgga aggtgtacaa cagcaagctg 720
ctcggcgggc tcaacgacac ttccttgagc cgtaacgggt atgtgggcag tttcaaacag 780
gccgcagatc cgaggtcgga cctggcccgt tatggcatcg ccccggccta cccgtgggat 840
ttcatccgcg acgtcatcaa caacacgctg ccccaggtgt cctgggtcgt tccgttgacc 900
gtcgagtccg aacatccgtc attcccggtg gcagtcggtg cggtgacgat cgtgaacttg 960
ataagggtgt tgctgcgcaa tccggcggtg tgggagaaaa ccgcgttgat catcgcctat 1020
gacgaacatg gcggcttctt cgaccacgtc acaccgctca ccgcgccgga gggcacaccc 1080
ggcgaatgga ttcccaacag tgttgacatc gacaaggtcg acggctccgg cggaatacgt 1140
ggacccatcg gcttgggctt tcgcgtgccc tgcttcgtca tttcgcctta cagtcgcggc 1200
gggctgatgg tccatgatcg gttcgaccac acatcgcagc tgcaattgat cggcaagcgt 1260
ttcggggtgc cggttcccaa cttgacaccc tggcgtgcca gtgtcaccgg cgatatgacg 1320
tcggcattca atttcgcggc cccgccggac ccgtcgccac ccaatctgga ccacccggtc 1380
cgtcaattgc cgaaggtcgc caagtgcgtg cccaatgtgg tgctgggttt cttgaacgaa 1440
ggcctgccgt atcgggtgcc ctacccccaa acaacgccag tccaggaatc cggtcccgcg 1500
cggccgattc ccagcggcat ctgc 1524

<210> SEQ ID NO 58
<211> LENGTH: 1536
<212> TYPE: DNA
<213> ORGANISM: M. tuberculosis

<400> SEQUENCE: 58
atgtcacgtc gagagttttt gacaaagctc actggcgcag gcgcagcggc attcctgatg 60
gactgggctg caccggtgat tgaaaaggcc tacggcgccg ggccttgtcc cggacatttg 120
accgacatcg agcatatcgt gttgctgatg caggagaacc ggtcattcga ccactatttc 180
ggaacgcttt ccagcaccaa tggcttcaac gccgcgtcgc cggcattcca acaaatgggt 240
tggaacccca tgacgcaggc gttggacccc gccggggtca ccattccgtt ccgcttggac 300
accacccgag gcccctcct ggacggcgag tgcgtcaacg accccgagca ccagtgggtg 360
gggatgcacc tggcctggaa cggtggtgcc aacgacaact ggctgccggc gcaggcgacc 420
acccgcgcag gaccatatgt ccctttgacc atgggttact acacgcgcca agacatcccg 480
atccactatc tgctggccga cacgttcacc atctgcgacg gctaccattg ctcgctgctg 540
acgggcaccc tgcccaaccg gctctactgg ttgagcgcca acatcgaccc cgccggcacc 600
gacgggggac cccaattggt agagccgggc ttcctgccgc tgcagcaatt cagttggcgc 660
atcatgccgg aaaacctcga agatgccggg gtcagctgga aggtgtacca gaacaagggc 720
ctcgggcgat tcatcaacac gcccatcagc aataacgggc tggtgcaggc cttccgccag 780

-continued

```
gcagctgatc cgaggtcgaa cttggcccgc tacggtatcg ccccgaccta ccctggggac    840

ttcgctgccg acgtcagggc caaccggcta cccaaggtct cctggttagt tcccaacatc    900

ctgcagtccg aacaccccgc cctgccggta gcgcttggcg cggtgtccat ggtgaccgcg    960

ctgcggatct tgctgtccaa tcccgcggtg tgggaaaaga ccgcacttat cgtcagctat   1020

gacgagaacg gcggcttctt cgaccacgtc acgcccccca cggcaccgcc cgggacaccc   1080

ggcgaattcg tcacggtgcc caacatcgac gcagtacccg ggtccggtgg cattcgtggt   1140

ccgctcggtc tgggttttcg cgttccctgc attgtcattt cgccgtacag ccgcggcccg   1200

ctgatggtct ccgacacgtt cgaccacacc tcgcaattga agttgattcg cgcccggttc   1260

ggcgtgccgg ttcccaacat gaccgcctgg cgcgacggcg tggttggcga catgacctca   1320

gcgttcaact ttgcgactcc accgaattcg accagaccca acttgagcca cccgttgctg   1380

ggagcgctgc cgaagctgcc gcagtgcatc cctaacgtgg tgttgggaac caccgacggc   1440

gcgttgccga gcattcccta tcgggtgccc tatccgcagg tgatgccaac tcaggaaacc   1500

acacccgtcc gcgggactcc cagcgggctg tgcagc                             1536
```

<210> SEQ ID NO 59
<211> LENGTH: 1536
<212> TYPE: DNA
<213> ORGANISM: M. tuberculosis

<400> SEQUENCE: 59

```
atgtcacgtc gagagttttt gacaaagctc actggcgcag gcgcagcggc attcctgatg     60

gactgggctg caccggtgat tgaaaaggcc tacggcgccg ggccttgtcc cggacatttg    120

accgacatcg agcatatcgt gttgctgatg caggagaacc ggtcattcga ccactatttc    180

ggaacgcttt ccagcaccaa tgggttcaac gccgcgtcgc cggcattcca acaaatgggt    240

tggaacccca tgacgcaggc gttggacccc gccggggtca ccattccgtt ccgcttggac    300

accacccgag gccccttcct ggacggcgag tgcgtcaacg accccgagca ccagtgggtg    360

gggatgcacc tggcctggaa cggtggtgcc aacgacaact ggctgccggc gcaggcgacc    420

acccgcgcag gaccatatgt ccctttgacc atgggttact acacgcgcca agacatcccg    480

atccactatc tgctggccga cacgttcacc atctgcgacg gctaccattg ctcgctgctg    540

acgggcaccc tgcccaaccg gctctactgg ttgagcgcca acatcgaccc cgccggcacc    600

gacgggggac cccaattggt agagccgggc ttcctgccgc tgcagcaatt cagttggcgc    660

atcatgccgg aaaacctcga agatgccggg gtcagctgga aggtgtacca gaacaagggc    720

ctcgggcgat tcatcaacac gcccatcagc aataacgggc tggtgcaggc cttccgccag    780

gcagctgatc cgaggtcgaa cttggcccgc tacggtatcg ccccgaccta ccctggggac    840

ttcgctgccg acgtcagggc caaccggcta cccaaggtct cctggttagt tcccaacatc    900

ctgcagtccg aacaccccgc cctgccggta gcgcttggcg cggtgtccat ggtgaccgcg    960

ctgcggatct tgctgtccaa tcccgcggtg tgggaaaaga ccgcacttat cgtcagctat   1020

gacgagaacg gcggcttctt cgaccacgtc acgcccccca cggcaccgcc cgggacaccc   1080

ggcgaattcg tcacggtgcc caacatcgac gcagtacccg ggtccggtgg cattcgtggt   1140

ccgctcggtc tgggttttcg cgttccctgc attgtcattt cgccgtacag ccgcggcccg   1200

ctgatggtct ccgacacgtt cgaccacacc tcgcaattga agttgattcg cgcccggttc   1260

ggcgtgccgg ttcccaacat gaccgcctgg cgcgacggcg tggttggcga catgacctca   1320

gcgttcaact ttgcgactcc accgaattcg accagaccca acttgagcca cccgttgctg   1380
```

-continued

```
ggagcgctgc cgaagctgcc gcagtgcatc cctaacgtgg tgttgggaac caccgacggc   1440

gcgttgccga gcattcccta tcgggtgccc tatccgcagg tgatgccaac tcaggaaacc   1500

acacccgtcc gcgggactcc cagcgggctg tgcagc                             1536
```

<210> SEQ ID NO 60
<211> LENGTH: 1173
<212> TYPE: DNA
<213> ORGANISM: Mycobacteria tuburculosis

<400> SEQUENCE: 60

```
atgattttgg atttttcgtg gttgccgccg gagatcaact cggcgcggat ctatgccggt     60

gcggggtcgg ggccgttgtt tatggcggcg gcggcgtggg aggggttggc tgcggatttg    120

cgggcctcgg cgtcctcgtt tgatgcggtg atcgccgggt tggcggctgg gccgtggtcg    180

ggtccggcgt cggtggcgat ggcgggggcg gcggcgccgt atgtggggtg gttgagtgcg    240

gcggccgggc aggcggagtt gtcggctggt caggctaccg cggcggcgac ggcgtttgag    300

gcggcgttgg cggccacggt gcatccggcg gcggtgacgg cgaatcgggt gttgttgggg    360

gcgttggtgg cgacgaacat tttgggtcag aacacgccgg cgattgcggc cactgagttc    420

gattatgtgg agatgtgggc tcaggacgtg ggtgcgatgg tggggtatca cgcgggggcg    480

gcggcggtgg ctgagacgtt gacgccgttt agtgtgccgc cgctggattt ggcggggttg    540

gcttcccagg ccggtgcgca gttgaccggg atggcgacgt cggtttcggc tgcgttgtct    600

ccgatcgcgg agggtgcggt ggagggggtg ccggctgtgg tggctgcggc gcagtcggtg    660

gcggcggggt tgccggtgga tgcggcgctg caggtggggc aggccgcggc gtatccggcc    720

agtatgttga ttgggccgat gatgcagttg gcgcagatgg ggactacggc caacacggct    780

gggttggccg gtgcggaggc tgcggggttg gctgcggcgg atgtgccgac gtttgccggt    840

gatatcgctt cggggacggg cctaggtggt gccggtggtc tgggtgcggg gatgtcggcg    900

gagttgggta aggcgcggtt ggtgggggcg atgtcggtgc ctccgacctg ggagggggtcg    960

gttcctgcgc ggatggccag ttcggcgatg gcgggtttgg gggctatgcc tgctgaggtg   1020

ccggcggcag gcgggcccat ggggatgatg ccgatgccga tgggtatggg gggtgctggg   1080

gcgggtatgc cggccgggat gatgggccgc ggtggcgcaa atccgcatgt ggtgcaggct   1140

cggcccagtg tggtgccgcg ggtcgggatc gga                                1173
```

<210> SEQ ID NO 61
<211> LENGTH: 1062
<212> TYPE: DNA
<213> ORGANISM: Mycobacteria tuburculosis

<400> SEQUENCE: 61

```
atgccggggc ggttcagaaa cttcggtagc caaaacctgg gtagcggcaa catcggcagc     60

accaacgtgg gcagcggcaa catcggcagc accaacgtgg gcagcggcaa catcggcgac    120

acgaacttcg gtaacggaaa caacggcaac ttcaactttg gtagcggcaa taccggcagt    180

aacaacatcg gcttcggaaa caccggcagc gggaatttcg gtttcggaaa cacgggcaac    240

aacaacatcg gtatcgggct caccggcgat ggtcagatcg gcatcggcgg actgaactcg    300

ggcagcggaa acatcggttt cgggaactcc ggcaccggaa acgtcggttt gttcaactcc    360

ggcaccggca acgtaggctt cgggaactcc ggtactgcga acactggatt cgggaacgcg    420

ggcaacgtca acaccggatt ttggaacggc ggcagcacaa acactggcct cgctaacgcc    480
```

-continued

```
ggcgccggca acacaggctt tttcgacgct ggcaactaca acttcggcag tcttaacgcc    540

ggaaacataa actcgagttt tgggaattcg ggtgacggca acagtggttt cctcaatgct    600

ggcgacgtca actccggtgt gggcaatgcg ggtgatgtca acactggctt agggaactcg    660

ggcaacatca atactggtgg gtttaatccg ggcacgctca acacgggctt cttcagcgcg    720

atgacccaag ctggtccgaa ttcgggcttc ttcaacgccg gtaccggtaa ctctggtttc    780

gggcacaacg acccggctgg cagtggcaac tcgggcattc agaactcggg cttcggcaac    840

tcgggctatg tcaataccag caccacaagc atgttcggcg gtaactcagg ggtgctcaac    900

acgggctacg gcaactcagg tttctataac gcggccgtca acaacaccgg gatttttgtg    960

accggcgtga tgagttcggg atttttcaat tttgggacgg gcaactcggg cctgctggtc   1020

agcggcaatg ggctttcggg tttcttcaag aacttgttcg ga                      1062
```

<210> SEQ ID NO 62
<211> LENGTH: 654
<212> TYPE: DNA
<213> ORGANISM: Mycobacteria tuburculosis

<400> SEQUENCE: 62

```
atgagccgac tcctagcttt gctgtgcgct gcggtatgca cgggctgcgt tgctgtggtt     60

ctcgcgccag tgagcctggc cgtcgtcaac ccgtggttcg cgaactcggt cggcaatgcc    120

actcaggtgg tttcggtggt gggaaccggc ggttcgacgg ccaagatgga tgtctaccaa    180

cgcaccgccg ccggctggca gccgctcaag accggtatca ccacccatat cggttcggcg    240

ggcatggcgc cggaagccaa gagcggatat ccggccactc cgatgggggt ttacagcctg    300

gactccgctt ttggcaccgc gccgaatccc ggtggcgggt tgccgtatac ccaagtcgga    360

cccaatcact ggtggagtgg cgacgacaat agccccacct ttaactccat gcaggtctgt    420

cagaagtccc agtgcccgtt cagcacggcc gacagcgaga acctgcaaat cccgcagtac    480

aagcattcgg tcgtgatggg cgtcaacaag gccaaggtcc caggcaaagg ctccgcgttc    540

ttctttcaca ccaccgacgg cgggcccacc gcgggttgtg tggcgatcga cgatgccacg    600

ctggtgcaga tcatccgttg gctgcggcct ggtgcggtga tcgcgatcgc caag          654
```

<210> SEQ ID NO 63
<211> LENGTH: 489
<212> TYPE: DNA
<213> ORGANISM: Mycobacteria tuburculosis

<400> SEQUENCE: 63

```
gtgtgctgca atggcgtggt gactccgggt gatccagccg acattgcagc gatcaaacag     60

ctcaaatacc ggtatctgcg ggcattggac accaagcatt gggacgactt caccgacacc    120

ctggccgagg atgtcaccgg cgattacggg tcatcggtcg gtacggagct gcacttcacc    180

aaccgcgccg acctggtcga ctacctgcgc caggcactcg gcccgggtgt catcaccgaa    240

caccgggtca cccatccgga aatcaccgtg accggcgata ccgcaaccgg catctggtac    300

ctgcaagacc gggtcatcgt cgccgagttc aatttcatgc tcatcggcgc cgcgttctac    360

cacgaccagt accgacgaac caccgacggc tggcggatca gcgccaccgg ctacgaccga    420

acctacgagg cgaccatgtc gttggcgggc cttaacttca acatcaggcc gggccgcgcg    480

ctggccgat                                                            489
```

<210> SEQ ID NO 64
<211> LENGTH: 1227

-continued

<212> TYPE: DNA
<213> ORGANISM: Mycobacteria tuburculosis

<400> SEQUENCE: 64
atgagccaat cccggtacgc ggggttgtcc cgcagcgagc tggcagttct gttacccgag 60
ctgttgttga tcggccagct gatcgaccga tcgggcatgg cctggtgtat acaggcattc 120
ggccgccagg agatgctgca gatcgccatc gaggagtggg cgggcgccag cccgatctac 180
accaagcgca tgcaaaaggc gctgaacttc gagggcgacg acgtgcccac catcttcaag 240
gggctacagc tcgacatcgg cgcgccgccg caattcatgg acttccgttt caccctgcac 300
gaccgctggc acggcgagtt tcacctcgac cactgcggtg cgctgctcga cgtggagccg 360
atgggcgacg actacgtcgt cggcatgtgc cacaccatcg aagatccgac gttcgacgcc 420
accgcgatcg cgaccaaccc gcgcgcgcag gtgcgcccca tccaccggcc gccccgcaag 480
ccggccgacc ggcatccgca ctgtgcgtgg accgtcatca tcgacgagtc ctatcccgag 540
gctgagggta ttccggcgct ggacgcggtc cgtgaaacca aagctgccac ctgggaatta 600
gacaacgtcg atgcgtctga cgacgggctg gtggactatt cgggtccgct ggtgtccgac 660
ctggacttcg gggcgttctc gcattccgca ctggtgcgga tggccgatga ggtctgcctg 720
caaatgcacc tgctgaatct gtcgttcgcc attgccgtgc ggaaacgggc caaagccgat 780
gctcaactgg ccatttcggt gaacacccgc cagttgatcg gagtggccgg gctgggcgca 840
gaacgcattc accgtgcgat ggctttaccc ggcggaatcg aaggcgcgtt aggtgtgctg 900
gagctacacc cgctgctcaa cccggccggt tacgtgctgg ccgaaacgtc gccggaccgt 960
ctggtggtgc acaactcgcc agcccacgcc gacggcgcct ggatttcgtt gtgcacaccg 1020
gcatccgtgc agccgttgca ggccatcgcc accgctgtag acccgcatct gaaggttcgg 1080
atcagcggga cggacaccga ctggaccgcg gaactcatcg aggccgatgc cccagcgagc 1140
gaactgccgg aggtgttggt agccaaggtc agtcgcggat cggtcttcca gttcgagccg 1200
aggcgctcac tgccgttgac cgtgaaa 1227

<210> SEQ ID NO 65
<211> LENGTH: 1860
<212> TYPE: DNA
<213> ORGANISM: Mycobacteria tuburculosis

<400> SEQUENCE: 65
atgtacgacc cgctggggtt gtcgatcggg accacaaacc tggtcgcggc gggtaacgga 60
ggtccgccgg ttactcgtcg cgccgtgctg accctgtacc cgcattgcgc accgaaaatc 120
ggtgtgccta gccagaaccc gaacttgatc gagccgggcg ccctaatgag cggctttgtt 180
gagcgcattg gagatgcggt ggcgctggtg tctcccgacg gatccgtgca cgatccagac 240
ctcttgctgg tcgaggcgct ggatgcgatg gtgctgaccg ccggtgcgga cgcgagttcc 300
tcggagatcg ccattgccgt tcccgcgcat tggaagcccg gagctgtaca cgcactgcgt 360
aacggtttgc ggacgcacgt cggcttcgtc cgcagcggca tggcgccgcg cctggtttcc 420
gatgcgatcg cggcgttgac cgcggtgaac tcggaattgg gcctgcccca cggcagtgtg 480
gtggggttgc ttgatttcgg tggctccgcg acttacgtca ccttggtgga gaccaagtcg 540
gattccagga cgtcggattt ccagcccgtt agtgccacgg cacggtacca ggacttttcc 600
ggtagtcaga tcgaccaggc tttgctgctt cgggtcatcg accaattcgg gtacggcgat 660
gacgtcgatc cggccagtac cgccgcggtc gggcaactcg gccaactcag ggagcagtgc 720

-continued cgtgcggcaa aggaacgact gtccaccgac gttgccacgg aattgttcgc tgagcttgcc 780
gggtgcagct cgagcatcga gatgactcgg gaacagctcg aagacctgat ccaggatcca 840
ttgaccggct tcatctacgc gttcgacgac atgctggcgc gccacaacgc gagctgggcg 900
gatctcgcgg cggtggtcac cgtcggcggt ggtgccaata ttccccttgt gactcaacgt 960
ctttcgttcc acactcgtcg acctgtgctg accgcgtcgc aacccgggtg cgcggcggcg 1020
atgggtgcgt tgctgctcgc caaccgtggg ggagagcgcg attcgcgaac gcggacgtcc 1080
atcggcctcg ccacggccgc agccgccggc accagtgtca tcgagctgcc ggccggcgac 1140
gtcatggtca tcgaccatga ggccttgacc gatcgcgagt tggcctggtc gcagaccgac 1200
ttcccaagcg aagctccggc gcgtttcgag ggcgactcgt ataacgaagg cggcccctgc 1260
tggtcgatgc gtctgaacgc ggtcgagccc cccaaaggac cagcgtggcg gcgaatccgg 1320
gtgtcgcagt tgctcatcgg ggtgtcggcg gtagtggcca tgaccgcgat cgggggcgtg 1380
gcattgacgt tgacagccat cgagagacgc ccaagcccgc taccaacccc aattgtgccc 1440
ggcctggccc cgatgccgcc cggatccgtc gtgcctagct cgcgcgcacc gaccccgccg 1500
ccaccgccgt cgaccgttgc gccgcttccc agtgcggcac cggccccgac gacggtcgcg 1560
ccggcaccgc cgccgcccac acaggtggtg acgaccacga cagcgccacc cgtcaccacg 1620
acgccgaggc cgtcgccgac caccacaacg accaccgcgc caccgtcgac aacgacgaca 1680
accgagccgc cggtgacgac cacttcgacg attccaacga ttccgacgac tacgacgacg 1740
gtgaagatga ccacggagtg gttgcacgtc ccgtttttgc ccgttccgat cccggtcccg 1800
attccgcaaa atccgggtgc cggcgaaccg cagaacccgt tcggaagcct tggctctggg 1860

<210> SEQ ID NO 66
<211> LENGTH: 720
<212> TYPE: DNA
<213> ORGANISM: M. tuberculosis

<400> SEQUENCE: 66
atgatccgat tggtccgtca ttcgatcgcc ctggtggccg ccggccttgc cgccgcattg 60
tcggggtgcg attcccacaa ctcgggatcg ctcggtgccg atccgcggca ggtgaccgtg 120
ttcggatccg ggcaagtgca gggtgtgccg gacacgttga tcgctgacgt cggcattcag 180
gtcaccgcgg ccgacgtcac cagcgcgatg aaccagacca atgatcgcca gcaagcggtg 240
atcgatgcac tggtgggtgc cggcctggac cgcaaggaca tccgcaccac cagggtcacc 300
gtggcaccgc agtacagcaa tccggagccg gccggaaccg ccaccatcac cgggtatcgg 360
gcagacaacg acatcgaggt gaagatccac ccgaccgacg ccgcgtcgcg gctgctggcc 420
ctcgtcgtca gcaccggcgg tgacgccacc cggatcagct cggtcagcta ctcgattggc 480
gacgactcgc agctggtgaa ggatgcccgg gcgcgcgcct tccaagacgc caagaaccgt 540
gcggaccagt acgcacaact gtcggggctg cggctaggca aggtgatctc gatctccgag 600
gcatctggcg ccgcgcccac gcacgaggcg ccggcgccgc cgcgcggcct atccgcggtg 660
ccgctggaac ccggccagca gacggtgggc ttctcggtca cggtggtctg ggaactgacc 720

<210> SEQ ID NO 67
<211> LENGTH: 297
<212> TYPE: DNA
<213> ORGANISM: Mycobacteria tuburculosis

<400> SEQUENCE: 67
atgtcgatca tgcacgccga gccagagatg ctggctgcga ccgcgggggga actgcagtcg 60

-continued

```
atcaacgccg ttgcgcgggc cggaaatgca gcggtggcgg gcccgacgac gggtgtggtt    120

ccggccgccg ctgatttggt gtccctgcta accgcctccc agtttgccgc gcatgcacag    180

ctgtaccagg cgattagtgc cgaggcgatg gcggtccagg agcagttggc gaccacgctg    240

ggcatcagcg ccggttcata tgcggccacc gaggctgcca acgccgccac gatcgct       297
```

```
<210> SEQ ID NO 68
<211> LENGTH: 1239
<212> TYPE: DNA
<213> ORGANISM: Mycobacteria tuburculosis

<400> SEQUENCE: 68

atgctggact ttgctcagtt accgccggag gtcaactccg cgctgatgta cgccggaccc     60

ggttcgggac cgatgctggc tgccgcggcg gcctgggagg cgctggccgc cgagttgcaa    120

accacggcgt ccacctacga cgctctgatc actggcctgg ccgacgggcc atggcagggg    180

tcctccgcgg cgtccatggt ggctgccgcc acgccccagg tggcgtggtt gaggagcacc    240

gccgggcagg ccgagcaagc cggcagccaa gcggtggcag cggcgagtgc ttatgaggcg    300

gcgtttttcg cgaccgtgcc gcccccggag atcgcggcca acagggcgtt gttgatggcg    360

ttgctggcga cgaacttcct tggccagaac acggcggcga tcgcggccac cgaggcgcaa    420

tacgccgaga tgtgggccca ggatgcggcc gcgatgtacg gctatgctgg cgcgtcggcg    480

gcggcgacgc agttgtcgcc attcaatccg gcggcgcaga ccatcaaccc ggccgggctg    540

gccagccagg ccgcatctgt cggacaagct gtcagcgggg ccgcaaatgc gcaagcactc    600

accgacattc ctaaagcgtt gtttgggctt agcggaatct tcaccaatga accgccttgg    660

ctcaccgacc ttggcaaggc gctcggtttg accgggcaca cctggtcctc ggacggtagc    720

gggctcatcg tgggcggagt gcttggcgac tttgtgcagg gtgtgaccgg gtcggccgaa    780

cttgatgcca gcgtggccat ggacacgttc ggcaaatggg tctcgcccgc tcggctcatg    840

gtcacccaat tcaaggacta ctttggcctg gcgcacgacc tgccgaagtg ggcgagtgaa    900

ggcgccaaag ccgccggtga ggccgccaag gcgttgccgg ccgccgttcc ggccattccg    960

agtgctggcc tgagcggcgt tgcgggcgcc gtcggtcagg cggcgtcggt cgggggattg   1020

aaggttccgg ccgtttggac cgccacgacc ccggcggcga gccccgcggt gctggcggcg   1080

tccaacggcc tcggagccgc ggccgccgct gaaggttcga cacacgcgtt tggcgggatg   1140

ccgctcatgg gtagcggtgc cggacgtgcg tttaacaact tcgctgcccc tcgatacgga   1200

ttcaagccga ccgtgatcgc ccaaccgccg gctggcgga                          1239
```

```
<210> SEQ ID NO 69
<211> LENGTH: 294
<212> TYPE: DNA
<213> ORGANISM: Mycobacteria tuburculosis

<400> SEQUENCE: 69

atgacctcgc gttttatgac ggatccgcac gcgatgcggg acatggcggg ccgttttgag     60

gtgcacgccc agacggtgga ggacgaggct cgccggatgt gggcgtccgc gcaaaacatt    120

tccggcgcgg gctggagtgg catggccgag gcgacctcgc tagacaccat gacccagatg    180

aatcaggcgt ttcgcaacat cgtgaacatg ctgcacgggg tgcgtgacgg gctggttcgc    240

gacgccaaca actacgaaca gcaagagcag gcctcccagc agatcctcag cagc          294
```

```
<210> SEQ ID NO 70
```

-continued

<211> LENGTH: 282
<212> TYPE: DNA
<213> ORGANISM: Mycobacteria tuburculosis

<400> SEQUENCE: 70
atgaccatca actatcaatt cggggacgtc gacgctcacg gcgccatgat ccgcgctcag 60
gccgggtcgc tggaggccga gcatcaggcc atcatttctg atgtgttgac cgcgagtgac 120
ttttggggcg gcgccggttc ggcggcctgc caggggttca ttacccagct gggccgtaac 180
ttccaggtga tctacgagca ggccaacgcc cacgggcaga aggtgcaggc tgccggcaac 240
aacatggcac aaaccgacag cgccgtcggc tccagctggg cc 282

<210> SEQ ID NO 71
<211> LENGTH: 1185
<212> TYPE: DNA
<213> ORGANISM: Mycobacteria tuburculosis

<400> SEQUENCE: 71
atgaaggcac cgttgcgttt tggcgttttc atcacgccat tccatccgac cggtcaatcc 60
ccgaccgtgg cgttgcaata cgacatggag cgcgtcgttg cgctggaccg gctcggctac 120
gacgaggcgt ggtttggcga acaccactcc ggtggctacg agctgatcgc ttgcccggag 180
gtgtttatcg cggccgcagc ggaacggacc acccacatcc ggctaggtac cggagtggtt 240
tcgctgccct accatcatcc gctaatggtg gccgaccgtt gggtgctgct ggatcacctg 300
acccgtgggc gggtcatgtt cggcaccggc cccggcgcgc tgccgtcgga cgcctacatg 360
atgggcatcg atccggtcga gcagcgacga atgatgcagg agtccctcga ggcgattctc 420
gcgctgttcc gtgccgcacc tgacgagcga atcgaccgcc actccgactg gttcaccctg 480
cgtgaagcgc aattgcacat ccgcccctac acctggccgt accccgaaat cgctaccgca 540
gccatgattt cgccatcggg tccgcgactg gccggtgcgc tgggcacgtc gctgttatca 600
ctgtcgatgt cagtgcccgg cggctacgct gcgctggaaa cagcgtgggg cgtggtgcgg 660
gagcaggccg ccaaagctgg gcggggcgag ccggatcgcg ccgattggcg ggtgttgagc 720
atcatgcact tgtcggacag ccgcgaccag gcgatcgacg actgcactta cgggttaccc 780
gacttctcga ggtacttcgg cgcggcaggg tttgtcccgt tggcgaacac cgtggaaggc 840
acccagtcgt ctcgggaatt cgtcgagcaa tacgcggcca agggaaattg ctgcatcggc 900
acgcccgatg acgcgatcgc ccacattgaa gacttgctgc accggtcggg tggcttcgga 960
acgttgctac tgctcggcca cgactgggcc ccgccaccgg caacctttca ctcctatgag 1020
ctgttcgccc gtgctgtgat tccttatttc aagggacaac tcgcggcgcc gcgggcgtcg 1080
cacgaatggg ctagaggcaa gcgcgaccaa ttgattggcc gcgccggcga agcggtcgtc 1140
aaagccatca ccgagcacgt cgccgaacaa ggggaagcgg gcagc 1185

<210> SEQ ID NO 72
<211> LENGTH: 966
<212> TYPE: DNA
<213> ORGANISM: M. tuberculosis

<400> SEQUENCE: 72
atgggcgcac ctaccgaacg gttagttgat accaacggcg tgcgactgcg agtggtcgag 60
gccggtgagc ccggcgcacc cgtggtgata ctggcccacg gctttcccga actggcctat 120
tcatggagac accagattcc tgcgcttgcc gacgccggct accacgtgtt ggctcccgat 180
cagcgcggtt acggcggatc gtctcgccca gaggcgatcg aggcctacga cattcaccgg 240

-continued

```
ttgaccgctg acctagtggg cctactagat gatgtcggtg ccgagcgggc ggtctgggtt    300
ggtcatgact ggggtgccgt ggtggtgtgg aacgcgccac tgctgcacgc tgaccgagtc    360
gccgccgttg ccgcgttgag cgtccccgcg ctgccccggg cacaggtgcc gccgacgcaa    420
gcgttccgca gcaggtttgg ggagaacttc ttctacatcc tttatttcca ggagcccggc    480
atcgccgacg ccgaactcaa tggcgacccg gcccgcacga tgcgccgaat gatcggcggt    540
ctgcgccctc cgggcgatca gagcgcggca atgcgtatgc tggcgcccgg ccccgacggc    600
tttatcgatc ggcttccgga gccggccggg ttgccggcct ggattagtca ggaggaactc    660
gaccactaca tcggcgagtt cacccgcacc ggtttcaccg gcggcctgaa ctggtaccgc    720
aacttcgacc gcaactggga gaccacggcc gacctcgccg gcaagacgat ctccgtgccc    780
tcgttgttca ttgcgggcac agccgatccc gtcttgacgt tcacccgcac cgaccgcgct    840
gcggaggtga tctccggccc gtatcgcgag gtgctgatcg acggggccgg tcactggctg    900
cagcaggaac gtcccggtga ggtgaccgcg gccctgctgg agttcctgac ggggttggag    960
ttgcga                                                               966
```

<210> SEQ ID NO 73
<211> LENGTH: 1365
<212> TYPE: DNA
<213> ORGANISM: Mycobacteria tuburculosis

<400> SEQUENCE: 73

```
gtgaataccg atgtgctggc tggcctgatg gccgagctgc ccgaggggat ggtggtcacc     60
gaccccgccg tcaccgacgg ctaccggcaa gaccgggcct ttgacccttc ggccggcaaa    120
ccgctggcaa tcatccggcc acggcgcacc gaagaggtgc agacggtgct gcgttgggcc    180
agtgcgaacc aggtgcccgt ggtgacccga ggagccggta gcggcctttc gggcggggcg    240
accgccctgg atggcgggat cgtgctgtcc accgaaaaga tgcgcgacat caccgtcgac    300
ccggtcaccc gcaccgcagt gtgccagccc ggcctgtaca acgccgaggt gaaggaggcc    360
gccgccgaac acggcctgtg gtatcccccg gatccgtcgt cgttcgagat ctgcagcatc    420
ggcggcaaca tcgccaccaa cgccggcggg ctgtgctgcg tgaagtacgg cgtcacaggc    480
gactacgtac tgggcatgca ggttgtgctg gccaacggca ccgcggtccg gctgggcggc    540
ccacggctca aggacgtcgc cgggctttcc ctgaccaaac tgttcgtcgg cagcgaaggc    600
acgctgggcg tcatcacgga ggtgacgttg cgactgctgc ccgcacagaa tgcatcgagc    660
atcgtggtgg ccagcttcgg ctcggtgcag gcggcggtcg atgcggtgct cggggttacc    720
ggccgacttc gccccgcgat gctggagttc atggattcgg tggcgatcaa cgccgtcgag    780
gacaccttgc ggatggacct ggaccgcgat gcggcggcca tgctggtggc tggttctgat    840
gaacgtggcc gcgcggccac cgaagacgcc gccgtgatgg ccgccgtgtt cgccgaaaac    900
ggtgcgatag acgtgttttc gaccgacgac ccggatgagg gcgaggcgtt cattgcggcc    960
cggcggttcg ccattccggc ggtcgagagc aagggggcgt tgctgctcga ggacgtcggg   1020
gtaccgctgc ccgcactggg cgaactggtc accgggattg cgcgcatcgc cgaggagcgg   1080
aatctgatga tctcggtgat cgcccacgcc ggggacggca atacccaccc gttgctggtg   1140
tacgaccccg cagatgccgc gatgctagag cgcgcccacc tcgcgtacgg cgaaatcatg   1200
gacctggccg tcggcctggg cggcacgatc accggcgaac acggcgtggg ccggttgaaa   1260
cggccgtggt tggccggcta tctcgggccc gacgtcctgg ccctcaacca gcgcatcaag   1320
```

-continued caagcgctgg acccccaggg catcctcaat cccggctcgg cgatc 1365

<210> SEQ ID NO 74
<211> LENGTH: 1215
<212> TYPE: DNA
<213> ORGANISM: Mycobacteria tuburculosis

<400> SEQUENCE: 74
atgacatcag taatgtctca cgaattccag ctcgccaccg ccgaaacctg gccgaatccg 60
tggccgatgt accgcgcgtt gcgcgaccac gacccggtgc accacgtcgt cccgccgcag 120
cgtcccgagt acgactacta cgtgctgtcc cggcacgccg acgtctggtc ggcagcgcgg 180
gaccatcaga cgttctcgtc ggcgcaaggc ttgaccgtta actacggcga gctggaaatg 240
attggactgc acgacacccc gcccatggtg atgcaggatc cgccggtcca caccgagttt 300
cgcaagctgg tgtcgcgcgg cttcacgcca cgacaggtcg aaaccgtcga gcccacggtg 360
cgcaagttcg tcgttgagcg gctcgaaaag ctgcgcgcca acggtggcgg cgacattgtc 420
accgaactat tcaaaccgct cccgtcgatg gtggtggcgc actatctcgg tgttcccgaa 480
gaggattgga cgcaattcga cgggtggacc caggccatcg tggcggcgaa cgcggttgac 540
ggcgccacca ccggcgcact ggacgcggtc ggctcgatga tggcctactt caccgggctg 600
atcgagcgac gccgcaccga gcccgccgac gacgccatct cccacctggt agccgccggg 660
gtcggcgccg acggcgacac cgccggcaca ctgtccatac tggcgttcac gttcaccatg 720
gtcaccggcg gcaacgacac cgtcaccggc atgctaggcg gttcgatgcc gttgctgcac 780
cggcggcccg accagcgccg gctgctgctg gatgacccag agggcatccc cgacgcggtc 840
gaggagctgc tgcggctcac ctcgccggtg caggggctgg cgcgcacaac cacgcgcgac 900
gtcacgatcg gtgacaccac catcccggcc ggtcgccggg tgctgctgct gtacggctcg 960
gccaaccgtg acgaacgcca atacggcccg gacgcagccg aactcgatgt cactcggtgc 1020
ccgcgcaaca tcttgacctt cagccacggc gcccaccact gcctgggtgc ggccgcggcc 1080
cggatgcaat gccgggtggc gctgaccgaa ctgctggccc ggtgcccgga cttcgaggtg 1140
gccgagtcac gcatcgtgtg gtccggcggc agttatgtcc ggcgtccgct gtcggtgccg 1200
ttccgagtga catcc 1215

<210> SEQ ID NO 75
<211> LENGTH: 606
<212> TYPE: DNA
<213> ORGANISM: Mycobacteria tuburculosis

<400> SEQUENCE: 75
atggcgggta ccgactggct gtccgcgcgt cggaccgagt tagccgcaga tcggatactc 60
gacgccgccg agcgactctt tacgcagcgt gacccggcgt cgatcggcat gaacgagatc 120
gccaaggccg caggctgttc gcgcgcaaca ctgtatcggt acttcgacag ccgcgaggcg 180
ctgcgaaccg cgtacgtgca ccgcgagacc cgccggctcg gccgcgagat catggtgaag 240
atcgccgatg tcgtcgaacc tgccgaacgg ctgctggtga gcatcaccac gacgttgcgg 300
atggtccgcg acaaccccgc gttggccgcg tggtttacca ccacccgccc accgatcggc 360
ggcgagatgg ccggacggtc cgaggtgatc gcggccctgg ccgcggcatt cctcaactca 420
ctaggtcccg acgatccgac caccgtcgaa cgccgcgccc gctgggtggt ccggatgctc 480
acatcgctgc tgatgttccc cggccgtgac gaagccgacg aacgagcgat gatcgcggag 540
ttcgtcgtcc cgatcgtgac acctgcttct gccgccgcta ggaaggccgg tcaccctgga 600

-continued cccgag 606

<210> SEQ ID NO 76
<211> LENGTH: 534
<212> TYPE: DNA
<213> ORGANISM: Mycobacteria tuburculosis

<400> SEQUENCE: 76
atgcatccaa tgataccagc ggagtatatc tccaacataa tatatgaagg tccgggtgct 60
gactcattgt ctgccgccgc cgagcaattg cgactaatgt ataactcagc taacatgacg 120
gctaagtcgc tcaccgacag gctcggcgag ctgcaggaga actggaaagg tagttcgtcg 180
gacttgatgg ccgacgcggc tgggcggtat ctcgactggc tgactaaaca ctctcgtcaa 240
attctggaaa ccgcctacgt gatcgacttc ctcgcatacg tctatgagga gacacgtcac 300
aaggtggtac ccccggcgac tatcgccaac aaccgcgagg aggtgcacag gctgatcgcg 360
agcaacgtgg ccggggtaaa cactccagca atcgcaggac tcgatgcaca atatcagcag 420
taccgggccc aaaatatcgc tgtcatgaac gactatcaaa gtaccgcccg gtttatccta 480
gcgtatctgc cccgatggca ggagccgccg cagatctacg gggcgggggg cggg 534

<210> SEQ ID NO 77
<211> LENGTH: 1230
<212> TYPE: DNA
<213> ORGANISM: Mycobacteria tuburculosis

<400> SEQUENCE: 77
gtggccacga tagcccaacg gctgcgtgac gaccacgggg tggcggcgtc ggagtcgtcg 60
gtgaggcgtt ggatcgcaac gcatttcgcc gaggaggtgg cccgcgagag agtcacggtg 120
ccgcgcggac cggtcgatgc gggtagtgag gcgcagatcg attacgggcg gctgggcatg 180
tggttcgacc cggccaccgc gcgccgggtc gcggtgtggg cgttcgtgat ggtgctggcg 240
ttctcccgac acctgttcgt gcgtccggtc atccggatgg accaaaccgc ttggtgtgct 300
tgccatgtcg ccgcattcga attcttcgac ggggtgccgg cgcggctagt gtgtgacaac 360
ctcaggaccg gggtggacaa gcccgacctg tacgacccgc agatcaaccg ctcctacgcc 420
gagctggcca gccactacgc cacgctggtc gacccggccc gcgccagaaa acccaaagat 480
aaaccccgcg tggagcggcc gatgacctat gtgcgggact cgttttggaa aggccgcgag 540
ttcgattcgc tggcccagat gcagcaggcg gcggtcacct ggagcaccga agtggccggg 600
cttcggtact tacgtgcctt ggagggcgcc caacccctgc ggatgttcga agctgtggag 660
caacaagcgt tgatcgcatt gccgcccagg gcatttgaac tcaccagctg gtcgatcggc 720
accgtcgggg tggacacgca cctcaaagtt ggcaaggcac tctattccgt gccgtggcgg 780
ctgatcgggc aacgcctgca cgcgcgcacc gccggtgatg tggtgcagat cttcgccggc 840
aacgatgtgg tggccaccca tgtgcgccga cccagcgggc gctccaccga cttctcccac 900
tacccaccgg agaagatcgc cttccacatg cgcaccccga cctggtgtcg acacaccgcc 960
gaactggtcg gcccagccag ccagcaagtg atcgccgaat tcatgcgcga caacgccatc 1020
caccacctac ggtcggccca aggcgtgctc gggctacgcg acaaacacgg ctgcgaccgg 1080
ctggaggccg cctgcgcccg cgccatcgag gtcggcgacc cgagctatcg caccatcaag 1140
ggcatccttg ttgccggcac cgaacacgcc gccaacgagc cgaccaccag tagtccggca 1200
agcaccgctg gggcgttcc tgcgcggccc 1230

-continued

<210> SEQ ID NO 78
<211> LENGTH: 753
<212> TYPE: DNA
<213> ORGANISM: Mycobacteria tuberulosis

<400> SEQUENCE: 78
atgtctatct gtgatccggc gctgcgtaat gcgctacgta ccctgaaact gtccggcatg 60
ctcgacaccc tcgacgcccg cctggcccaa acccgcaacg gcgacctggg gcatctggaa 120
ttcctgcaag cgttgcgtga agacgagatc gcccgccgcg agtccgccgc cctgacacga 180
cgattacgcc gcgccaagtt cgaagcccaa gccaccttcg aagacttcga cttcactgcc 240
aacccgaaac tgcccggtgc gatgttgcgc gatctggccg cgctgcgctg gctggatgcc 300
ggcgaatcgg tcatcctcca cggcccggtc ggcgtcggaa aaacccatgt agcacaagca 360
cttgtccacg ccgtggcccg ccgcggcggc gacgtgcgct tcgccaaaac ctcccgcatg 420
ctctccgacc tcgccggcgg gcacgccgac cgatcctggg gccaacgcat ccgcgaatac 480
accaagccgc tcgtgctcat tctggacgac ttcgcgatgc gtgagcacac cgccatgcac 540
gctgatgacc tctacgagct catcagcgac cgcgccatca ctggcaaacc gctgatcttg 600
accagcaacc gcgcaccgaa taactggtac ggcctgttcc ccaaccccgt cgtcgccgaa 660
tcactcctgg atcggctcat caacaccagc caccaaatcc tcatggacgg acccagctac 720
cgaccccgca agagacccgg ccgcaccacc agc 753

<210> SEQ ID NO 79
<211> LENGTH: 696
<212> TYPE: DNA
<213> ORGANISM: Mycobacteria tuberulosis

<400> SEQUENCE: 79
atgcatctaa tgatacccgc ggagtatatc tccaacgtaa tatatgaagg tccgcgtgct 60
gactcattgt atgccgccga ccagcgattg cgacaattag ctgactcagt tagaacgact 120
gccgagtcgc tcaacaccac gctcgacgag ctgcacgaga actggaaagg tagttcatcg 180
gaatggatgg ccgacgcggc tttgcggtat ctcgactggc tgtctaaaca ctcccgtcag 240
attttgcgaa ccgcccgcgt gatcgaatcc ctcgtaatgg cctatgagga gacacttctg 300
agggtggtac cccggcgac tatcgccaac aaccgcgagg aggtgcgcag gctgatcgcg 360
agcaacgtgg ccgggggtaa acactccagc aatcgcagac ctcgaggcac aatacgagca 420
gtaccgggcc gaaaatatcc aagcaatgga ccgctatcta agttggaccc gatttgcgct 480
atcgaagctg ccccgatggc gggagccgcc gcagatccac aggagcgggt aggtccaaga 540
ggccggcgcg gtcttgcagg ccagcaacaa tgccgcggtc gaccaggccc atcgcttcgc 600
tgctcgcacg acacaccgcg gtttcagatg aatcaggcgt ttcacaccat ggtgaacatg 660
ttgctgacgt gttttgcatg tcaggagaaa ccgaga 696

<210> SEQ ID NO 80
<211> LENGTH: 528
<212> TYPE: DNA
<213> ORGANISM: Mycobacteria tuberulosis

<400> SEQUENCE: 80
atgcatccaa tgataccagc ggagtatatc tccaacataa tatatgaagg cccgggcgct 60
gactcattgt ttttcgcctc cgggcaattg cgagaattgg cttactcagt tgaaacgacg 120
gctgagtcgc tcgaggacga gctcgacgag ctggatgaga actggaaagg tagttcgtcg 180

-continued

```
gacttgttgg ccgacgcggt tgagcggtat ctccaatggc tgtctaaaca ctccagtcag    240

cttaagcatg ccgcctgggt gatcaacggc ctcgcgaacg cctataacga cacacgtcgg    300

aaggtggtac ccccggagga gatcgccgcc aaccgcgagg agaggcgcag gctgatcgcg    360

agcaacgtgg ccggggtaaa cactccagca atcgcagacc tcgatgcaca atacgaccag    420

taccgggccc gcaatgtcgc tgtaatgaac gcctatgtaa gttggacccg atctgcgcta    480

tcggatctgc cccggtggcg ggaaccgccg cagatctaca ggggcggg                528
```

<210> SEQ ID NO 81
<211> LENGTH: 1170
<212> TYPE: DNA
<213> ORGANISM: M. tuberculosis

<400> SEQUENCE: 81

```
atgatcatcg ttgtcgggat cggcgccgac ggcatgaccg gtctctccga gcattctcgc     60

tccgaattgc gcagggccac agtaatttac ggctcgaaac ggcaacttgc cctgctcgac    120

gataccgtca ccgccgagcg ctgggagtgg ccgacgccga tgctgcccgc ggtgcaaggc    180

ctgtcaccgg atggggctga cctacacgtg gttgccagcg gcgacccgtt gttgcatggt    240

atcggctcca ccctgatccg gctgttcggc cacgacaacg tgaccgtgtt gccgcacgtg    300

tccgcggtga cgttggcgtg cgcccggatg ggctggaacg tgtatgacac cgaggtgatc    360

agcctggtca ccgcgcaacc acacaccgcg gtgcgccgcg gcggccgggc catcgtgctg    420

tccggcgatc ggtccacccc gcaggcgctg gcggtgctgc tgaccgagca cggtcgcggt    480

gactccaagt tcagcgtgct cgaacagctt ggcggcccgg ccgaacgccg ccgcgacggt    540

acggcccggg catgggcctg cgacccaccc ctcgatgtcg atgagctcaa cgtgatcgcc    600

gtgcgctacc tgctcgacga gcgcacgtcg tgggcacccg acgaggcatt cgcgcacgac    660

gggcagatca ccaaacaccc gatccgcgtg ctgaccctgg ctgcgctggc gccaaggccc    720

gggcagcggt tatgggacgt cggcgcgggc tcaggcgcca tcgcggtcca gtggtgtcgg    780

agctggccgg gctgcaccgc ggtggcgttc gagcgcgacg aacggcgccg ccgcaacatt    840

gggttcaatg ccgcggcctt cggggtgagc gtcgacgtgc gcggcgacgc gcccgatgcg    900

ttcgacgacg ccgcacggcc gtcggtgatt tttcttggcg gtggtgtaac ccagccaggc    960

ctgcttgagg cctgcctgga cagcctgccc gcaggcggga acttggtcgc caacgctgtc   1020

accgtcgaat cggaagccgc tctggcgcat gcatattcgc gcctcggtgg cgagctacga   1080

cgattccagc actatctcgg cgaaccgctg ggcggcttca ccggttggcg cccacagctg   1140

ccggtcaccc agtggtcggt gaccaagcga                                   1170
```

<210> SEQ ID NO 82
<211> LENGTH: 747
<212> TYPE: DNA
<213> ORGANISM: Mycobacteria tuberulosis

<400> SEQUENCE: 82

```
gtggacgaca cgggcgctgc tccggtagta attttcggcg gccgcagcca gatcggcggc     60

gaactcgcgc gacgcctggc tgccggggcg acgatggtgc tggccgcgcg gaacgccgat    120

caactcgccg accaggccgc cgcactccgc gcagctggcg ctatagcggt gcacacccgg    180

gagttcgacg ccgacgacct ggccgcacac ggcccgttgg tcgcttcgct cgttgccgag    240

cacggcccca tcggcaccgc ggtgctggcc ttcgggatac tcggcgacca ggcccgcgcc    300
```

-continued gagacagacg cggcgcacgc ggtggccatc gtgcacaccg actacgtcgc ccaggtcagc 360
ctgctgactc atctggcagc ggcgatgcgc accgccggac ggggatcgct ggtggtgttc 420
tcctcggtcg ccgggattcg ggtgcgccgc gccaactatg tctacggatc ggccaaagcc 480
ggcctggacg gcttcgccag cggcctggcc gatgcgttgc acggcaccgg ggtgcggtta 540
ctgatcgcgc ggccgggatt cgtcatcggg cgcatgaccg agggcatgac gcccgcaccc 600
ctgtcggtca ccccggagcg ggtggccgcc gcgaccgcgc gtgcgctggt caacggtaag 660
cgcgtggtgt ggattccgtg ggcgctgcgg ccaatgtttg ttgcgctgcg gttgcttccc 720
cggttcgtct ggcgcaggat gccgcga 747

<210> SEQ ID NO 83
<211> LENGTH: 411
<212> TYPE: DNA
<213> ORGANISM: Mycobacteria tuberulosis

<400> SEQUENCE: 83
gtggcgatgg tcaacaccac tacgcggctt agtgacgacg cgctggcgtt tctttccgaa 60
cgccatctgg ccatgctgac cacgctgcgg gcggacaact cgccgcacgt ggtggcggta 120
ggtttcacct tcgaccccaa gactcacatc gcgcgggtca tcaccaccgg cggctcccaa 180
aaggccgtca atgccgaccg cagtgggctt gccgtgctca gccaggtcga cggcgcgcgc 240
tggctctcac tggagggtag ggcggcggtg aacagcgaca tcgacgccgt gcgcgacgcc 300
gagctgcgct acgcgcagcg ctatcgcacc ccgcgtccca atccacgccg agtggtcatc 360
gaggtccaga ttgagcgcgt gctgggatcc gcggatctgc tcgaccgggc c 411

<210> SEQ ID NO 84
<211> LENGTH: 1461
<212> TYPE: DNA
<213> ORGANISM: Mycobacteria tuberulosis

<400> SEQUENCE: 84
atgccccgcg cccgatggct gcagagcgcg gccctcatgg gcgccttggc cgtggtgttg 60
ataaccgcgg caccggtggc cgccgatgcc taccaggtgc ccgctccgcc ctcgcccacc 120
gcatcctgtg acgtaataag cccggttgcg atcccctgcg tggcgctcgg caagttcgcc 180
gacgcggtcg ctgcggagtg tcgccgcgtc ggtgtgcccg atgcgcggtg cgtgcttccg 240
ctcgcgcacc gggtgaccca ggccgcgcgt gatgcctacc tacagtcttg ggtgcatcgc 300
accgcgcggt tccaggatgc gttgcaagac ccggtgccgc tgcgggaaac tcagtggctc 360
ggcacgcaca actcgttcaa cagcctcagc gattcgttca cggtctcgca cgcagactca 420
aaccagcagc tgtcgttggc ccaacagctc gacatcgacg tccgcgcgct cgagctagac 480
ctgcactact tgccccgcct cgagggccac ggcgcccccg gcgtcaccgt gtgtcacggg 540
ctgggaccga agaacgcgaa cctaggctgc accgtcgaac ctctgctggc cacagtgctg 600
ccgcagatcg ccaactggtt gaacgcaccc gggcataccg aggaggtcat cctgctctac 660
ctggaggacc agctgaagaa cgcgtcggcg tatgagtcgg tggtggctac cctcgaccaa 720
gtgttgcggc gtgcggacgg aacaagcctt atctaccgtc ccaacccggc ccggcgtgcc 780
accaacggct gtgtcccgct tccactcgac gtgtcgcggg aggaaatccg cgcatccggc 840
gcacgagccg tgctcgtcgg gtcttgtgcg ccaggttggt cggccgccgt cttcgactgg 900
agcggcgttg agctggaaag cggctcgaac tccggctacc ggccataccc ggcctgcgat 960
gccacctatg gccgcggtgt ctacgcttgg cgactggtcc gctattacga ggactccacg 1020

-continued ctggccacgg cgttggccaa cccgacccgt ccaccggcca atccgcaggc gcttaccccg 1080
ccgaaggtgc cggcgatgac cgattgcggg gtcaatctgt tcggcttcga tcagctgctc 1140
cccgaagacg gccgcattca ggcgtcgttg tggagctggg caccggacga accgcgtgcc 1200
ggtgccggag catgcgccct gcagggcgcg gatggccgct gggtcgccgc atcgtgcggt 1260
gacccacacc ctgcggcctg tcgggacgcg gcaggcaggt ggaccgtgac gccggcaccc 1320
gtggtcttcg ccggggctgc cctagcctgc acagccatcg gcgcggactt taccctgccc 1380
cgaacgggca atcagaacgc ccgtctgcac gccgtggccg ggcccgccgg tggcgcctgg 1440
gtgcattacc tactgccgcc a 1461

<210> SEQ ID NO 85
<211> LENGTH: 429
<212> TYPE: DNA
<213> ORGANISM: Mycobacteria tuberulosis

<400> SEQUENCE: 85
atgaccacca cgccccgaca acccctgttc tgcgcccacg ccgacaccaa cggcgacccg 60
ggccgctgcg cctgcggcca gcagctcgcc gacgtcggcc cggccacccc gccaccgccc 120
tggtgcgaac cgggcaccga acccatctgg gagcagctca ccgaacgata cggcggcgtc 180
acaatctgcc agtggacacg atattttccg gccggcgacc cggtggctgc cgacgtgtgg 240
atcgccgccg acgatcgtgt cgttgacggc cgggtgctgc gcacccaacc ggcgattcac 300
tacacggaac cgcccgtgtt ggggatcggc ccggcggcgg cccgccggct ggccgctgag 360
ctgctcaacg ccgccgacac cctcgacgac ggccgccggc agctagacga cctcggcgaa 420
caccggcgg 429

<210> SEQ ID NO 86
<211> LENGTH: 996
<212> TYPE: DNA
<213> ORGANISM: Mycobacteria tuberulosis

<400> SEQUENCE: 86
gtgaacaccg cgacccgggt ccggctggcc cgcaaacgcg ccgaccggct caatctgaaa 60
ctaatcaaga acggccacca cttcaggttg cgtgacgccg acgagatcac gctggcggtc 120
gggcacctag gggtggtgga agccttcctg gcggcggcca agtcgcaaaa caagccgccc 180
ggtccgccgc cgagcctcca cgccccgcca tcctggcggc gcgacatcga cgactacctg 240
ctcaacctga acgccgccgg tcaacgccca gcgacgatcc ggctacgcaa gacggtgctg 300
tgcgcagccg cccacggcct cggccgccca cccgccgacg tcaccgccga acacctcctg 360
gactggctag gcaaacagca gcacctctcc ccagagggcc gcaaaaccta tcgcagcacg 420
ttgcggggct tcttcgtgtg ggcctacgaa atggaccggg tgcgcgacta tgtcgcagac 480
tccctgccta aggtgcgctg cccgaaacag ccgccccgcc cggccggcga cgacgtctgg 540
caagcggcgc tggccaaggc cgaccgtcga atcgagctga tgatccgcct agccggtgag 600
gccgggctgc gacgcgccga agccgcccag gcgcacaccg gcgacttgat ggacggcggg 660
cttctcctcg ttcacggcaa aggtggtaaa cgccgtattg tgccgatcag cgactacttg 720
gccgcgctca tccgcgacac cccgcacggc tacctgttcc ccaacggcac cggcggccac 780
ctcaccgccg aacacgtggg aaaactcgtc tcccgggcat tacccggtga cgcgaccatg 840
cacaccctgc ggcaccgata cgccacccgc gcctaccgcg gctcccacaa cttgcgagct 900

-continued

```
gtacaacaac ttctcggtca cgcctcgatc gtgacaacag aacgctacac agcgctgtgc    960

gacgacgagg tgcgcgccgc agcagcagcc gcatgg                              996


<210> SEQ ID NO 87
<211> LENGTH: 366
<212> TYPE: DNA
<213> ORGANISM: Mycobacteria tuberulosis

<400> SEQUENCE: 87

gtgcacgtgt gccacacgat cgccgacgtg gtcgaccggg ccaaagccga acgctccgaa     60

aacacgcttc gcaaggattt cacccccctcg gagctgctcg ccgctggtcg ccggatcgcc    120

gagctggaac ggccgaaagc caaacagcgg caacgcgaag gcggcgacca tggccgccag    180

gctcgatatt ctggcttagg ctccatggag cctaagccag aatcagagcg cgatgcccac    240

aaagccgaca ctgccatcag cgaagccctc ggcatctccc gcggccacta ccagcggctc    300

aaacgaatcg acaacgcaac ccgcagcgaa gctggctacc gggatggttt aaacggttgg    360

agcggc                                                               366


<210> SEQ ID NO 88
<211> LENGTH: 324
<212> TYPE: DNA
<213> ORGANISM: Mycobacteria tuberulosis

<400> SEQUENCE: 88

atgtcaggtg gttcatcgag gaggtacccg ccggagctgc gtgagcgggc ggtgcggatg     60

gtcgcagaga tccgcggtca gcacgattcg gagtgggcag cgatcagtga ggtcgcccgt    120

ctacttggtg ttggctgcgc ggagacggtg cgtaagtggg tgcgccaggc gcaggtcgat    180

gccggcgcac ggcccgggac cacgaccgaa gaatccgctg agctgaagcg cttgcggcgg    240

gacaacgccg aattgcgaag ggcgaacgcg attttaaaga ccgcgtcggc tttcttcgcg    300

gccgagctcg accggccagc acgc                                           324


<210> SEQ ID NO 89
<211> LENGTH: 984
<212> TYPE: DNA
<213> ORGANISM: Mycobacteria tuberulosis

<400> SEQUENCE: 89

aaagaccgcg tcggctttct tcgcggccga gctcgaccgg ccagcacgct aattacccgg     60

ttcatcgccg atcatcaggg ccaccgcgag ggccccgatg gtttgcggtg gggtgtcgag    120

tcgatctgca cacagctgac cgagctgggt gtgccgatcg ccccatcgac ctactacgac    180

cacatcaacc gggagcccag ccgccgcgag ctgcgcgatg gcgaactcaa ggagcacatc    240

agccgcgtcc acgccgccaa ctacggtgtt tacggtgccc gcaaagtgtg gctaaccctg    300

aaccgtgagg gcatcgaggt ggccagatgc accgtcgaac ggctgatgac caaactcggc    360

ctgtccggga ccacccgcgg caaagcccgc aggaccacga tcgctgatcc ggccacagcc    420

cgtcccgccg atctcgtcca gcgccgcttc ggaccaccag cacctaaccg gctgtgggta    480

gcagacctca cctatgtgtc gacctgggca gggttcgcct acgtggcctt tgtcaccgac    540

gcctacgctc gcaggatcct gggctggcgg gtcgcttcca cgatggccac ctccatggtc    600

ctcgacgcga tcgagcaagc catctggacc cgccaacaag aaggcgtact cgacctgaaa    660

gacgttatcc accatacgga taggggatct cagtacacat cgatccggtt cagcgagcgg    720

ctcgccgagg caggcatcca accgtcggtc ggagcggtcg gaagctccta tgacaatgca    780
```

-continued ctagccgaga cgatcaacgg cctatacaag accgagctga tcaaacccgg caagccctgg 840
cggtccatcg aggatgtcga gttggccacc gcgcgctggg tcgactggtt caaccatcgc 900
cgcctctacc agtactgcgg cgacgtcccg ccggtcgaac tcgaggctgc ctactacgct 960
caacgccaga gaccagccgc cggc 984

<210> SEQ ID NO 90
<211> LENGTH: 1437
<212> TYPE: DNA
<213> ORGANISM: Mycobacteria tuberulosis

<400> SEQUENCE: 90
atgactaatg aacaacattt cgctgacgat ggcgacatca aacagctcag cctcgacgaa 60
acccgttccg cggcaaaaca gctcctcgac tccgtcgagg gcgacctgac cggtgatgtg 120
gcgcaacgtt ttcaggcgct gacacgccac gccgaggaac tgcgggcgga gcagcgccgc 180
cgcggccgcg aagccgagga ggcgctgcgc cgctgccggg ccggtgagct gagggtggtg 240
cccggtgctc ccaccggcgg cgacgacggc gacgcgccgc cgggcaactc gttgcgcgac 300
atcgcgtttc gcacactgga cgtttgtgtg cgcgatggcc tgatgtcgtc gcgggcggcg 360
gaagccgcgg aaaccttgtg ccgcaccggg ccgccgcagt cgacgtcgtg ggcgcagcgc 420
tggctggcgg ccaccggcaa ccgcgactac ctgggggcgt tcgtcaagag ggtttcgaac 480
cctgttgcgg ggcacacgac ctggaccgac cgggaagcgg ccgcgtggcg tgaggcggcc 540
gcggtggccg ccgagcagcg agcaatgggc ttggtggaca ccgccggcgg gtttttgatc 600
ccggcggcgc tggatccggc gattctgctg tcgggtgatg gttcaacgaa tccgatccgg 660
caggtggcga gggtggtgca aacgacctcc gaggtttggc ggggcgtgac ctccgaaggc 720
gccgaggctc attggtactc cgaagcccag gaggtgtccg acgattcgcc aacgctggcc 780
cagccggcgg tgccgagcta ccgtggctcc tgctggattc cgttcagtct cgagattgag 840
ggtgacgccg ccggattcgt cgcagaggtg ggccgcgtcc tagcggattc ggttgagcag 900
ctgcaggcgg cggcgttcgt cagcggctcc ggcaacggcg agcccaccgg attcgtctcc 960
gcactgaccg gcaccgcgga ctacaccgtc accggcgcgg ggacggaagc cgttgtagcc 1020
gccgacgttt acgcgctgca gtcggcgttg ccgccgcgct ttcaatccaa cagcgcgttc 1080
gcggcgaact tgtccaccat caacgtgctg cgccaggcgg aaaccgcgaa tggggcgctg 1140
aaattcccat cgctgcacgc cagcccgccg atgctggccg ggaaacacat ctgggaggtg 1200
tcgaacatgg acaccgtgga cgcggcggtg accgccacca attacccgct ggtgcttggc 1260
gactggaagc agttcatcat caccgaccgg gtcgggtcga cggtggagct ggtgccgcac 1320
gtgttcggcg gcaaccgccg accgaccgga cagcgcggat tcttctgctg gttccgagtc 1380
ggttctgatg tgctggtgga caatgcgttc cgcgtgctga aggtgcagac caccgcg 1437

<210> SEQ ID NO 91
<211> LENGTH: 531
<212> TYPE: DNA
<213> ORGANISM: Mycobacteria tuberulosis

<400> SEQUENCE: 91
ttgagtagca tcctttttccg cacggccgag ctgcggcctg gtgagggccg caccgtgtac 60
ggcgtcatcg tgccttatgg cgaggtgacc accgtccgcg acctcgacgg cgagttccgg 120
gaaatgttcg ctcctggcgc ttttcggcgc tccatcgctg agcgcggcca caaggtgaag 180

-continued

```
ctgctggtct cccacgacgc tcgaacccgc tacccggttg gccgggccgt cgagctgcgt    240

gaggagcctc acggcttgtt cggggcgttc gagcttgcga acaccccgga cggcgacgag    300

gccctggcga atgtgaaagc tggtgtggtg gacgcgtttt cggtgggttt ccggccgatc    360

cgggaccgcc gggaagggga tgtgatcgtg cgggtcgagg cggcgctgtt ggaggtctcc    420

ttgaccggcg ttccggccta tctgggcgcg cagatcgccg gtgtgcgcgc ggaatcgctt    480

gcagtcgttt cccgttcgct agccgaagcc aggttagccc tgatggattg g             531
```

<210> SEQ ID NO 92
<211> LENGTH: 624
<212> TYPE: DNA
<213> ORGANISM: Mycobacteria tuberculosis

<400> SEQUENCE: 92

```
ttgccatcgc cagcaaccgc ccgaccggac accgccacgg tgggagagcg tgtgcgcgct     60

caagttttat ggggcgtttt ttggcatcat ggcattcgcg acccgaaacc cggaaagagg    120

agggtggtgt tgaaaatggg taggcgtggt cccgcgccgg cgccggcgca gttgaaactc    180

ctcggcggcc gctcgccggg ccgtgattct ggcggccggc gggttacacc accggcggcg    240

ttcgagcgtg ttgcgccgga atgcccggat tggttgccgc caggcgctaa agacatgtgg    300

gggcgcgtcg ttcccgagct tgcggcatta aacctgctga aggagtccga ccttggggtg    360

ctgacctcct tctgcgtcgc ctgggatcag ctcatgcagg ctgtaacagc ctaccgtgaa    420

cagggtttca tcgcgacgaa cgcccgcagc cgacgggtga cggtgcatcc tgccgtggcc    480

gcggcccggg ccgcgacgag ggacgttttg gtgctcgcgc gcgaattggg gtgcacgcca    540

agcgctgagg cgaatttggc tgctgtgctg gcggcggcgg gggaccccga cgacgacgag    600

ttcaacccgt tcgccccaga ccgg                                           624
```

<210> SEQ ID NO 93
<211> LENGTH: 321
<212> TYPE: DNA
<213> ORGANISM: Mycobacteria tuberculosis

<400> SEQUENCE: 93

```
ttgacccaca agcgcactaa acgccagcca gccatcgccg cagggctcaa cgccccgcgt     60

cggaatcgcg ttgggcggca acatggttgg ccggccgacg ttccgtccgc cgagcagcgc    120

cgcgcccaac ggcagcgcga cctcgaggct atccgccgag cgtacgccga gatggtggcg    180

acatcacacg aaatcgacga cgacacagcc gaactggcgc tgttgtcgat gcatctcgac    240

gatgagcagc gccggcttga ggcggggatg aagctcggct ggcatccgta tcacttcccc    300

gacgaacccg acagcaaaca g                                              321
```

<210> SEQ ID NO 94
<211> LENGTH: 243
<212> TYPE: DNA
<213> ORGANISM: Mycobacteria tuberculosis

<400> SEQUENCE: 94

```
atgagcggcc acgcgttggc tgctcggacg ttgctggccg ccgcggacga gcttgtcggc     60

ggcccgccag tcgaggcttc ggccgccgcg ctggccggcg acgccgcggg cgcatggcgg    120

accgcggccg tcgagcttgc gcgagcgttg gtccgcgctg tggcggagtc gcacggcgtc    180

gcggccgttt tgttcgccgc gacggccgcc gcggcggcgg ccgtcgaccg gggtgatccg    240

ccg                                                                  243
```

-continued

<210> SEQ ID NO 95
<211> LENGTH: 1425
<212> TYPE: DNA
<213> ORGANISM: Mycobacteria tuberculosis

<400> SEQUENCE: 95
atggctgaca tcccctacgg ccgtgactat cccgacccga tctggtgtga cgaggacggc 60
cagccgatgc cgccggtcgg cgccgaattg ctcgacgaca ttagggcatt cttgcggcgg 120
ttcgtagtct atccaagcga ccatgaactg atcgcgcaca ccctctggat tgcgcattgc 180
tggtttatgg aggcgtggga ctcaacgccc cgaatcgctt ttttgtcacc ggaacccggc 240
tctggcaaga gccgcgcact cgaagtcacg gaaccgctag tgccccggcc ggtgcatgcc 300
atcaactgca caccggccta cctgttccgt cgggtggccg atccggtcgg gcggccgacc 360
gtcctgtacg acgagtgtga caccctgttt ggcccgaaag ctaaagaaca cgaggaaatt 420
cgcggcgtga tcaacgccgg ccaccgcaag ggagccgtcg cgggccgctg cgtcatccgc 480
ggcaagatcg ttgagaccga ggaactgcca gcgtactgtg cggtcgcctt ggccggcctc 540
gacgacctgc ccgacaccat catgtctcgg tcgatcgtgg tgaggatgcg caggagggca 600
ccaaccgaac ccgtggagcc gtggcgcccc cgcgtcaacg gccccgaggc cgagaagctg 660
cacgaccggt tggcgaactg ggcggccgcc attaacccgc tggaaagcgg ttggccggcg 720
atgccggacg gggtgaccga ccggcgcgcc gacgtctggg agtccctggt tgcggttgct 780
gacaccgcgg gcgggcactg gcccaaaacc gcccgtgcaa ccgcagaaac ggatgcaacc 840
gcaaatcgag gagccaagcc cagcataggc gtgctgctgc tgcgggatat ccgtcgagtc 900
ttcagcgacc gggaccggat gcgcaccagc gacatcctga ccggactgaa ccggatggag 960
gagggaccgt ggggctccat ccgccgcggc gacccgctcg acgcgcgcgg cctcgcgacc 1020
cggctcggca gatacggcat cgggccgaag ttccagcaca gtggtggcga accaccctac 1080
aaagggtatt cgcggaccca gttcgaggat gcgtggtccc ggtatctctc tgccgacgac 1140
gaaacccccg aggaacgaga tttatcggtt tccgcggttt ccgcggtttc accgccggtt 1200
ggcgatcccg gtgatgcaac cggcgcaacc gatgcaaccg atctcccgga ggcgggcgac 1260
ttgccgtacg agccgccggc gcccaacggg caccccaacg gcgacgcgcc gctgtgctcc 1320
gggccgggat gccccaacaa gctcctcagt actgaggcca aggccgccgg caaatgccgg 1380
ccctgccgag gtcgagcggc ggctagcgct cgggacggcg cccga 1425

<210> SEQ ID NO 96
<211> LENGTH: 390
<212> TYPE: DNA
<213> ORGANISM: Mycobacteria tuberculosis

<400> SEQUENCE: 96
atgaccgccg tcggcgggtc gccgccgacg cgacgatgcc cggccacaga ggaccgggca 60
cccgcgacag tcgccacacc gtctagcacc gatcctaccg cgtcccgcgc cgtgtcgtgg 120
tggtcggtgc acgagtatgt cgcaccgacc ctggccgccg ccgtggaatg gccgatggcc 180
ggcaccccgg cgtggtgcga cctcgacgac accgacccgg tcaaatgggc cgcgatctgc 240
gacgctgctc ggcattgggc actccgggtg gagacgtgcc aggccgcgtc ggccgaggca 300
tcacgtgacg tatccgccgc cgccgactgg ccggcggtct ctcgggagat ccagcgtcgg 360
cgtgacgcct acattcggcg ggtggtggtc 390

-continued

<210> SEQ ID NO 97
<211> LENGTH: 258
<212> TYPE: DNA
<213> ORGANISM: Mycobacteria tuberculosis

<400> SEQUENCE: 97
atgtgcgcgt tcccgtcgcc gagtctcggg tggacggtct ctcacgagac cgaaaggccc 60
ggcatggcag acgctccccc gttgtcacgg cggtacatca cgatcagtga ggccgccgaa 120
tatctagcgg tcaccgaccg cacggtccgc cagatgatcg ccgacggccg cctacgcgga 180
taccgctccg gcacccgcct cgtccgtctg cgccgcgatg aggtcgacgg cgccatgcac 240
ccgttcggtg gtgccgca 258

<210> SEQ ID NO 98
<211> LENGTH: 360
<212> TYPE: DNA
<213> ORGANISM: Mycobacteria tuberculosis

<400> SEQUENCE: 98
atggccgatg cggttaagta cgtagttatg tgcaactgcg acgacgaacc gggagcgctc 60
atcatcgcct ggatcgacga cgaacgaccc gccggcgggc acatacagat gcggtcgaac 120
acccgcttca ccgaaacaca gtggggccgc catatcgagt ggaaactcga atgccgggca 180
tgccgaaagt atgcgccgat atccgagatg accgccgcgg cgatcctcga cggtttcggg 240
gcgaagcttc acgagctgag aacgtcgacc atccccgacg ctgacgatcc atcaatagca 300
gaggcgcgac acgtaattcc gttcagcgca ttatgcttgc gcttgagcca gctaggcggg 360

<210> SEQ ID NO 99
<211> LENGTH: 1125
<212> TYPE: DNA
<213> ORGANISM: Mycobacteria tuberculosis

<400> SEQUENCE: 99
gtgacgcaaa ccggcaagcg tcagagacgc aaattcggtc gcatccgaca gttcaactcc 60
ggccgctggc aagccagcta caccggcccc gacggccgcg tgtacatcgc ccccaaaacc 120
ttcaacgcca agatcgacgc cgaagcatgg ctcaccgacc gccgccgcga aatcgaccga 180
caactatggt ccccggcatc gggtcaggaa gaccgccccg gagccccatt cggtgagtac 240
gccgaaggat ggctgaagca gcgtggaatc aaggaccgca cccgcgccca ctatcgcaaa 300
ctgctggaca accacatcct ggccaccttc gctgacaccg acctacgcga catcaccccg 360
gccgccgtgc gccgctggta cgccaccacc gccgtgggca caccgaccat gcgggcacac 420
tcctacagct tgctgcgcgc aatcatgcag accgccttgg ccgacgacct gatcgactcc 480
aacccctgcc gcatctcagg cgcgtccacc gcccgccgcg tccacaagat caggcccgcc 540
accctcgacg agctggaaac catcaccaaa gccatgcccg acccctacca ggcgttcgtg 600
ctgatggcgg catggctggc catgcgctac ggcgagctga ccgaattacg ccgcaaagac 660
atcgacctgc acggcgaggt tgcgcgggtg cggcgggctg tcgttcgggt gggcgaaggc 720
ttcaaggtga cgacaccgaa aagcgatgcg ggagtgcgcg acataagtat cccgccacat 780
ctgatacccg ccatcgaaga ccaccttcac aaacacgtca accccggccg ggagtccctg 840
ctgttcccat cggtcaacga ccccaaccgt cacctagcac cctcggcgct gtaccgcatg 900
ttctacaagg cccgaaaagc cgccggccga ccagacttac gggtgcacga ccttcgacac 960
tccggcgccg tgttggctgc atccaccggc gccacactgg ccgaactgat gcagcggcta 1020

-continued

```
ggacacagca cagccggcgc cgcactccgc taccagcacg ccgccaaggg ccgggaccgc   1080

gaaatcgccg cactgttaag caaactggcc gagaaccagg agatg                   1125
```

<210> SEQ ID NO 100
<211> LENGTH: 225
<212> TYPE: DNA
<213> ORGANISM: Mycobacteria tuberculosis

<400> SEQUENCE: 100

```
gtgatagcgg gcgtcgacca ggcgcttgca gcaacaggcc aggctagcca gcgggcggca     60

ggcgcatctg gtggggtcac cgtcggtgtc ggcgtgggca cggaacagag gaacctttcg    120

gtggttgcac cgagtcagtt cacatttagt tcacgcagcc cagattttgt ggatgaaacc    180

gcaggtcaat cgtggtgcgc gatactggga ttgaaccagt ttcac                    225
```

<210> SEQ ID NO 101
<211> LENGTH: 186
<212> TYPE: DNA
<213> ORGANISM: Mycobacteria tuberculosis

<400> SEQUENCE: 101

```
atgatcgagc agggccgcga ctgccgggac gtggtcaccc agctcgccgc ggtatcgcgc     60

gcactcgacc gcgccggatt caagatcgtt gcggcagggt tgaaggaatg cgtgtccggg    120

gccacggcca gcggcgcggc accgctgagt gcagctgagc tagaaaagct gttcctggcg    180

ctcgct                                                               186
```

<210> SEQ ID NO 102
<211> LENGTH: 357
<212> TYPE: DNA
<213> ORGANISM: Mycobacteria tuberculosis

<400> SEQUENCE: 102

```
atgtcggacc agccacgtca tcaccaggtc ctcgacgacc tgctgcccca acaccgcgct     60

ctacgtcacc agattcccca ggtgtaccag cgatttgtag ccctgggcga cgccgcgctt    120

accgacggcg ctctcagccg caaggtcaag gagcttgtgg cgctggcgat cgcggttgtg    180

caggggtgcg atggctgcgt cgcatcacac gcccaagccg cggtacgggc cggcgctaca    240

gcgcaagaag ccgctgaggc catcggggtc accatcttga tgcacggtgg accggccacc    300

atccacggtg ctcgtgccta cgcggcattt tgcgaattcg ctgacacaac gccgtcc       357
```

<210> SEQ ID NO 103
<211> LENGTH: 1854
<212> TYPE: DNA
<213> ORGANISM: Mycobacteria tuberculosis

<400> SEQUENCE: 103

```
atgtcctatc tcgtcgtggt gccggagttg gtcgcagcgg cggcaacaga tttggcgaac     60

atcggttcgt cgattagtgc agccaacgcg gccgcggcgg caccgaccac ggcactggtc    120

gcagccggcg gcgacgaggt atcggcggcc atagccgcgt tgttcggagc gcatgctcgg    180

gcatatcaag cgttgagtgc ccaggcggcg atgtttcatg aacagtttgt ccgggccctc    240

gccgccggcg gtaactccta cgccgtcgct gaggcggcaa ccgcgcaatc ggttcagcaa    300

gatctgctca acctgatcaa tgcgcccacc caggcgctgt tggggcgtcc gctgatcggc    360

aacggcgcca acgggctgcc gggtacgggc cagaacggcg gcgacggcgg gattctgtac    420
```

-continued

```
ggcaacggcg gcaacggtgg gtccggcggg gtcaaccagg ccggtggcaa tggcgggaat    480

gctgggctgt ggggcaatgg cggatccggc ggagccggcg ggaacgccac cactgccggc    540

cgcaacggct tcaacggggg cgccggggga agcggcggtt tgctgtgggg caatggcggt    600

gccggcgggg ccggtgggaa cggcggtccg gctccgctcg tgggcggggt gggcaccacc    660

ggtggcgccg gcgggaacgg cggcggcgcc gggttgttct acggtttcgg cggcgccggt    720

gggaacggcg ggatgggcgg ggtggcaccg agcaccggcc cctcgatggg catcctcccg    780

gccggcggtg tcggcgggcc tggtggctcc ggcggggcga gcgcgcttgc cttcggctcc    840

ggcggcgtcg gcggtgccgg tggcttgggc gggccgaccg atggcaccgt ccagggggtg    900

ggcggcttcg gcggtcaggg cggcaacggc gggcagagcg gcttgttgtt tggcaacgcg    960

ggagccggcg gggcaggcgc tgccggcgga gccggcaccg gcgacaccga gagcttcggc   1020

ggccacggcg gggccggcgg tgatggcggc gctgttggct tgatcggtaa cggcggggcc   1080

ggcggcaccg gatctcccgg cgctgtggtg ggtggtaacg gcggcgtcgg tggtctgggt   1140

ggcgccggca gtcccggggg tctgttgtac ggcaccgggg gggccggcgg caatggcgga   1200

ccgggtggtg acggtggtac tggcgcgacg gtgggctttg ccggctccgg cggtttcggc   1260

ggtgcggggg gcatcgccca gctgtttggc acgggtggca tgggtggtag cggcggtggt   1320

ataggcgctg gcaccacgac cgtggtgccg cccgacgtcg ccccggtggg tggcacaggc   1380

ggcaatggcg gtcgcgccgg gctgctgttg ggtgtgggtg gcatgggcgg taatggcggt   1440

gccaccagcg tcggcgggac gctctacgcc gccggtggaa acggcggcga cggcgggttg   1500

gtgtggggca acggtggcac cggcgggagc ggtggcgccg gcggggcggg cagcgtcggc   1560

aacggcggtg cgggtggcaa cgcggcactg ctgttcggca acggcggggc gggcggggcc   1620

ggcggcgccg gcggcatcgg tgccggcgga gccggcggct tcggcgcggt tctgtttggc   1680

aacggcgggg ctggcgggag cggtgccccc ggtggcatcg gcgccggtgg caatggcgga   1740

aacgcgctgc tggtcggcaa cggcggcaac ggtggggcag gtaccggtgg ggctgctggc   1800

ggtgccggtg gctcgggcgg gttgctattc ggccaaaatg ggatgcccgg gccg         1854
```

<210> SEQ ID NO 104
<211> LENGTH: 1242
<212> TYPE: DNA
<213> ORGANISM: Mycobacteria tuberculosis

<400> SEQUENCE: 104

```
gtgcatgagg tggctgctcg tgagcaacgt tcggacgggc cgatgaggct ggatgcgcag     60

ggccgactgc agcgttacga ggaggcgttc gctgactacg atgcaccgtt tgcgttcgta    120

gatctcgacg cgatgtgggg caatgccgat caactgcttg cgcgcgccgg cgacaagccg    180

atccgggtgg cgtcgaagtc gctgcgttgc cgaccactgc aacgcgaaat ccttgatgcc    240

agtgagcgat tcgacgggct attgacgttc acgcttaccg agacgctgtg gcttgccggc    300

caaggtttct cgaacctgtt gttggcctac ccgccgaccg accgggcggc attgcgtgcg    360

cttggcgagc tgacggccaa ggacccggac ggggcgccga tcgtgatggt ggacagcgtg    420

gagcaccttg acctgatcga gcgcacgacc gacaagccgg tacggctgtg tctggatttc    480

gatgccggct attggcgcgc cggcgggcgg ataaaaattg gttccaagcg ctcgccgctg    540

cacaccccgg agcaggctcg cgcactcgcg gtggagatcg cgcggcggcc ggcgctaacg    600

ttggcggcgt tgatgtgcta cgaggcccac attgcgggcc tcggtgacaa cgtcgccggc    660

aagcgggtcc acaacgcgat catccgtcgg atgcagcgca tgtcgttcga agagctgcgc    720
```

-continued gagcgtcgtg cccgggccgt cgagctggtg cgcgaggtcg ccgacatcaa gatcgtcaac 780
gccggtggca ccggcgactt gcagctggtt gcgcaggagc cgttgattac cgaagcgacc 840
gccggctcgg gtttttacgc gccgacactg ttcgactcgt attcgacgtt cacgctgcag 900
cccgcggcga tgttcgcgct gccggtatgc cgtcgtcccg gtgcaaagac cgtgaccgcg 960
ctcgggggtg gctatttagc cagcggggtc ggggcgaagg accgcatgcc gactccctac 1020
ctgccggtcg ggctgaagct caatgcgctg gagggaacgg gcgaagttca gacaccgcta 1080
tccggtgatg cagcccgacg gctgaagctt ggcgacaagg tctacttccg ccacaccaag 1140
gccggtgagc tgtgtgagcg gttcgaccat ctgcatctgg tccgtggcgc tgaagtagtc 1200
gacaccgtcc ccacctaccg gggtgaaggg cgcaccttcc tc 1242

<210> SEQ ID NO 105
<211> LENGTH: 1284
<212> TYPE: DNA
<213> ORGANISM: Mycobacteria tuberculosis

<400> SEQUENCE: 105
atggacgagg cccacccggc tcacccggca gatgcggggc ggcccggtgg cccaattcaa 60
ggcgcgcgaa gaggagctgc catgacaccg atcaccgccc tgccgaccga gttggcggcc 120
atgcgcgagg tagtcgagac gctcgcaccc attgagcgtg ccgcgggcga gccgggtgag 180
cacaaggcgg ccgagtggat cgtcgagcgc ctgcgcacgg cgggcgcgca ggacgcgcgc 240
atcgaggagg agcagtacct cgacggctac ccgaggctgc acctcaagct gtcggtgatc 300
ggggtggcgg ccggcgtcgc gggcctgctc agcagacgtt tgcgcatccc cgccgcgctg 360
gccggggtgg gtgcggggct ggcaatcgcc gacgattgcg ccaacgggcc gcgcattgtg 420
cgcaaacgaa cggagacgcc ccggacgaca tggaacgcgg tagccgaggc cggtgatcct 480
gctggtcagc taacagttgt tgtgtgcgct caccacgacg ccgcgcacag cggcaagttt 540
ttcgaggctc atattgagga ggtaatggtc gagctgtttc ccgggattgt ggagcgcatc 600
gacacgcagc tgccgaactg gtgggggccg atcctcgcgc ccgcactcgc cggtgtcggc 660
gccctgcgcg gcagccggcc gatgatgatc gccggaacgg tgggtagcgc cctggccgcc 720
gctttgttcg ccgacatcgc gcgcagtccg gtcgtccccg gtgccaacga caatctctcc 780
gcggttgcgc tgctggtcgc gctggccgag cggctgcgcg agcggccggt gaagggcgtg 840
cgagtgttgc tcgtgtccct gggggccgag gaaacgttgc agggcgggat ctacgggttc 900
ctggcgcgac acaaacccga gctggaccgc gaccgcacat acttcctgaa cttcgacacc 960
atcggctcac ccgagctcat catgctcgag ggcgagggcc cgacggtcat ggaggactac 1020
ttctatcggc cattccggga tctggtcatc cgggcggccg agcgcgccga cgcgccgctg 1080
cggcgcggca tccggtcgcg caacagtacc gacgcggtgt tgatgagccg cgccggctac 1140
ccgaccgcgt gctttgtgtc gatcaaccgg cacaagtcgg tggccaatta ccacctgatg 1200
tccgatacac ctgagaatct ctgctatgag acggtgtccc acgccgtcac cgtcgccgaa 1260
tccgtgatca gggagctggc ccga 1284

<210> SEQ ID NO 106
<211> LENGTH: 1284
<212> TYPE: DNA
<213> ORGANISM: Mycobacteria tuberculosis

<400> SEQUENCE: 106

-continued atgagcccga tatggagtaa ttggcctggt gagcaagtct gcgcgccgtc ggcgatcgta 60
cggccgacct cggaggctga gctggccgac gtgatcgcgc aggcggcgaa aagaggcgag 120
cgggtacgcg cggttggcag cgggcattcg tttaccgaca tcgcctgcac ggacggggtc 180
atgatcgaca tgaccggcct gcagcgggtc ctcgacgtgg accagccgac tggcctggtg 240
acggtcgagg ggggcgcaaa gctacgtgcg ctgggacccc aattggcgca acgacggctc 300
ggcctggaga accagggtga cgtggatccc caatccatca ccggcgcgac cgcgaccgcg 360
acgcacggaa ccggggtgcg tttccagaat ctgtcggcgc ggatcgtttc gctgcggctg 420
gtcaccgcgg gcggggaagt gctcagtctg tccgaaggtg acgattacct ggcggcacgg 480
gtttccctcg gcgcgctagg agtgatctca caggtcaccc tgcagacggt tccgctattc 540
acgttgcatc gccatgatca gcgacgctcg ctggcgcaga cgctggagcg cctcgacgag 600
ttcgtggacg gtaatgacca tttcgagttt ttcgtattcc cttacgcaga taaggcgttg 660
acgcgcacca tgcatcgcag tgacgagcag cccaaaccca cgcccgggtg gcagcgcatg 720
gtcggcgaga acttcgagaa cgggggattg agcctgatct gccagaccgg ccgtcgtttt 780
cctagtgtgg cgccgcgact gaaccgcctg atgacgaaca tgatgtcgtc ctccaccgtg 840
caagaccgcg cctacaaggt ctttgcgacc caacgcaagg tcaggttcac cgagatggag 900
tacgcgatcc cgcgtgaaaa cgggcgcgag gcgctccagc gtgtcatcga ccttgtgcgc 960
cgtcgcagct tgccgatcat gtttccgatt gaggtgcgat tctccgcccc cgacgattcc 1020
ttcctgtcga ccgcatatgg gcgcgacact tgctacatcg cggttcatca atacgccggt 1080
atggagttcg aaagctactt ccgcgccgtc gaggagatca tggacgacta cgccggtcgg 1140
ccacactggg gtaaacgtca ctatcagacc gccgccacgc ttcgtgagcg ctatccgcag 1200
tgggatcggt tcgccgcggt tcgcgatcgc ctcgatccgg accgggtgtt tctcaacgac 1260
tacacccggc gcgttctcgg tccc 1284

<210> SEQ ID NO 107
<211> LENGTH: 309
<212> TYPE: DNA
<213> ORGANISM: Mycobacteria tuberculosis

<400> SEQUENCE: 107
ttgggttcaa caggaggtag ccaacccatg acggcgaatc gagggcccgc tgcaatctcg 60
agcggctcga actctggccg cgttctcgac accgcccggg gtatcctcat cgctcttcgg 120
cggtgccccg cagagaccgc gttcgacgag ttgcacaacg ccgctcaacg gcacagattg 180
ccggtcttcg aaatagcttg ggcactagtg catttggcgg tcgagggaag cacgccatgc 240
cggagcttcg tcgatgccca gtcggcggct cggcgggagt ggggtcagct ttttgcgcat 300
gcggcggcg 309

<210> SEQ ID NO 108
<211> LENGTH: 744
<212> TYPE: DNA
<213> ORGANISM: Mycobacteria tuberculosis

<400> SEQUENCE: 108
gtgccgccta cggaaggaaa gtcgacaacg aatcgcgacg aaggcatcca ggtgctccgt 60
cgcgccgtcg ccgcgctgga cgaaatagct gccgaaccgg gacacctgcg cctagtcgat 120
ctctgcgagc ggctggggct ggccaaatcg acgactcgac gcttgctggt cggcctggtc 180
gaggtggggc tggttagtgt cgattcgcac ggccgcttcg cactgggcga gcgtttgctg 240

-continued

```
ggattcggaa gtgtcaccgg agcccacata gccgcggcgt tccggccgac cgtcgagcga    300

gttgcccgcg cgaccgacgg cgaaacggtc gacctgtcgg tactgcgcgg ccagcgaatg    360

tggtttgtcg accagatcga atcgtcttac cggctgcgtg cggtctcagc cgtcgggctc    420

cgcttcccgt tgaacggaac cgcgaatgga aaagcggcgc tggctgctct cgacgacgcc    480

gacgccgagg ccgcgctctg ccgtctggat cccatggtgg ccgaaggtct acggcgcgag    540

atcgtcgaga tccggcgcac cggtatcgct ttcgaccgca acgagcacac cccagggata    600

tccgcggctg cgatcgcacg acgcgccctg ggcgacaacg tgatcgcgat ctcggtgccg    660

gcgcccaccg cacgatttct ggaaaaagag cagcgcataa tcgccgcgtt gcgcgccgcc    720

gcggactcgc cggactggac tcgc                                           744
```

<210> SEQ ID NO 109
<211> LENGTH: 1218
<212> TYPE: DNA
<213> ORGANISM: Mycobacteria tuberculosis

<400> SEQUENCE: 109

```
atggcatccg tcgcccaacc cgttaggcgc cgcccaaagg accggaagaa gcagattttg     60

gatcaggccg ttggactgtt catcgaacgt ggcttccatt cggtcaaatt ggaggacatt    120

gccgaggcgg ccggggtgac cgcgcgcgcg ttgtatcgcc actacgacaa caagcaggcg    180

ttgctcgccg aagcgatccg aaccggccag gatcagtacc agagcgcgcg tcgtctcacc    240

gagggcgaga cggagccgac gccgcggccg ttgaacgccg atctggaaga cctgatcgcc    300

gcggcggtcg cctctcgggc gttgacggtg ctgtggcagc gcgaggcccg ctacctcaac    360

gaggacgacc gcacggcggt ccggcgccgc atcaacgcga tcgtcgccgg catgcgtgac    420

agcgtgctgc tggaggtgcc cgatctgagt ccacagcatt cggagttgcg ggcgtgggcg    480

gtgtccagca ctttgaccag cctgggccgg cacagcctaa gcctgccggg cgaggaactg    540

aaaaagcttc tctaccaggc gtgtatggcc gcggcaagga cgcctcccgt ctgcgaattg    600

ccgccactgc cggccggtga tgccgcacgc gacgaggccg acgtgctgtt ctcccgctac    660

gagaccctgc tggccgcggg cgcgcggctg ttccgtgcgc agggctatcc ggccgtcaac    720

accagcgaaa tcggcaaggg agccggcatc gcgggcccgg ggctgtaccg ttcgttttct    780

tccaaacagg ccatcctgga cgcgctcatc cgccgcctcg acgagtggcg ctgcctggag    840

tgcatccgag cgctacgagc gaatcagcaa gcggcacaac ggttgcgcgg ccttgtccaa    900

gggcacgttc ggatcagctt ggacgctccg gatctggtgg cagtgtcggt caccgaactg    960

tcgcacgcct ctgtcgaagt acgcgacggc tacctgcgaa atcagggcga ccgcgaggcc   1020

gtgtggatcg acctcatcgg caagctggta cccgcgacca gtgtcgccca ggggcgactg   1080

ctggtcgcgg cggcgattag cttcatcgaa gacgtcgctc gcacctggca tctcacgcgc   1140

tacgccggag tcgccgacga gatcagtggc ctggcgctgg cgatcctgac cagcggggca   1200

ggtaacctct tgcgcgca                                                 1218
```

<210> SEQ ID NO 110
<211> LENGTH: 795
<212> TYPE: DNA
<213> ORGANISM: Mycobacteria tuberculosis

<400> SEQUENCE: 110

```
atggtaatcg tggccgacaa ggcggccggt cgggtcgctg atccggtctt gcggccggtg     60
```

-continued

```
ggcgcgctgg gcgatttctt cgcgatgacg ctcgacacgt ccgtgtgcat gttcaagccg    120

cctttcgcgt ggcgtgaata cctacttcag tgctggttcg tggcgcgggt gtcgacgctg    180

cctggggtgt tgatgacgat cccatgggcg gtgatctcgg ggtttctctt caacgtcttg    240

ctgaccgaca tcggtgccgc ggacttttcc ggcaccggct gtgcgatctt caccgtgaac    300

caaagcgccc cgatcgtcac ggtcttggtg gtcgcgggcg cgggcgccac cgccatgtgc    360

gccgatctgg gtgcgcgcac catccgtgag gaactcgacg cactgcgggt gatgggcatc    420

aacccgatcc aagcgctagc ggctccgcgc gtgctggcgg ccaccacggt gtcgttggcg    480

ctgaattcgg tggtgaccgc gacggggctg atcggcgcgt tcttttgctc ggtgtttctc    540

atgcacgtct cggcgggggc atgggtgacc gggcttacca cgctgaccca caccgtggac    600

gtcgtcattt cgatgatcaa ggcgacgttg ttcgggctga tggccggact gatcgcctgc    660

tataagggca tgtcggtcgg tggcggcccg gccggagtcg gccgggcggt gaacgaaacc    720

gtggtgtttg ccttcatcgt cttgttcgtg atcaacatcg tcgtcaccgc ggtcggcatc    780

ccattcatgg tgtcc                                                     795
```

<210> SEQ ID NO 111
<211> LENGTH: 813
<212> TYPE: DNA
<213> ORGANISM: Mycobacteria tuberculosis

<400> SEQUENCE: 111

```
atgacggcag cgaaagccct tgtaagcgaa tggaatcgga tgggatcgca gatgcggttc     60

ttcgtcggca cgctggccgg gattcccgac gccctcatgc actaccgcgg cgagctgctg    120

cgggtgatcg cgcaaatggg gttggggacc ggggttcttg cggtgatcgg tggaacggtc    180

gcgatcgtcg ggttcttggc gatgaccacc ggcgcgatcg tggccgtgca gggctacaac    240

cagttcgctt cggtgggtgt ggaggcgctg accggcttcg cgtcggcctt cttcaacacc    300

cgcgagattc agcccggaac cgtgatggtc gcgctagcgg ccaccgtcgg tgccggtacc    360

accgctgcgc tgggggcgat gcggataaac gaggagatcg acgcgctcga ggtgatcggc    420

atccgcagca tcagctacct ggcgagcacc cgggtgctgg ccggagtggt cgtggccgtc    480

cctctgttct gtgtgggact gatgacggcc tacctggccg cgcgcgtcgg caccaccgcc    540

atctatggcc aggggtcggg cgtgtacgac cactacttca acacgttcct gcgcccgacc    600

gacgtgctct ggtcgtcggt tgaagtcgtc gtggtcgctc tgatgatcat gctggtgtgc    660

acctattacg gctacgccgc acatggcggg ccggccgggg ttggcgaggc ggtcggccgg    720

gccgtgcgtg cctcgatggt cgtcgcgtcg atcgcaatcc ttgtcatgac gctggccatc    780

tacggccagt cgcccaactt tcacctggcg acc                                 813
```

<210> SEQ ID NO 112
<211> LENGTH: 1275
<212> TYPE: DNA
<213> ORGANISM: M. tuberculosis

<400> SEQUENCE: 112

```
atgagacgcg ggccgggtcg acaccgtttg cacgacgcgt ggtggacgct gatcctgttc     60

gcggtgatcg gggtggctgt cctggtgacg gcggtgtcct tcacgggcag cttgcggtcg    120

actgtgccgg tgacgctggc ggccgaccgc tccgggctgg tgatggactc cggcgccaag    180

gtcatgatgc gcggtgtgca ggtcggccgg gtcgcccaga tcggtcggat cgagtgggcc    240

cagaacgggg cgagcctcag actggagatc gaccccgacc agatccggta catcccggcc    300
```

-continued

```
aatgtcgagg cacagatcag cgccaccacc gcattcggtg ccaagttcgt cgacctggtg    360

atgccgcaaa acccaagtcg tgcacggctg tccgctgggg cggtactgca ttcgaagaac    420

gtcagcacgg aaatcaacac cgtcttcgaa aacgtcgtcg acctgctcaa catgatcgac    480

ccgctgaaac tgaacgccgt gctgaccgcg gtcgccgacg ccgttcgcgg gcaaggtgaa    540

cggataggcc aggccaccac cgacctcaac gaggtgctgg aggcactcaa cgcacgcggc    600

gacaccatcg gcggcaactg gcgatcgctc aagaacttca ccgacaccta tgacgcggcc    660

gcccaagaca tcctgacgat cctgaacgcc gccagcacca ccagtgcgac cgtcgtgaat    720

cattcgacgc agctggatgc cttgctactc aacgccatcg gactatccaa cgctggcacc    780

aacctgcttg gcagcagccg agacaatctc gtcggcgcgg ccgacatcct ggcgccgacc    840

acgagcctgc tgttcaagta caaccccgaa tacacctgct tcctgcaggg cgccaagtgg    900

tatctcgaca acggcggcta tgcggcctgg ggcggggccg acgggcgcac gctacaactc    960

gatgtggcgc tactgttcgg caacgacccc tatgtctatc cggacaacct gccggttgtc   1020

gcggccaagg ggggtcccgg cggaaggccg ggatgcgggc cattgccgga tgccacccac   1080

aacttcccgg tgcgccagct ggtcaccaac accggatggg gaaccgggct ggacatccgg   1140

cccaaccccg gcatcgggca tccctgctgg gccaactact tcccggtgac ccgcgcggtg   1200

cccgagccgc cgtcgatccg tcagtgcatc cccgggccgg cgatcgggcc caaccccgcg   1260

gcgggggagc agcca                                                     1275
```

<210> SEQ ID NO 113
<211> LENGTH: 1026
<212> TYPE: DNA
<213> ORGANISM: Mycobacteria tuberculosis

<400> SEQUENCE: 113

```
atgagggaga acctgggggg cgtcgtggtg cgcctcggcg tcttcctggc ggtatgcctg     60

ctgacggcgt tcctgctgat tgccgtcttc ggggaggtgc gcttcggcga cggcaagacc    120

tactacgccg agttcgccaa cgtgtccaat ctgcgaacgg gcaagctggt gcgcatcgcc    180

ggcgtcgagg tcggcaaggt caccaggatc tccatcaacc ccgacgcgac ggtgcgggtg    240

cagttcaccg ccgacaactc ggtcaccctc acgcggggca cccgggcggt gatccgctac    300

gacaacctgt tcggtgaccg ctatttggcg ctggaggaag gggccggcgg actcgccgtt    360

cttcgtcccg gtcacacgat tccgttggcg cgcacccaac cggcgttgga tctggatgcc    420

ctgatcggtg gattcaagcc gctgtttcgt gcgctgaacc ccgagcaggt caacgcgctg    480

agcgaacagt tgctgcacgc gtttgccgga caggggccca cgatcgggtc attgctggcc    540

cagtccgcgg ccgtgaccaa caccctggcc gaccgtgatc ggctgatcgg gcaggtgatc    600

accaacctca acgtggtgct gggctcgctg ggcgctcaca ccgatcggtt ggaccaggcg    660

gtgacgtcgc tatcagcgtt gattcaccgg ctcgcgcaac gcaagaccga catctccaac    720

gccgtggcct acaccaacgc cgccgccggc tcggtcgccg atctgctgtc gcaggctcgc    780

gcgccgttgg cgaaggtggt tcgcgagacc gatcgggtgg ccggcatcgc ggccgccgac    840

cacgactacc tcgacaatct gctcaacacg ctgccggaca aataccaggc gctggtccgc    900

cagggtatgt acggcgactt cttcgccttc tacctgtgcg acgtcgtgct caaggtcaac    960

ggcaagggcg gccagccggt gtacatcaag ctggccggtc aggacagcgg gcggtgcgcg   1020

ccgaaa                                                              1026
```

-continued

<210> SEQ ID NO 114
<211> LENGTH: 1230
<212> TYPE: DNA
<213> ORGANISM: Mycobacteria tuberculosis

<400> SEQUENCE: 114
atgaaatcct tcgccgaacg caaccgtctg gccatcggca cagtcggcat cgtcgtcgtc 60
gccgccgttg cgctggccgc gctgcaatac cagcggctgc cgtttttcaa ccagggcacc 120
agggtctccg cctatttcgc cgacgccggc gggctgcgca ccggcaacac cgtcgaggtc 180
tccggctatc cggtgggaaa agtgtccagc atctcgctcg acggaccggg cgtgctggtg 240
gagttcaagg tcgacaccga cgtccgactc ggaaaccgca ccgaagtggc aatcaaaacc 300
aagggcttgt tgggcagcaa gttcctcgac gtcacccccc gcggggacgg ccgactcgat 360
tctccgatcc cgatcgagcg gaccacgtcg ccctaccaac tgcccgacgc ccttggcgat 420
ttggccgcca cgatcagcgg gttgcacacc gagcggctgt ccgaatcgct ggccaccctg 480
gcgcagacct ttgccgatac gccggcgcac ttccgcaacg ccatacacgg ggtggcccgg 540
ctcgcccaaa ccctcgatga gcgcgacaac caactgcgca gcctgctggc caacgcggcc 600
aaagccaccg gggtgctggc caaccgcacc gaccagatcg tcggcctggt gcgcgacacg 660
aatgtggtct tggcgcagct gcgcacccaa agcgccgccc tggaccggat ctgggcgaac 720
atctcggcgg tggccgaaca actgcggggc ttcatcgctg agaaccgcca gcagctgcgc 780
ccggcgctgg acaagctcaa cggggtgctg gctatcgtcg aaaaccgcaa agagcgtgtg 840
cggcaggcca tcccgctgat caacacctat gtcatgtcgc tgggtgagtc gctgtcgtcg 900
ggcccgttct tcaaggcata cgtggtgaac ctgctgccgg gtcagttcgt gcaaccgttc 960
atcagcgccg cgttctccga cctggggctc gacccggcca cgttgctgcc gtcgcagctg 1020
accgacccac cgaccggtca acccggaacc ccgccgttgc cgatgcccta cccgcgcacg 1080
ggccagggcg gtgagccgcg gctgacgctg cccgacgcga tcaccggcaa tcccggcgat 1140
ccgcgctatc cgtaccggcc ggagccgccc gcgccgccgc ccggcgggcc gccgcccggc 1200
ccgcccgcgc agcagccggg agaccaaccg 1230

<210> SEQ ID NO 115
<211> LENGTH: 1269
<212> TYPE: DNA
<213> ORGANISM: Mycobacteria tuberculosis

<400> SEQUENCE: 115
gtgacaacga aactcagacg tgcccgctcg gtgttggcga ccgccctggt gctggtcgcg 60
ggcgtgatcc tggccatgcg caccgccgac gccgccgccc gcacgaccgt ggtcgcctac 120
ttcgacaaca gcaacggtgt gttcgccggt gacgacgtgc tcattcgggg cgtgccggtg 180
ggcaagatcg tcaagatcga accgcaaccg ctgcgcgcca agatttcgtt ctggttcgac 240
cgcaaatacc gagtccccgc cgatgccgcc gcggcgatcc tgtcgccgca actggtgacc 300
ggccgggcca tccagctgac accgccgtat gccggcgggc cgaccatggc cgacggcaca 360
gtaatcccgc aagagcgcac cgtggtgccg gtggagtggg acgacttgcg ggcgcaactt 420
cagcggctga ccgcattgct gcagcccacc cggccgggcg gcgtcagcac gctgggtgcg 480
ctcatcaata ctgccgccga caacctgcgc gggcaaggcg ccaccatccg cgacaccatc 540
atcaaactgt cacaagcgat ttcggctctc ggtgaccaca gcaaagacat cttctccacc 600
gtgacgaacc tgtcgacgct ggtcacggcg ctgcatgaca gcgctgacct gctcgaacgg 660

-continued

```
ctcaaccaca acctggccgc ggtgacctcg ctgctggccg atggcccgga caagatcggt     720

caggcagccg aggacctcaa cgcggtcgta gccgacgtcg gcagcttcgc cgccgagcac     780

cgcgaggcga tcggcaccgc atcagacaag ctcgcgtcaa tcaccaccgc gctggtcgac     840

agcctcgacg acatcaagca gacgctgcat atcagcccga cggtgttgca gaacttcaac     900

aacatcttcg aaccggccaa cggcgcgctg accggcgcgc tggcgggcaa caacatggcc     960

aacccaatcg ccttcctgtg cggcgcgatc caggctgcct cccggctggg cggcgagcaa    1020

gcggccaaat tgtgcgtgca atacctggcg ccgatcgtga agaaccgcca gtacaactac    1080

ccgccgctgg gggcgaacct gttcgtcggg gcgcaggcca ggcctaacga ggtcacctac    1140

agcgaggact ggctgcggcc cgattacgtt gcaccagttg cggacacgcc gccagatccg    1200

gccgcggccg tgaccgtcga tcccgcgacc ggcctgcgcg gcatgatgat gccgccgggg    1260

ggtggctcg                                                            1269
```

<210> SEQ ID NO 116
<211> LENGTH: 1131
<212> TYPE: DNA
<213> ORGANISM: M. tuberculosis

<400> SEQUENCE: 116

```
gtgaggatcg gcctgaccct ggtgatgatc gcggccgtgg tagcgagctg cggctggcgc      60

gggctgaatt cgctgccgct gcccggcacg cagggcaacg gcccggggtc cttcgcggtc     120

caggcgcagc tgccggatgt caacaacatc cagccgaact cgcgggtgcg ggttgccgac     180

gtgacggtcg gccacgtcac gaaaatcgag cgccaaggct ggcacgcgtt ggtgaccatg     240

cggctggatg gcgacgtcga tttgcccgcc aacgcaacgg ccaagatcgg caccaccagc     300

ctgctgggtt cctaccacat cgagctggcg ccaccgaaag gcgaagcgcg gcaaggcaag     360

ctgcgcgacg gttcactcat tgcgctgtca cacggtagcg cctacccaag caccgagcag     420

acgctggcag cgctgtcgct ggtgctcaac ggcggcggac tgggccaggt tcaagacatc     480

accgaggcgt tgagcaccgc gtttgccggc cgtgagcacg atctgcgcgg gctgattggg     540

cagctggaca ccttcaccgc atacctcaac aaccagtccg gtgacatcat cgcggccacc     600

gacagcctca accgcctcgt cggcaagttc gccgaccagc aacccgtctt cgatcgggcc     660

ctggccacca tccccgacgc gctcgcggtg ctggccgatg agcgggacac gctcgtcgag     720

gctgccgagc agctgagcaa gttcagcgcc ctgaccgtcg actcggtcaa caagaccacc     780

gcgaacctgg tcaccgaact gcggcaactc ggaccggtgt tggagtcgct ggccaattcc     840

ggtccggcgc tgacccgatc gctgtccctg ctggccacgt tcccgttccc gaacgagacg     900

ttccaaaatt tccagcgcgg cgaatacgcc aacctgaccg cgatcgtcga cctcacgctc     960

agccgcatcg accagggcct gttgaccggc acccgctggg agtgtcatct gacccagctc    1020

gagctgcagt ggggtcgcac cattgggcag ttccccagcc cgtgtaccgc gggctatcgg    1080

ggtaccccgg gcaatccgct gacgatcgcc taccgctggg atcaggggcc c             1131
```

<210> SEQ ID NO 117
<211> LENGTH: 1311
<212> TYPE: DNA
<213> ORGANISM: Mycobacteria tuberculosis

<400> SEQUENCE: 117

```
atgctgcatc taccgcgccg agtgatcgtt cagctggccg tctttaccgt gatcgcggtg      60
```

-continued

```
ggcgtgctgg ccatcacgtt cctgcatttc gtgaggctgc cggcgatgct tttcggcgtc    120

ggccgctaca cggtgacgat ggagctggtc gaagccggtg ggctgtatcg caccggcaat    180

gtcacctacc gcggctttga ggtgggccgg gtggcagcgg tgcggctcac cgacaccggg    240

gtgcaagcgg tgctggccct gaaatcgggc atcgatatcc cgtcggacct caaggccgag    300

gtgcacagcc acaccgcgat cggcgaaacc tacgtcgagt tgttgccgcg caacgccgcc    360

tcgccgccac tgaagaacgg cgatgtcatt gcgctggccg acacctcggt gccgcccgac    420

atcaacgacc tgctcagcgc ggccaacacc gcattggagg caatacctca cgagaacctg    480

cagaccgtca tcgacgagtc gtacaccgcg gtggccgggt tagggctcga actttcccgg    540

ctgatcaagg gctcggcgga actggcgatc gatgctcgcg cgaatctcga tccgctggtg    600

gcgctgatcg accgggcagg accggtgctg gattcgcaga cccacacctc ggatgcgatc    660

gcggcctggg cggcacagct ggccgcagtc accggccaat tgcagacaca cgactcggcg    720

gtcggcgatc tcatcgaccg gggcggtccg gcgttggggg agacgcgcca actgctcgag    780

cggctacaac ccaccgtgcc catcctgctg gccaacctgg tcagcgtcgg ccaggtcgca    840

ctcacctatc acaacgacat cgaacagctg ctggtggtgt tccccatggc catcgccgcc    900

gaacaggccg gcatcctggc caacctcaac accaagcagg cctaccgggg ccagtatctg    960

agcttcaacc tcaacctgaa cctgccgccg ccgtgcacca ccggctttct gccggcccag   1020

cagcggcgca ttcccacgtt cgaggactac ccggatcgcc cggccggtga tctgtactgc   1080

cgggtgcccc aggattcgcc gtttaacgtg cgcggcgccc gcaacatccc ctgtgaaacc   1140

gtgccgggca agcgcgcacc caccgtgaag ttatgcgaga gcgacgcgcc atacctgccg   1200

ctgaacgacg gctacaactg gaagggcgac cccaacgcca cggtgccggg tttggggtcc   1260

ggccaggaca tcccgcagac atggcaaacg atgctgctgc cgccgggcag c             1311
```

<210> SEQ ID NO 118
<211> LENGTH: 573
<212> TYPE: DNA
<213> ORGANISM: Mycobacteria tuberculosis

<400> SEQUENCE: 118

```
atgtcggtag cagtggattc cgacgccgag gatgacgccg tatcggagat cgctgaggca     60

gccggcgtgt cgccggcccc agccaaacca tccatgtcgg cgccgcggcg catgctgctg    120

ttcggcctgg tcgtcgtcgt cgctttggcg gtgctgttgt gttgctgggg atttcgcgtc    180

cagcgggcac gccatgcgca ggaccagcgt ggtcacttcc tgcaagcggc ccggcagtgc    240

gcgctgaacc taacgaccat cgactggcgc aacgccgagg cggatgtgcg ccgcattctg    300

gacggcgcca caggcgagtt ttacaacgac ttcgcccagc ggtcccagcc cttcgtcgaa    360

gtactgaggc acgcaaaggc cagcacggtc ggcacgatca ccgaggccgg gctgcagacg    420

cagaccgccg acacggccca ggcgctggtg gcggtgtccg tgcaaacgtc gaatgccggc    480

gaagccgacc cggttccacg agcgtggcga atgcgcatca ccgtgcagcg ggtcggcgac    540

cgggtcaagg tgtccgacgt cgggttcgtg ccg                                 573
```

<210> SEQ ID NO 119
<211> LENGTH: 480
<212> TYPE: DNA
<213> ORGANISM: Mycobacteria tuberculosis

<400> SEQUENCE: 119

```
gtgagctggt cgcgggtgat cgcctacggg ctgctgcccg ggctggcgtt ggcgctgacg     60
```

-continued tgtggcgcgg gcttgctgaa atggcaggac ggcgccgtcc gcgacgccgc ggttgcccgt 120
gcggaatccg tgcgggccgc gaccgacggc accaccgcgc tgctgtctta ccggcccgac 180
accgtgcagc atgacctcga gagcgcgcga agcaggctca cgggcacgtt cctcgacgcc 240
tacacacagc tgacccacga cgtggtgatc cccggcgcac agcagaagca gatctcggcc 300
gtggccaccg tcgcggccgc ggcgtcggtg tcgacttccg ccgaccgcgc cgtcgtcctg 360
ctgttcgtaa accagaccat caccgtcggc aaggacgcgc cgaccaccgc cgcttccagc 420
gttcgggtga ccctcgacaa catcaacggg cgttggctga tctcgcaatt cgaaccgatc 480

<210> SEQ ID NO 120
<211> LENGTH: 375
<212> TYPE: DNA
<213> ORGANISM: Mycobacteria tuberculosis

<400> SEQUENCE: 120
gtgcagcgcc aatcattgat gccccagcag acccttgccg ccggcgtttt cgtgggtgcg 60
ctgctatgcg gtgtcgtgac ggcggcggtg ccaccacacg cacgcgccga cgtggtcgcc 120
tatctggtca acgtgacggt acgcccgggc tacaacttcg ccaacgccga cgccgcgttg 180
agttacggac atggcctctg cgagaaggtg tctcggggcc gcccttacgc acagatcatc 240
gccgacgtca aggctgattt cgacacccgc gaccaatacc aggcctcgta tctgctcagc 300
caggctgtca acgaactctg ccccgcgctg atctggcagt tgcgaaactc cgcagtcgac 360
aatcggcgct cgggc 375

<210> SEQ ID NO 121
<211> LENGTH: 663
<212> TYPE: DNA
<213> ORGANISM: Mycobacteria tuberculosis

<400> SEQUENCE: 121
atgtcgcgtc gagcatcggc cacgtgtgcc ttgtccgcga ccaccgccgt cgccataatg 60
gctgctcccg ccgcacgggc cgacgacaag cggctcaacg acggcgtggt cgccaacgtc 120
tacaccgttc aacgtcaggc cggctgcacc aacgacgtca cgatcaaccc gcaactacaa 180
ttggccgccc aatggcacac cctcgatctg ctgaacaacc ggcacctcaa cgacgacacc 240
ggttctgacg gatccacacc gcaagaccgc gcgcatgccg ccggcttccg cgggaaagtc 300
gctgaaaccg tggcgatcaa tcccgccgta gcgatcagcg gcatcgagtt gataaaccag 360
tggtactaca accccgcgtt tttcgcgatc atgtccgact gcgccaacac ccagatcggg 420
gtgtggtcag aaaacagccc ggatcgcacc gtcgtggtgg ccgtttacgg acagcccgat 480
cgaccttccg cgatgccgcc caggggagcg gtaaccggac cgccgtcccc ggtggccgcg 540
caagagaacg ttcctatcga ccccagcccc gactacgacg ccagcgacga gatcgaatac 600
ggcatcaact ggctgccatg gatcctgcgc ggcgtgtacc cgccgcccgc aatgccgccg 660
cag 663

<210> SEQ ID NO 122
<211> LENGTH: 405
<212> TYPE: DNA
<213> ORGANISM: Mycobacteria tuberculosis

<400> SEQUENCE: 122
gtgcggtgga ttgtcgacgg tatgaacgtg atcggaagtc gtccggatgg ttggtggcgc 60

-continued gaccgccatc gcgcgatggt gatgctggtg gaaaggctcg aggggtgggc catcaccaag 120
gctcggggcg acgacgtgac ggtggtgttc gagcggccgc cgtcgaccgc catcccgtca 180
tcggtggtcg aagtggcgca tgcgcccaag gcggccgcca actcggccga cgacgagatc 240
gtccggctgg tccgatccgg cgcccagcca caagagattc gtgtggtgac atcggacaaa 300
gcgttgaccg accgggtccg agacttgggt gcggcagtct acccggcaga acggttccgt 360
gaccttatcg acccgcgcgg gtcgaacgcg gcccgccgca cgcag 405

<210> SEQ ID NO 123
<211> LENGTH: 1044
<212> TYPE: DNA
<213> ORGANISM: Mycobacteria tuberculosis

<400> SEQUENCE: 123
atgtctcaga cacccgctac aacccgcaaa acgtttcccg agatcagctc aagagcgtgg 60
gagcaccccg ccgaccggac cgccctttcc gcgctgcgcc ggctcaaagg cttcgaccag 120
atcttgaagc tgatgtcggg gatgttgcgg gaacggcagc accggctgct gtacctggcc 180
agcgcggcac gggtcgggcc gcggcagttc gccgacctcg acgcgctgct ggacgaatgc 240
gtggatgtgc tggacgcgtc ggcgaaaccc gaactctacg tgatgcagtc accaatcgcg 300
gatgccttca ccatcggcat gggcaagcca ttcaccgtga tcacctcggg gctgtacgac 360
ctggtgacac acgacgagat gcggttcgtg atgggccacg agctcggcca cgcactgtcc 420
ggccacgcgg tgtaccgcac gatgatgatg catctgctgc ggttggcccg gtcattcggc 480
gtcttgccgg ttggcggctg ggcgctgcgc gcaatcgtgg ctgcgctgct ggaatggcag 540
cgcaaatcgg agctgtccgg cgatcgcgct gggttgctgt gcgcgcagga tttggacacc 600
gcgctcaggg tggagatgaa gctcgctggc ggctgccggc tggacaagct ggactcggag 660
gccttcttgg ctcaggcccg ggaatacgag acatccggcg atatgcgcga cggggtgctc 720
aagctgctca acctggagct gcagacccat ccgttctctg tgctgcgggc tgccgccttg 780
actcactggg tggacaccgg cggctatgcc aaggtgatag ccggcgagta cccgcgtcgg 840
gccgacgacg gcaacgccaa atttgcagac gaccttggcg cggccgcccg gtactaccgg 900
gacggcttcg accagtccaa cgacccgctg atcaaaggta tccgcgacgg attcggtggc 960
atcgtcgagg gcgtgggacg ggcagcctcg aacgcggccg attcattggg ccgcaagatc 1020
accgagtggc ggcagccctc gaag 1044

<210> SEQ ID NO 124
<211> LENGTH: 564
<212> TYPE: DNA
<213> ORGANISM: Mycobacteria tuberculosis

<400> SEQUENCE: 124
atgactacgc gtccggcaac cgaccgccgc aagatgccca ctgggcggga agaggtagcg 60
gccgcaatcc tgcaggccgc caccgacctg ttcgccgagc gtgggccagc cgcgacgtcg 120
attcgcgaca tcgccgctcg atccaaggtc aaccacgggc tggtgtttcg tcacttcggc 180
accaaggacc aactggttgg ggccgtgctc gatcacctgg gcacgaagct gaccagactg 240
ttgcactccg aggcgcccgc tgacatcatc gaacgggctc tcgaccgaca tgggcgggtc 300
ttagcccggg cactgctgga cggatatccc gtgggccagc tgcaacagcg atttcccaat 360
gttgcggagc tgctcgacgc ggtacggcct cgctacgaca gcgacttggg cgcgcggctg 420
gcggtcgcgc acgcccttgc gctgcaattc ggttggcggc tctttgcgcc catgctgcgc 480
tcggcgacgg gtatcgacga gctgaccggt gacgaactac ggctgtccgt gaacgatgcg 540
gtagcccgga tcctggaacc gcac 564

<210> SEQ ID NO 125
<211> LENGTH: 702
<212> TYPE: DNA
<213> ORGANISM: Mycobacteria tuberculosis

<400> SEQUENCE: 125
gtgacgatat tgatcctgac cgacaacgtc cacgcccatg ctctggcggt cgatctgcag 60
gccaggcatg gcgatatgga cgtctatcag tcccccatcg gccagctgcc gggtgtcccg 120
cgatgtgatg tcgcagagcg cgtcgcggaa atcgtggagc ggtatgacct cgtcctttcc 180
ttccactgta aacagaggtt tcccgccgct ttgatcgatg gggtcaggtg tgtgaatgtt 240
catccgggtt tcaaccccta caaccgcggc tggtttcccc aggtcttctc gatcatcgac 300
gggcaaaaag tcggcgtgac gatccacgag atcgacgatc agttggacca tggtccgatc 360
atcgcccagc gggaatgcgc gatcgagtcg tgggattcct cgggaagtgt ctacgcccgg 420
ctgatggaca tcgagcgtga gttggtgctg gaacatttcg acgccatccg ggacggcagc 480
tacacggcta aatcgccggc caccgagggc aacctcaacc tgaaaaagga tttcgaacaa 540
ctccggcggc tagacctgaa cgagcgcgga acgtttgggc atttcctgaa tcgcctgcgc 600
gcgttgaccc atgatgattt ccgcaacgct tggttcgtcg atgcgtcagg ccgcaaggtg 660
tttgtccgcg tcgtgctcga accggagaag cccgcggaag cc 702

<210> SEQ ID NO 126
<211> LENGTH: 1599
<212> TYPE: DNA
<213> ORGANISM: Mycobacteria tuberculosis

<400> SEQUENCE: 126
atgttagcct tcccttattt gatgactatg atcactccac ctaccttcga cgttgcgttc 60
atcggcagcg gggccgcgtg ctctatgact ctgctggaaa tggccgatgc cctgctgagc 120
agcccctcgg catcgcccaa gttgcgcatc gcggtggtgg agcgagacga gcagttctgg 180
tgcggaatcc cctatggcca acgctccagc atcggatcgc tggccattca gaagctcgac 240
gatttcgccg acgagccgga aaaggccgcc taccggatct ggctggagca gaacaagcag 300
cgctggctgg cgttcttcca ggcagagggc ggtgcggccg cggcccgctg gatctgcgac 360
aaccgcgacg cattggacgg caaccagtgg ggggagctct acctgccgcg gtttctcttc 420
ggtgtatttc tgtcggagca gatgattgcc gccatcgccg cgctcggcga gcgtgacctg 480
gccgaaatcg tcaccatccg cgctgaggcc atgagcgccc actccgcaga cggccactac 540
cgaatcggcc tccgcccgtc tggaaacggt ccaacggcaa ttgctgcagg caaagtggtt 600
gtggccattg gcagcccccc gaccaaagcc atccttgcga gcgattccga acccgcattc 660
acctatatca acgatttcta ctcccccggc ggggagagca acgttgcgcg actgcgcgat 720
tcgctcgacc gcgtcgagtc gtgggagaag cgcaacgtac tggtcgtggg ttccaacgcc 780
acctcgctgg aagcgctcta cctaatgcgt cacgacgcgc gcatccgcgc acgcgtccgg 840
tccatcaccg tcatctcgcg ctccggcgtg ctgccctaca tgatctgcaa tcagccgccg 900
gagtttgact tcccgcggct gcgcacgctg ctctgtacgg aagcgatcgc cgcggcggat 960
ctcatgtccg cgatccgcga cgatctcgcg acggccgaag aacgctcgtt gaacctggcc 1020

-continued

```
gatttgtacg acgccgttgc cgccctgttt gggcaggcgc tgcacaagat ggatctcgtg   1080

cagcaggaag agttcttctg cgtgcacggc atgaacttca ccaagttggt gcggcgtgcg   1140

ggacgcgatt gccgccaggc atccgaggag ctagccgcgg acggcacgct gagcctgctc   1200

gccggcgaag tactgcgcgt ggatgcctgc gcgtccggcc agccgttcgc caccatgacc   1260

taccgagccg cgggagccga gcatacccac cccgtcccct tcgctgcggt ggtgaattgt   1320

ggcggtttcg aggagctgga cacgtgttcc tcgccgttcc tggtcagcgc gatgcagaac   1380

gggctgtgcc gcccgaaccg caccaaccgt ggccttctgg ttaacgacga cttcgaggcc   1440

agcccaggtt tttgcgtcat cgggccccta gtcggcggca atttcactcc caagatccgt   1500

ttttggcacg tcgagagcgc accgcgcgtc cggtcgctgg cgaaatcgct ggcggccagc   1560

ctgcttgctt cgctccagcc cgtcgcactg gccccatgc                          1599
```

<210> SEQ ID NO 127
<211> LENGTH: 1236
<212> TYPE: DNA
<213> ORGANISM: Mycobacteria tuberculosis

<400> SEQUENCE: 127

```
atgaagatcc gaacgttatc cggctcggtg ctggagccgc cgtccgcagt acgcgcgacc     60

ccaggcacgt ccatgttaaa actcgagccg ggtggctcga cgatccccaa gatccccttc    120

atccgcccga gctttcccgg gccagccgag ctcgccgagg acttcgtaca gatcgcccag    180

gctaactggt acacgaactt cggtccgaac gagcggcggt ttgcccgcgc cctgcgcgac    240

tatctgggac ctcatctgca cgttgctacc ctcgccaacg gcaccctggc actcctcgcg    300

gcgctccacg tcagtttcgg cgccggtacg cgggaccgct acctgctgat gccgtcgttc    360

acgttcgtcg gcgtggctca ggctgcgcta tggactgggt accgtccctg gttcatcgac    420

atcgacgcca acacatggca gccatgcgtc cactccgccc gcgccgtcat cgaacgcttc    480

cgcgaccgga tcgccggcat cctgctggcc aatgtgttcg gcgtcggcaa tccccagatc    540

agcgtctggg aggagctcgc cgccgaatgg gagctaccga ttgtgctcga ctcggcggcc    600

ggcttcggct ccacgtacgc cgacggcgag cgcctcggtg gacgcggtgc atgcgagatc    660

ttctccttcc atgcgaccaa gccgttcgcg gttggtgagg gcggcgctct ggtttctcgc    720

gatccacggc tcgtcgagca cgcatacaag ttccagaact tcggcttggt gcaaacacgc    780

gagtccatcc agctcggaat gaacggcaag ctgtcggaga tcagcgccgc tattggccta    840

cgccaactag tcgggcttga tcgccgcctg gcaagtcgcc gcaaggtcct cgagtgctat    900

cgcaccggta tggccgacgc gggtgtgcgt ttccaggaca acgccaatgt tgcgtcgctc    960

tgtttcgcga gcgcttgctg cacgtccgcc gaccacaagg ccgcggttct gggtagcctg   1020

cgtaggcacg cgatcgaggc gcgcgactac tacaacccac cgcagcaccg acatccgtac   1080

tttgtgacga atgccgagtt agtcgagtcg accgatctag ccgtcacggc ggacatttgc   1140

tcgcgaatcg tgtcgctgcc agtccacgac cacatggccc cggatgacgt tgcccgggtc   1200

gtcgccgccg tgcaggaagc ggaggtgcgc ggtgaa                             1236
```

<210> SEQ ID NO 128
<211> LENGTH: 2358
<212> TYPE: DNA
<213> ORGANISM: Mycobacteria tuberculosis

<400> SEQUENCE: 128

```
atgatcaccg aggacgcctt ccccgtcgaa ccgtggcagg tccgcgagac caagctcaac     60
```

-continued

```
ctgaacctgc tggcccagtc cgaatcccta ttcgccttgt ccaacgggca cattggatta    120
cgcggcaacc tcgacgaggg cgaacccttc ggactgccgg gcacctacct gaactctttc    180
tacgaaatcc ggccgctgcc gtacgccgag gccggttatg gatatccgga ggccggccag    240
accgttgtcg acgtcaccaa cggcaagatc tttcgcctgt tggtcggcga cgagccgttc    300
gacgtccggt atggcgaatt gatctcccac gaacggatcc tcgacctgcg cgccgggacg    360
ctgacccgcc gcgcgcactg gcgctcaccg gcgggcaagc aagtcaaagt gacgtccacc    420
cggctggtgt cgctggccca ccgcagcgtc gcggcgatcg agtacgtcgt cgaggcaatc    480
gaggaattcg ttcgcgtgac cgtgcagtcc gaactcgtca ccaacgagga cgtaccggag    540
acctcggccg acccgcgggt gtcggccatc ctggacaggc cgctacaggc cgtcgagcac    600
gaacgcaccg agcggggtgc acttctcatg caccgcaccc gagccagcgc gctgatgatg    660
gccgcaggga tggaacacga ggtcgaggtt cccgggcggg tcgagatcac caccgacgcc    720
cgcccggacc tggcccgaac caccgtgatc tgcgggctgc gcccgggaca gaagctgcgc    780
atcgtcaaat acctggccta tggctggtcc agcctgcgct cccgcccggc gctgcgcgac    840
caggccgccg gcgcgctgca cggtgcccgc tacagcggct ggcaggggct gctggacgcg    900
caacgcgcct acctcgacga cttctgggac agcgcggacg tggaggtcga gggcgacccg    960
gaatgtcagc aagcggtgcg tttcgggtta tttcacctgt tgcaggccag cgcgcgcgcc   1020
gaacgccgcg cgatccccag caaggggctc accggaaccg ggtatgacgg ccacgccttt   1080
tgggacaccg aaggtttcgt gctaccggtg ctcacctaca ccgcaccgca tgcggtcgcc   1140
gacgcgctgc ggtggcgggc gtcgacgttg gacctggcca aggagcgggc ggccgagctc   1200
ggcctggaag gtgccgcctt tccctggcgg accatccgcg gacaggagtc ctcggcctac   1260
tggccggccg gcacggcggc ctggcacatc aacgccgaca tcgcgatggc gttcgagcgg   1320
taccgcatcg tcaccggcga cggttcgctg gaggaggaat gcggccttgc ggtgctgatc   1380
gagaccgccc ggctgtggct ctcgctcggg caccacgacc gccacggcgt ctggcacctc   1440
gacggggtca ccggtcccga cgagtacacg gcggtcgtcc gcgacaacgt gttcacgaat   1500
ctgatggcgg cgcacaatct gcacaccgcc gccgatgctt gcttgcgcca ccccgaggcg   1560
gcggaggcca tgggtgtcac caccgaggag atggccgcct ggcgcgacgc ggccgacgcc   1620
gccaacattc cctacgacga ggaactcggt gtccaccagc agtgtgaagg gttcaccacc   1680
cttgcggagt gggatttcga agccaacacc acttatccgt tgctactgca cgaggcctac   1740
gtgcgcttgt atcccgcaca ggtgatcaag caggccgacc tggtgctggc gatgcagtgg   1800
cagagtcacg cgttcacgcc cgagcagaag gcgcgcaacg tcgactacta cgaacggcgc   1860
atggtgcgcg actcgtcgtt gtcggcctgc actcaggcgg tgatgtgcgc cgaggtcggc   1920
catctcgagt tggcccacga ctatgcctac gaagccgccc tgatcgacct gcgcgacctg   1980
caccgcaaca cccgtgacgg cctacacatg gcttcgctgg ccggagcctg gacggcgctg   2040
gtcgtaggct tcggcggcct acgcgacgac gagggcatcc tgtccatcga tccgcagctg   2100
cccgacggca tctcgcggct gcggttccgg ctgcgatggc gcggcttccg gctgatcgtc   2160
gacgccaacc acaccgacgt caccttcatc cttggcgacg gtcccggcac ccagctgacc   2220
atgcgccacg ccggccaaga tctgacgctg cacacggaca caccgtccac catcgccgtg   2280
```

-continued cgcacccgta agccgctgct gccgccacca ccgcagccgc caggccgcga gccagtgcac 2340
cgccgggctt tagcccgg 2358

<210> SEQ ID NO 129
<211> LENGTH: 786
<212> TYPE: DNA
<213> ORGANISM: Mycobacteria tuberculosis

<400> SEQUENCE: 129
atggcgaact ggtatcgccc gaactatccg gaagtgaggt cccgcgtgct gggtctgccc 60
gagaaggtgc gtgcttgcct gttcgacctc gacggtgtgc tcaccgatac cgcgagcctg 120
cataccaagg cgtggaaggc catgtttgac gcctacctag ccgagcgagc cgagcgcacc 180
ggcgaaaaat tcgttccctt cgaccctgcc gcggactatc acacgtatgt ggacggcaag 240
aaacgcgaag acggcgttcg atcgtttctg agcagccgcg ccatcgaaat acccgacggt 300
tccccggatg acccgggcgc cgccgagacg gtgtatggcc tgggcaaccg caagaacgac 360
atgttgcaca agctgctgcg cgacgatggg gcccaggtgt tcgacgggtc gcggcgctac 420
ctggaggcgg tcacggccgc gggtctcggt gtggccgtgg tgtcttcgag cgccaacacc 480
cgcgacgtgc tcgcgaccac cggtctggac cggttcgtcc agcagcgggt ggacggcgtg 540
acgttgcgcg aagagcacat cgccggcaag ccggcccccg actccttcct gcgcgcggca 600
gaactgttgg gggttacccc cgacgcggcg gcggtgttcg aggacgccct gtccggggtg 660
gcggccggcc gcgccggcaa cttcgccgta gtggtgggca tcaaccgaac gggccgggcg 720
gctcaggccg cccagttgcg ccgccatggc gccgacgtgg tggtaaccga tctcgccgag 780
ctgctg 786

<210> SEQ ID NO 130
<211> LENGTH: 60
<212> TYPE: DNA
<213> ORGANISM: M. tuberculosis
<220> FEATURE:
<221> NAME/KEY: misc_feature
<222> LOCATION: (1)...(60)
<223> OTHER INFORMATION: n = A,T,C or G
<220> FEATURE:
<221> NAME/KEY: misc_feature
<222> LOCATION: 2, 55
<223> OTHER INFORMATION: n = A,T,C or G

<400> SEQUENCE: 130
antagtaatg tgcgagctga gcgatgtcgc cgctcccaaa aattaccaat ggttnggtca 60

<210> SEQ ID NO 131
<211> LENGTH: 60
<212> TYPE: DNA
<213> ORGANISM: M. tuberculosis

<400> SEQUENCE: 131
agtagtaatg tgcgagctga gcgatgtcgc cgctcccaaa aattaccaat ggtttggtca 60

<210> SEQ ID NO 132
<211> LENGTH: 60
<212> TYPE: DNA
<213> ORGANISM: M. tuberbulosis

<400> SEQUENCE: 132
tgacgccttc ctaaccagaa ttgtgaattc atacaagccg tagtcgtgca gaagcgcaac 60

-continued

<210> SEQ ID NO 133
<211> LENGTH: 60
<212> TYPE: DNA
<213> ORGANISM: M. tuberculosis

<400> SEQUENCE: 133
tgacgccttc ctaaccagaa ttgtgaattc atacaagccg tagtcgtgca gaagcgcaac 60

<210> SEQ ID NO 134
<211> LENGTH: 11
<212> TYPE: DNA
<213> ORGANISM: M. tuberculosis

<400> SEQUENCE: 134
actcttggag t 11

<210> SEQ ID NO 135
<211> LENGTH: 11
<212> TYPE: DNA
<213> ORGANISM: M. tuberculosis

<400> SEQUENCE: 135
actcttggag t 11

<210> SEQ ID NO 136
<211> LENGTH: 49
<212> TYPE: DNA
<213> ORGANISM: M. tuberculosis
<220> FEATURE:
<221> NAME/KEY: misc_feature
<222> LOCATION: (1)...(49)
<223> OTHER INFORMATION: n = A,T,C or G
<220> FEATURE:
<221> NAME/KEY: misc_feature
<222> LOCATION: 15, 24
<223> OTHER INFORMATION: n = A,T,C or G

<400> SEQUENCE: 136
gtggcctaca acggngctct ccgnggcgcg ggcgtaccgg atatcttag 49

<210> SEQ ID NO 137
<211> LENGTH: 49
<212> TYPE: DNA
<213> ORGANISM: M. tuberculosis

<400> SEQUENCE: 137
gcggcctaca acggcgctct ccgcggcgcg ggcgtaccgg atatcttag 49